(12) United States Patent
Cook et al.

(10) Patent No.: US 6,191,273 B1
(45) Date of Patent: Feb. 20, 2001

(54) SUBSTITUTED CYCLIC COMPOUNDS AND MIXTURES COMPRISING SAME

(75) Inventors: Phillip Dan Cook, Lake San Marcos; Haoyun An, Encinitas; Becky Haly, La Mesa; Tingmin Wang, Carlsbad, all of CA (US)

(73) Assignee: Isis Pharmaceuticals, Inc., Carlsbad, CA (US)

( * ) Notice: Under 35 U.S.C. 154(b), the term of this patent shall be extended for 0 days.

(21) Appl. No.: 09/148,762

(22) Filed: Sep. 4, 1998

Related U.S. Application Data

(63) Continuation-in-part of application No. 08/924,835, filed on Sep. 5, 1997, now abandoned.

(51) Int. Cl.$^7$ .................................................. C07D 487/02
(52) U.S. Cl. ............................................................ 540/472
(58) Field of Search ............................... 435/71; 540/472

(56) References Cited

U.S. PATENT DOCUMENTS

| | | | |
|---|---|---|---|
| 5,218,105 | 6/1993 | Cook et al. | 536/25.31 |
| 5,578,718 | 11/1996 | Cook et al. | 536/27.21 |
| 5,780,241 | 7/1998 | Cook | 435/7.1 |

FOREIGN PATENT DOCUMENTS

| | | |
|---|---|---|
| WO 93/07883 | 4/1993 | (WO) . |
| WO 96/30377 | 10/1996 | (WO) . |

OTHER PUBLICATIONS

Aime, S. et al., "MRI Contrast Agents: Macrocyclic Lanthanide(III) Complexes with Improved Relaxation Efficiency", *J. Chem. Soc., Chem. Commun.*, 1995, 18, 1885–1886.

Arimoto, M. et al., "Semisynthetic β–Lactam Antibiotics III. Synthesis and Antibacterial Activity of 7β–[2–(2–Aminothiazol–4–YL)–2–(Substituted Carbamoylmethoxyimino)Acetamido]Cephalosporins", *J. Antibiot.*, 1986, 39(9), 1243–1256.

Achari, A. et al., "Facing up to Membranes: Structure/Function Relationships in Phospholipases", *Cold Spring Harbor Symp. Quant. Biol.*, 1987, 52, 441–452.

Bernatowicz, M.S. et al., "1H–Pyrazole–1–carboxamidine Hydrochloride: An Attractive Reagent for Guanylation of Amines and Its Application to Peptide Synthesis", *J. Org. Chem.*, 1992, 57, 2497–2502.

Bernatowicz, M.S. et al., "Urethane Protected Derivatives of 1–Guanylpyrazole for the Mild and Efficient Preparation of Guanidines", *Tetra. Lett.*, 1993, 34(21), 3389–3392.

Bomalaski, J.S. et al., "Human Extracellular Recombinant Phospholipase $A_2$ Induces an Inflammatory Response in Rabbit Joints", *J. Immunol.*, 1991, 146(11), 3904–3910.

Burack, W. R. et al., "Role of Lateral Phase Separation in the Modulation of Phospholipase $A_2$ Activity", *Biochem.*, 1993, 32, 583–589.

Campbell, M.M. et al., "Inhibition of Phospholipase $A_2$; a Molecular Recognition Study", *J. Chem. Soc., Chem. Commun.*, 1988, 1560–1562.

Carpino, L.A. et al., "Polystyrene–Based Deblocking–Scavenging Agents for the 9–Fluorenylmethyloxycarbonyl Amino–Protecting Group", *J. Org. Chem.*, 1983, 48, 661–665.

Carell, T. et al., "New promise in combinatorial chemistry: synthesis, characterization, and screening of small–molecule libraries in solution", *Chem. Biol.*, 1995, 2(3), 171–183.

Cheng, S. et al., "Novel Solution Phase Strategy for the Synthesis of Chemical Libraries Containing Small Organic Molecules", *J. Am. Chem. Soc.*, 1996, 118, 2567–2573.

Cho, W. et al., "The Chemical Basis for Interfacial Activation of Monomeric Phospholipases $A_2$; Autocatalytic Derivatization of the Enzyme by Acyl Transfer from Substrate", *J. Biol. Chem.*, 1988, 263(23), 11237–11241.

Davidson, F.F. et al., "Inhibition of Phospholipase A2 by "Lipocortins" and Calpactins; An Effect of Binding to Substrate Phospholipids", *J. Biol. Chem.*, 1987, 262(4), 1698–1705.

Davidson, F.F. et al., "1–Stearyl, 2–Stearoylaminodeoxy Phosphatidylcholine, a Potent Reversible Inhibitor of Phospholipase $A_2$", *Biochem. Biophys. Res. Commun.*, 1986, 137(2), 587–592.

Demonchaux, P. et al., "Search for the pharmacophore of the K+ channel blocker, apamin", *Eur. J. Med. Chem.*, 1991, 26, 915, 920.

Dennis, E.A., *The Enzymes*, Boyer, P.D. (ed.), Academic Press, New York, 1983, vol. 16, Chapter 9, 307–353.

Franson, R. et al., "Phospholipid metabolism by phagocytic cells. Phospholipases A2 associated with rabbit polymorphonuclear leukocyte granules", *J. Lipid Res.*, 1974, 15, 380–388.

Glaser, K.B. et al., "Phospholipase A2 enzymes: regulation and inhibition", *TiPs Reviews*, 1992, 14, 92–98.

Grainger, D.W. et al., "An enzyme caught in action: direct imaging of hydrolytic function and domain formation of phospholipase $A_2$ in phosphatidylcholine monolayers", *FEBS Lett.*, 1989, 252(1,2), 73–82.

Lombardo, D. et al., "Cobra Venom Phospholipase $A_2$ Inhibition by Manoalide", *J. Biol. Chem.*, 1985, 260(12), 7234–7240.

Märki, F. et al., "Differential inhibition of human secretory and cytosolic phospholipase $A_2$", *Agents Actions*, 1993, 38, 202–211.

(List continued on next page.)

Primary Examiner—Barbara Badio
(74) Attorney, Agent, or Firm—Woodcock Washburn Kurtz Mackiewicz & Norris LLP

(57) ABSTRACT

Novel chemical compounds and mixtures of same are provided having antibacterial and other utilities. The mixtures preferably are formed by reacting a cyclic scaffold moiety with a set of chemical substituients. Libraries formed in accordance with the invention have utility per se and are articles of commerce. They can be used to screen for pesticides, drugs and other biologically active compounds.

3 Claims, No Drawings

OTHER PUBLICATIONS

Miyake, A. et al., "The Novel Natural Product YM–26567–1 [(+)–trans–4–(3–dodecanoyl–2,4, 6–trihydroxyphenyl)–7–hydroxy–2–(4–hydroxyphenyl) chroman]: A Competitive Inhibitor of Group II Phospholipase $A_2$", *J. Pharmacol. Exp. Ther.*, 1992, 263(3), 1302–1307.

Newcomb, M. et al., "The Pyridyl Unit in Host Compounds", *J. Am. Chem. Soc.*, 1974, 96(21), 6810–6811.

Noel, J.P. et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

Oinuma, H. et al., "Synthesis and Biological Evaluation of Substituted Benzenesulfonamides as Novel Potent Membrane–Bound Phospholipase $A_2$ Inhibitors", *J. Med. Chem.*, 1991, 34, 2260–2267.

Ostresh, J.M. et al., "Peptide Libraries: Determination of Relative Reaction Rates of Protected Amino Acids in Competitive Couplings", *J. Biopolymers*, 1994, 34, 1681–1689.

O'Sullivan, M.C. et al., "A One–Step Procedure for the Selective Trifluoroacetylation of Primary Amino Groups of Polyamines", *Tetra. Lett.*, 1995, 36(20), 3451–3452.

Pon, R.T., "Solid–Phase Supports for Oligonucleotide Synthesis", Protocols for Oligonucleotides and Analogs, Agrawal, S. (ed.), Humana Press, Totowa, NJ, 1993, 465–496.

Pruzanski, W. et al., "Enzymatic Activity and Immunoreactivity of Extracellular Phospholipase A2 in Inflammatory Synovial Fluids", *Inflammation*, 1992, 16(5), 451–457.

Sampson, B.A. et al., "Identification and Characterization of a New Gene of *Escherichia coli* K–12 Involved in Outer Membrane Permeability", *Genetics*, 1989, 122, 491–501.

Scott, D.L. et al., "Interfacial Catalysis: The Mechanism of Phospholipase $A_2$", *Science*, 1990, 250, 1541–1546.

Service, R.F., "Combinatorial Chemistry Hits the Drug Market", *Science*, 1996, 272, 1266–1268.

Shipps, G.W. Jr. et al., "Solution–Phase Generation of Tetraurea Libraries", *Bioorg. Med. Chem.*, 1996, 4(5), 655–657.

Takalo, H. et al., "Synthesis of 4–(Phenylethynyl)–2,6–bis [N,N–bis–(carboxymethyl)aminomethyl]pyridine", *Acta Chem. Scand.*, 1988, B42, 373–377.

Tanaka, K. et al., "A Novel Type of Phospholipase $A_2$ Inhibitor, Thielocin A1β, and Mechanism of Action", *J. Antibiotics*, 1992, 45(7), 1071–1078.

Vishwanath, B.S. et al., "Edema–Inducing Activity of Phospholipase A2 Purified from Human Synovial Fluid and Inhibition by Aristolochic Acid", *Inflammation*, 1988, 12(6), 549–561.

Washburn, W.N. et al., "Suicide–inhibitory Bifunctionally Linked Substrates (SIBLINKS) as Phospholipase $A_2$ Inhibitors", *J. Biol. Chem.*, 1991, 266(8), 5042–5048.

Wery, J.P. et al., "Structure of recombinant human rheumatoid arthritic synovial fluid phospholipase $A_2$ at 2.2Å resolution", *Nature*, 1991, 352, 79–82.

Yang, C.C. et al., "Studies on the status of lysine residues in phospholipase $A_2$ from *Naja naja atra* (Taiwan cobra) snake venom", *Biochem. J.*, 1989, 262, 855–860.

Yuan, W. et al., "Synthesis and Evaluation of Phospholipid Analogues as Inhibitors of Cobra Venom Phospholipase $A_2$", *J. Am. Chem. Soc.*, 1987, 109, 8071–8081.

Bradshaw et al., "Enantiomeric recognition and separation of chiral organic ammonium salts by chiral pyridino–18–crown–6 ligands", *Supramolecular Chemistry*, 1993, 1, 267–275.

Lesley, S.A. et al., "Use of in Vitro Protein Synthesis from Polymerase Chain Reaction–generated Templates to Study Interaction of *Escherichia coli* Transcription Factors with Core RNA Polymerase and for Epitope Mapping of Monoclonal Antibodies", *J. Biol. Chem.*, 1991, 266(4), 2632–2638.

Ishida, K. et al., "Micropeptin 90, a Plasmin and Trypsin Inhibitor from the Blue–Green Alga *Microcystis aeruginosa* (NIES–90)", *Tetra. Lett.*, 1995, 36(20), 3535–3538.

Wang, T. et al., "Synthesis of Novel Polyazadipyridinocyclophane Scaffolds and Their Application for the Generation of Libraries", *Tetrahedron*, 1998, 54(28), 7955–7976.

Database Chemical Abstracts on STN, AN 1982:170890, Fabbrizzi et al, "Signa and pi Effects on the copper (II)/copper(I) redox couple potential in tetraazamacrocyclic complexes", Inorg. Chem. (1982), 21(5), 2083–5, Jan. 1982.*

Database Chemical Abstracts on STN, 1976:571005, Keypour et al, "Macrocycle formation. A CR isomer containing five– and seven–membered chelate rings", Inorg. Chim. Acta (1976), 19(3), L48, Jan. 1976.*

Database Chemical Abstracts on STN, AN 1997:109157, Braverman et al, "Efficacy of KIH–2023 in dry–0 and water–seeded rice (*Oryza satica*)", Weed Technol. (1996), 10(4), 876–882, Jan. 1996.*

* cited by examiner

SUBSTITUTED CYCLIC COMPOUNDS AND MIXTURES COMPRISING SAME

This application is a continuation-in-part of 08/924,835 filed Sep. 5, 1997, now abandoned.

FIELD OF THE INVENTION

This invention relates to compounds comprising substituted cyclic scaffolds moieties, and to mixtures comprising a plurality of such compounds. Such mixtures are particularly suited to pharmaceutical, pesticidal, industrial, chemical and other uses relating to the modulation detection or use of biological molecules or systems.

BACKGROUND OF THE INVENTION

Chemical libraries such as those provided by the present invention are useful per se and are appreciated to be valuable in and of themselves. Indeed, such libraries can be sold or leased in unaltered form. Moreover, such libraries generally possess biological activity themselves, e.g. antibacterial effect, or can be screened to provide useful compounds such as lead or ultimate drugs, pesticides, industrial chemical species and other useful materials.

The area of combinatorial chemistry has burgeoned recently to the point where it has begun to influence the course of drug discovery (Service, R. F., *Science*, 1996, 272, 1266–1268). Most of the combinatorial organic synthesis to date has involved the use of solid phase methods with a very few instances of solution phase chemistry reported. Cheng, S., et al., *J. Am. Chem. Soc.*, 1996, 118, 2567–73. In most cases, solid-phase, parallel synthesis is applied to provide pooled mixtures or discrete compounds in volumes which accommodate high-throughput bioassays. Thus far, there has been scant interest in "one-pot", essentially simultaneous functionalization of multiple sites. Ostresh, J. M., et al., *J. Biopolymers*, 1994, 34, 1681–1689; Carell, T., et al., *Chem. Biol.* 1995, 2, 171–83; and Shipps, G. W. Jr., et al., *Bioorg. Med. Chem.*, 1996, 4, 655–657.

There would be great benefit attained from the provision of combinatorial libraries which can be formed in solution phase, especially in essentially single reaction vessel reactions. Similar benefit would attend solution phase synthesis of such libraries under conditions which ensure representation in the product library of all possible reaction products formable under the reaction condition extant from the reactants selected for use. A further benefit would attend the preparation of such libraries from scaffold molecules possessing a relatively large number of derivatizable reaction sites. The present invention provides for the achievement of the foregoing goals.

SUMMARY OF THE INVENTION

In one aspect, the present invention provides chemical compounds having formula Q—[(Z)$_n$—L]$_m$ wherein:

Q is a cyclic scaffold moiety;

Z is NH, O, or S;

m is 2–10 (preferably 3–7, more preferably 3–5);

n is 0 or 1; and

L is a substituent selected from the group consisting of guanidinylarylalkyl, aminoarylalkyl, amidinylpiperazinylcarbonylalkyl, piperazinylcarbonylalkyl, amidinylpiperazinylcarbonylarylalkyl, piperazinylcarbonylarylalkyl, guanidinylalkylaminocarbonylalkyl, aminoalkylaminocarbonylalkyl, guanidinylalkylaminocarbonylarylalkyl, aminoalkylaminocarbonylarylalkyl, benzoimidazolylalkyl, amidinyl, hydroxyamidinyl, hydroxyalkylpyridinylalkyl, arylalkyl, cinnamyl, amidylalkyl, aroyl, alkyloyl, aminoalkyloyl, hydroxaminoyalkyloyl, methoxyaminothioalkyloyl, indolylaminoalkyloyl, amidylaminoalkyloyl, hydroxylcarbonylaminoalkyloyl, guanidinylaminoalkyloyl, imidazolylaminoalkyloyl, amino substituted acyl, carboxylakyl, carboxyl-substituted arylalky and carboxylalkyl-substituted arylalkyl, alkyloxycarbonylalkyl, hydroxysulfonylalkyl, alkyloxycarbonyl substituted pyrimidinyl, alkyloxycarbonyl substituted pyridinyl, carboxyl substituted pyrimidinyl, carboxyl substituted pyridinyl, guanidinylcarbonylalkyl, guanidinylcarbonylarylalkyl, guanidinylcarbonyl substituted pyrimidinyl, guanidinylcarbonyl substituted pyridinyl, alkyloxyphosphatealkyl, pyridinylalkyl, cyanoalkyl, cyanoaryl, nitroalkyl, nitroaryl, alkyloxyalkyl, phenolylalkyl, hydroxylarylalkyl, hydroxyquinolinylalkyl, alkylaminocarbonyl, arylaminocarbonyl, furanylaminocarbonyl, thiofuranylaminocarbonyl, alkylaminothiocarbonyl; arylaminothiocarbonyl, furanylaminothiocarbonyl, thiofuranylaminothiocarbonyl, pyridinylaminothiocarbonyl, 1,2,3-oxadiazolylalkyl, anthraquinone-2-carbonyl, pyrene-1-carbonyl, 5-(anthraquinone-2-carbonyl)amino-1-pentanyl, 5-(pyrene-1-carbonyl)amino-1-pentanyl, [[[2-(anthraquinone-2-carbonyl)amino]ethylamino]carbonyl]methyl, [[[2-pyrene- 1-carbonyl)amino]ethylamino]carbonyl]methyl, and [5-pyrene-1-carbony In another aspect, the present invention provides mixtures comprising at least six different chemical compounds having formula Q—[(Z)$_n$—L]$_m$ preferably at least ten such compounds, more preferably at least 15. It is particularly preferred that such compounds be within 20 mole percent of equimolarity in the mixtures of the invention.

The present invention also provides methods for preparing combinatorial libraries. In preferred embodiments, these methods comprise the steps of reacting a cyclic scaffold moiety with at least one compound having formula L-X wherein L is as defined above and X is a leaving group.

DETAILED DESCRIPTION OF THE INVENTION

Cyclic moieties according to the invention are those in which one ring, or two or more rings are joined together to form an extended or condensed ring. Such systems include extended aromatic systems, alicyclic systems, araalicyclic systems, bicyclic systems and even spiro systems. Examples include aromatic, alicyclic and mixed aromatic-alicyclic (araalicyclic) multiple ring systems, spiro systems, bicyclic systems, non-aromatic multiple ring systems such as adamantane, decalin, steroids and terpenes, including sesquiterpenes, diterpenes, triterpenes and tetraterpenes, and multiple ring heterocyclic systems. Illustrative ring systems include, but are not limited to, naphthalene, tetrahydronaphthalene (tetralin), anthracene, phenanthrene, fluorene, pyrene, coronene, azulene, cluorene, benzonaphthene, benzo[8]annulene, pentalene, heptalane, octalene, indene, isoindene biphenyl, biphenylene and triphenylene condensed rings; spiropentane, spiro[2.4]heptane, spiro[4.5]decane, spiro[3.4]octane, dispiro[5.1.7.2]heptadecane spiro systems, bornane, norbornane, camphor, bicyclo[2.2.1] heptane, bicyclo[3.2.1]octane, 7-methylbicyclo[2.2.1] heptane and trans and cis-bicyclo[4.4.0]decane (trans and cis-decalin) bicyclic systems, carotenes, delta-3-carene, alpha-pinene, camphor, ascaridole, azulene, cadinene, beta-selinene, ambrein, beta-amyrin and lupeol terpenes; cholesterol, lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone and 17-hydroxycorticosterone steroids.

Heterocyclic moieties according to the invention are those which include aromatic systems, alicyclic systems, araalicyclic systems, bicyclic systems and even spiro systems. Examples include aromatic, alicyclic and mixed aromatic-alicyclic (araalicyclic) multiple ring systems, spiro systems, bicyclic systems, non-aromatic multiple ring systems such as adamantane, decalin, steroids and terpenes, including sesquiterpenes, diterpenes, triterpenes and tetraterpenes, and multiple ring heterocyclic systems.

A large number of heterocyclic species can be employed as scaffold molecules in the present invention. Such heterocycles can contain nitrogen, sulfur, oxygen, and/or other heteroatoms (i.e., atoms other than carbon) within a ring structure.

Illustrative oxygen-containing heterocycles include, but are not limited to, furan, 1,4-pyran, 1,2-dioxane, 1,3-dioxane, oxepin, 1,3,5,7-tetraoxocane and 1,4,8,11-tetraoxacyclotetradecane. Illustrative sulfur-containing heterocycles include, but are not limited to thiophene, thiepine, 1,4-thiazepine. Illustrative mixed heterocycles include, but are not limited to, 1,2,3-oxathiole, isoxazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,4-oxazine, 1,3,2-oxazine, 1,3,6-oxazine, 1,2,6-oxazine, 1,4-oxazine o-isoxazine, p-isoxazine, 1,2,5-oxathiazine, 1,2,6-oxathiazine, 1,4,2-oxadiazine, 1,3,5,2-oxadiazine, 1,4-thiazepine and morpholine.

In certain preferred embodiments of the invention, the heterocycle is an aromatic nitrogen heterocycle having one or more nitrogen atoms or an aliphatic nitrogen heterocycle or a non-aromatic nitrogen-containing heterocycle, such as piperidine, that is derivatized with chemical functional groups. The compounds preferably have from 3 to 9 nitrogen heteroatoms, more preferably from 3 to 6 nitrogen heteroatoms, even more preferably from 3 to 4. Illustrative monocyclic nitrogen-containing heterocycles useful in compounds of the invention include, but are not limited to, cyanuric acid, acridine, aziridine, azetine 1,3-diazetidine, cyclopentaazane, pyrrole, pyrazole, imidazole, 1,2,3-triazole, 1,2,4-triazole, 1,2,3-triazine, 1,2,4-triazine, pyridine, pyridazine, piperidine, pyrrolidine, purine, pyrimidine, pyrazine, piperazine, pyridazine, s-triazine, azepine, 1,2,4-triazepine, azocine, cyclophane, and 4-(piperazine-1-yl)pyridinophane. Cyclophanes are particularly preferred, including those disclosed, for example, in Examples 22–26 and in International Patent Application WO 96/30377, published Oct. 3, 1996, the contents of which are incorporated herein by reference.

In accordance with preferred embodiments, the heterocyclic scaffolds include a plurality of functionalizable atoms and at least some of such atoms are chemically blocked. As will be appreciated, chemical blocking groups are well known per se and the blocking and deblocking of such locations on heterocyclic scaffolds is a matter of routine. By the judicious selection of blocking species, individual, functionalizable atoms can be exposed for a specific reaction. In this way, reactions with sets of chemical substituents or with tethers, followed by reaction with chemical substituents may be easily effected. Moreover, the heterocyclic scaffolds can be reacted seriatim or on an iterative basis to give rise to predictably complex mixtures of product chemical compounds.

It is preferred that the mixtures of chemical compounds of the present invention be prepared in solution phase and, essentially, simultaneously. It is thus preferred to undertake either a single reaction or an iterative reaction series in a single reaction vessel to give rise to a complex set of reaction mixtures comprising chemical compounds of the invention. The iterative synthetic processes of the invention, which usually involve blocking and deblocking of functionalizable atoms on the heterocyclic scaffold, can take place in a single reaction vessel, in an automated system such as any of the existing types known to persons skilled in the art, or otherwise.

Other preferred embodiments of the present invention modify the heterocyclic scaffolding in one or more ways subsequent to its reaction with chemical substituent sets. Thus, such heterocycles may be either further cyclized, ring-expanded, ring-contracted, bicyclized or otherwise reacted to alter their structure, chemical properties, physical properties, or other characteristics. It will be appreciated that such further reactions will give rise to mixtures of chemical compounds having different properties from the unreacted mixtures.

It is an embodiment of the invention to modify a mixture—a library—post preparation such as by modifying the scaffold, modifying a tether or otherwise. Such modification gives rise to a still further library. Increased diversity results. Blocking or deblocking followed by further reaction is one such modification as is alteration of the scaffold or of a tether. It is also possible to modify all or part of the sets of chemical substituents to this end.

The heterocyclic scaffold should have at least two functionalizable atoms, that is, atoms which are capable of being reacted with a set of chemical substituents to give rise to a plurality of reactions at that atom with the members of set and so to accord a mixture of chemical compounds as a product mixture. Such functionalizable atoms may be widely varied to include nitrogen, oxygen, sulfur, and other species. Such functionalizable atoms may also be alpha to a carbonyl or in other position where functionalization may occur in accordance with organic chemical reaction rules.

The chemical substituents which can be reacted with the functionalizable atoms of the heterocyclic scaffold can comprise any material which is capable of reacting with the chosen functionalizable atoms. For example, if the functionalizable atom on the heterocycle is a nucleophile, then it is convenient and preferred to provide the chemical substituents, in a set of differing molecules, in a form where electrophilic displacement can occur to give rise to the mixture of chemical compounds which forms the library. Representative chemical substituents for reaction with the heterocyclic scaffolds include alkyl, acyl, aryl, alkaryl, heterocyclic, carbocyclic and other species which can undergo substitution reactions with nucleophiles or other reactive species on the heterocyclic scaffolds or on tethers connected thereto.

Preferred substituents include guanidinylarylalkyl, aminoarylalkyl, amidinylpiperazinylcarbonylalkyl, piperazinylcarbonylalkyl, amidinylpiperazinylcarbonylarylalkyl, piperazinylcarbonylarylalkyl, guanidinylalkylaminocarbonylalkyl, aminoalkylaminocarbonylalkyl, guanidinylalkylaminocarbonylarylalkyl, aminoalkylaminocarbonylarylalkyl, benzoimidazolylalkyl, amidinyl, hydroxyamidinyl, hydroxyalkylpyridinylalkyl, arylalkyl, cinnamyl, amidylalkyl, aroyl, alkyloyl, aminoalkyloyl, hydroxaminoyalkyloyl, methoxyaminothioalkyloyl, indolylaminoalkyloyl, amidylaminoalkyloyl, hydroxylcarbonylaminoalkyloyl, guanidinylaminoalkyloyl, imidazolylaminoalkyloyl, amino substituted acyl, carboxylakyl, carboxyl-substituted arylalky and carboxylalkyl-substituted arylalkyl, alkyloxycarbonylalkyl, hydroxysulfonylalkyl, alkyloxycarbonyl substituted pyrimidinyl, alkyloxycarbonyl substituted pyridinyl, carboxyl substituted pyrimidinyl, carboxyl substituted pyridinyl, guanidinylcarbonylalkyl, guanidinylcarbonylarylalkyl, guanidinylcarbonyl substituted pyrimidinyl, guanidinylcarbonyl substituted pyridinyl, alkyloxyphosphatealkyl, pyridinylalkyl, cyanoalkyl, cyanoaryl, nitroalkyl, nitroaryl, alkyloxyalkyl, phenolylalkyl, hydroxylarylalkyl, hydroxyquinolinylalkyl, alkylaminocarbonyl, arylaminocarbonyl, furanylaminocarbonyl, thiofuranylaminocarbonyl, alkylaminothiocarbonyl; arylaminothiocarbonyl, furanylaminothiocarbonyl, thiofuranylaminothiocarbonyl, pyridinylaminothiocarbonyl, and 1,2,3-oxadiazolylalkyl groups.

A preferred group of chemical substituents include conjugate groups. Conjugate groups of the invention include intercalators, reporter molecules, polyamines, polyamides, polyethylene glycols, and polyethers. Typical conjugates groups include cholesterols, phospholipids, biotin, phenazine, phenanthridine, anthraquinone, acridine, fluoresceins, rhodamines, coumarins, and dyes. Other representative conjugate groups are disclosed in International Patent Application PCT/US92/09196, filed Oct. 23, 1992, U.S. Pat. No. 5,578,718, issued Jul. 1, 1997, and U.S. Pat. No. 5,218,105. Each of the foregoing is commonly assigned with this application. The entire disclosure of each is incorporated herein by reference.

Preferred conjugate groups include substituted and unsubstituted anthraquinone and pyrene. Conjugate groups can be attached to the heterocyclic scaffolds of the invention in a number of ways that include the use of tether groups. Preferred conjugate groups include but are not limited to anthraquinone-2-methyl; pyrene-1-butyryl; anthraquinone-2-carbonyl; pyrene-1-carbonyl; 5-(anthraquinone-2-carbonyl)amino-1-pentanyl; 5-(pyrene-1-carbonyl)amino-1-pentanyl; [[[2-(anthraquinone-2-carbonyl)amino]-ethylamino]carbonyl]methyl; [[[2-(pyrene-1-carbonyl)amino]-ethylamino]carbonyl]methyl; and [5-(pyrene-1-carbonyl)amino]pentanoxy groups.

The term alkyl as used herein includes but is not limited to aliphatic compounds having from 1 to about 20 carbon atoms. Aryl groups include but are not limited to substituted and unsubstituted aromatic and heteroaromatic groups having 3 to about 10 carbon atoms. Aralkyl groups (generally $C_7$–$C_{20}$) include but are not limited to groups having both aryl and alkyl functionalities, such as benzyl and xylyl groups. These groups can be substituted with a variety of substituents, in replacement, for example, of one or more hydrogen atoms in the compound, or can be unsubstituted. Typical substituents include, but are not limited to, hydroxyl, alkoxy, alcohol, benzyl, phenyl, nitro, thiol, thioalkoxy, halogen, or alkyl, aryl, alkenyl, or alkynyl groups.

Particularly preferred examples of L substituents according to the invention (in some instances in the form of a compound having formula L-X) include 3-[N-(N,N-(bis-t-Boc)-guanidinyl] benzylbromide, 3-(N-t-Boc) aminobenzylbromide, N-Bromoacetyl-N(N,N-bis-t-Boc-guanidinyl)piperazine, N-(4-chloroacetyl)-N-[(N,N-bis-t-Boc)-guanidinyl] piperazine, N-(3-chloromethylbenzoyl)-N (N,N-bis-t-Boc-guanidinyl)piperazine, N-(4-chloromethylbenzoyl)-N(N,N-bis-t-Boc-guanidinyl) piperazine, N-t-Boc-N-bromoacetyl-piperazine, N-t-Boc-N-chloroacetyl-piperazine, N-t-Boc-N-(4-chloromethylbenzoyl)-piperazine, N'-(t-Boc)-N"-(α-chloro) acetyl ethylenediamine, 2-Bromomethyl Pyridine-6-methanol, N'-(t-Boc)-N"-p-(chloromethyl)benzoyl ethylenediamine, N-t-Boc-N-(4-chloromethylbenzoyl)-piperazine, N'-Boc-N"-(3-chloromethylbenzoyl)-1,2-diaminoethane, t-Boc-2-chloromethylbenzimidazole, 2-Bromo-N'-[2'-(bis-N-t-Boc-)ethylguanidino]-acetamide, 2-Bromo-N-[2'-(N'-t-Boc)ethylamino]-acetamide, benzyl bromide, α-bromo-m-xylene, 3-fluorobenzyl bromide, 3-cyanobenzyl bromide, cinnamyl bromide, 3-chlorobenzyl bromide, 3-nitrobenzyl bromide, methyl 3-(bromomethyl) benzoate, α'-bromo-α,α,α-trifluoro-m-xylene, 3-bromobenzyl bromide, α-Bromoacetamide, Benzoylbromide, Bromoacetic acid, 3-chloromethyl-1,2,3-oxadiazole, P-bromomethylbenzoic acid, p-bromomethylphenylacetic acid, p-cyano-benzylbromide, t-Butyl-α-Bromoacetate, Methyl 2-chloro-4-trifluoromethyl-5-pyrimidine carboxylate, Diethyl chloromethylphosphonate, Methyl α-bromoacetate, p-Methylester benzylbromide, Ethyl 6-chloro-5-cyano-2-trifluoromethyl-3-pyridinecarboxylate, 1,6-dichloro-4-bromomethylpyridine, 3-Nitro-4-bromomethylbenzoic acid, 4-bromomethyl-3-nitrobenzoic acid, 3-guanidinylbenzyl, N-methylenecarbonyl-N-guanidinyl piperazine, N-Guanidinylethyl-N-methylenecarbonyl, 3-aminobenzyl, N-methylenecarbonyl-piperazine, 4-carboxymethyl benzylchloride, N-(4-methylenebenzoyl)-N-guanidinyl piperazine, N-(3-methylenebenzoyl)-piperazine, 2-methylenebenzimidazole, N-p-methylenebenzoyl ethylenediamine, N-(3-methylenebenzoyl)-N-guanidinyl piperazine, Bromoacetonitrile, bromonitromethane, N,N'-Bis(t-Boc)-1H-pyrazol-1-carboxamidine, amidine, N1-methylenecarboxy-N4-amidinyl piperazine, 3-guanidinyl benzyl, methoxymethylene, 4-methoxyphenol, 4-methylphenol, 4-nitrophenol, 4-trifluoromethylphenol, 4-chlorophenol, 4-bromophenol, 2,6-dimethylphenol, 5-chloro-8-hydroxyquinoline, 2-methylene-4-methoxyphenol, 2-methylene-4-methylphenol, 2-methylene-4-nitrophenol, 2-methylene-4-trifluoromethylphenol, 2-methylene-4-chlorophenol, 2-methylene-4-bromophenol, 4-methylene-2,6-dimethylphenol, 7-methylene-5-chloro-8-hydroxyquinoline, benzoic anhydride, 4-trifluoromethylbenzylbromide, 4-fluorophenyl isocyanate, 2,5-dichlorophenyl isothiocyanate, 3-methoxyphenyl isocyanate, 4-trifluoromethoxyphenyl isocyanate, cyclohexyl isocyanate, 4-ethylesterphenyl isocyanate, 3-sulfopropane, 1,3-propane sultone.

Persons of ordinary skill in the art appreciate that a wide variety of leaving groups exists, e.g. halogen, especially bromo, tosyl, mesyl and many others, which is well known for use with the chemical substituents to render them electrophilic for use in this context. All such leaving groups are contemplated hereby.

The present invention provides mixtures of at least six chemical compounds, each of which has a common heterocyclic scaffold. Each of the scaffolds has (or had, prior to reaction) at least two functionalizable atoms thereupon and is functionalized at at least one of the functionalizable atoms with a set of at least six different chemical substituents, (giving rise to the set of at least six chemical compounds.)

Although libraries in accordance with this invention can be prepared on a solid support, in microwell plates, via automation or robotics or otherwise, solution phase chemistry is greatly preferred. Indeed, the ability to accomplish the preparation of diverse libraries in solution phase is an important aspect of the invention.

It is preferred that the mixtures of the present invention contain at least about 10 chemical compounds and, more preferably, at least 15. Greater numbers of chemical compounds such as 20, 30 and even more, can also be useful for the performance of certain embodiments of this invention.

It is preferred that reaction products be "normalized" in practicing the present invention. Thus, the different reaction rates between a particular functionalizable atom on a heterocycle and a particular member of a set of, e.g. electrophiles, can be and frequently is different from the reaction rate of other members of the set. Reacting a set of such chemical substituents with the functionalizable atom on the heterocycle would be expected to give rise to disparate molar proportions of reaction products. This disproportion can be avoided through the use of normalization procedures as disclosed in U.S. application Ser. No. 07/702,018, assigned to the assignee of the present application and incorporated herein by reference. In this regard, the relative reactivities of chemical substituents are measured versus one or more standard co-reactants, e.g. common nucleophiles, and a relative mole percentage of the chemical substituents altered to reflect, in negative proportion, the relative reactivity. The resulting product mixture-will approach equimolarity which, for purposes of this invention, is defined to be within 20% of absolute equimolarity. It is still more preferred that equimolarity be achieved to within plus or minus ten mole percent of actual molarity. This can be accomplished in a number of ways, preferably through the techniques set forth in U.S. application Ser. No. 08/702,018 filed Aug. 23, 1996, and assigned to the assignee of the present application.

One aspect of the present invention is the ability to proceed iteratively. In this regard, all but one functionalizable atom on the heterocycle, e.g. the preferred purine, pyrimidine or piperazine, is chemically blocked and the remaining funtionalizable atom reacted with a set of chemical substituents (or with a tether) to give rise to a mixture of chemical compounds or a tethered scaffold. Another functionalizable atom on the heterocycle (or tether) is then deblocked and reacted with a further set of chemical substituents, which set may be the same or different from the original set, to give rise to an increasingly complex library of chemical compounds. It is important to note that while the libraries thus provided can become quite complex, such complexity is predictable. Thus, by judicious choice of the set of chemical substituents to be reacted with any particular functionalizable atom on a heterocycle, sets of products may be prepared in which every possible reaction product is represented. This is especially true when normalization of the reaction mixtures is practiced as described herein.

The actual blocking and deblocking of various functionalizable atoms is well known to persons of ordinary skill in the art. It is assumed that such artisans will readily appreciate how to accomplish blocking and deblocking reactions under particular conditions obtaining in any given reaction scheme.

The chemical libraries prepared in accordance with the present invention, which are the mixtures of chemical compounds made available hereby, have a variety of uses. Such libraries are useful per se and, indeed, are recognized as being articles of commence. There is a market for such libraries in addition to other uses.

The libraries have pharmaceutical uses per se as well. Thus, the libraries of the present invention generally possess antibiotic effect such that either gram positive or gram negative bacteria are killed upon the application of libraries of chemical compounds in accordance with this invention. Exemplary other uses of chemical libraries prepared in accordance with the present invention include as a laboratory reagent, as a screening reagent for the identification of pharmaceuticals, pesticides, bioactive, and other chemical species, for the identification of lead compounds for the foregoing and other uses, in diagnostics and many other commercial uses. A wide variety of other uses will be apparent to persons of ordinary skill in the art.

The field of combinatorial chemical libraries is now reasonably well advanced such that persons or ordinary skill in the art now know how to identify or otherwise screen for useful individual molecules from the libraries.

The chemical substituents that are covalently bound to the heterocyclic scaffolds of the invention can be referred to as functional groups or as "letters." The use of such terminology reflects the fact that the different functional groups of the compounds of the invention are positioned much like letters of the alphabet, hence the term "letter." These letters can be "reactive" or "non-reactive." By "reactive," it is meant that they will interact with a target molecule in some manner, that need not but can often be predefined. By "non-reactive," it is meant that they are not designed to primarily interact with a target molecule, and in fact while they may interact with the target molecule, the primary purpose of the non-reactive moieties is to impart other properties to the molecule such as, but not limited to, effecting up-take, biodistribution, metabolism or identification.

EXPERIMENTAL SECTION

Proton and carbon NMR spectra were recorded at 199.975 MHZ unless otherwise indicated. Other materials were purchased from Aldrich Company. High resolution and electrospray ionization mass spectrometry (FAB and ESI) were provided by The Scripps Research Institute Mass spectrometry.

Reactive functionalities that were used to make libraries of the invention are designated as $X-L_n$, where X is halo and n is the letter number e.g. from 1 to 94. Some letters are reactive as non halo substituted letters such as benzoic anhydride. The letters are listed below in numeric order:

3-[N-(N,N-(bis-t-Boc)-guanidinyl]-benzylbromide (Br-$L_1$); 3-(N-t-Boc)aminobenzylbromide (Br-$L_2$); N-bromoacetyl-N-[(N,N-Bis-t-Boc)-guanidinyl] piperazine (Br-$L_3$); N-(4-Chloroacetyl)-N-[(N,N-bis-t-Boc)-guanidinyl]-piperazine (Cl-$L_4$); N-(3-chloromethylbenzoyl)-N(N,N-bis-t-Boc-guanidinyl) piperazine ($L_5$); N-(4-chloromethylbenzoyl)-N(N,N-bis-t-Boc-guanidinyl)piperazine ($L_6$); N-boc-N-bromoacetyl-piperazine (Br-$L_7$); N-Boc-N-chloroacetyl-piperazine (Cl-$L_8$); N-boc-N-chloroacetyl-piperazine (Cl-$L_8$); N'-(t-Boc)-N"-(α-chloro)acetyl ethylenediamine (Cl-$L_{10}$); 2-bromomethyl Pyridine-6-methanol (Br-$L_{11}$); N'-(t-boc)-N"-p-(chloromethyl)benzoyl ethylene diamine (Cl-$L_{12}$); N-boc-N-(3-chloromethylbenzoyl)- piperazine (Cl-L$_{13}$); N'-boc-N"-(3-chloromethyl) phenylcarbonyl-1,2-diaminoethane (Cl-L$_{14}$); 1-Boc-2-chloromethylbenzimidazole (Cl-L$_{15}$); 2-bromo-N'-[2'-(bis-N-t-Boc)ethylguanidino]-acetamide (Br-L$_{16}$); 2-bromo-N-[2'-(N'-t-Boc)ethylamino]-acetamide (Br-L$_{17}$); benzyl bromide (Br-L$_{18}$); α-bromo-m-xylene (Br-L$_{19}$); 3-fluorobenzyl bromide (Br-L$_{20}$); 3-cyanobenzyl bromide (Br-L$_{21}$); cinnamyl bromide (Br-L$_{22}$); 3-chlorobenzyl bromide (Br-L$_{23}$); 3-nitrobenzyl bromide (Br-L$_{24}$); methyl 3-(bromomethyl)benzoate (Br-L$_{25}$); α'-bromo-α,α,α-trifluoro-m-xylene (Br-L$_{26}$); 3-bromobenzyl bromide (Br-L$_{27}$); 2-bromoacetamide (Br-L$_{28}$); benzoylbromide (Br-L$_{29}$); bromoacetic acid (Br-L$_{30}$); 3-sulfopropyl (L$_{31}$); P-bromomethylbenzoic acid (Br-L$_{32}$); p-bromomethylphenylacetic acid (Br-L$_{33}$); p-cyano-benzylbromide (Br-L$_{34}$) p-cyano-benzylbromide (Br-L$_{34}$); t-butyl-a-bromoacetate (Br-L$_{35}$); methyl 2-chloro-4-trifluoromethyl-5-pyrimidine carboxylate (Cl-L$_{36}$); diethyl chloromethylphosphonate (Cl-L$_{37}$); methyl α-bromoacetate (Br-L$_{38}$); p-Methylester benzylbromide (Br-L$_{39}$); ethyl 6-chloro-5-cyano-2-trifluoromethyl-3-pyridinecarboxylate (Cl-L$_{40}$); 1,6-dichloro-4-bromomethylpyridine (Br-L$_{41}$); 3-nitro-4-bromomethylbenzoic acid (Br-L$_{42}$); 4-bromomethyl-3-nitrobenzoic acid (Br-L$_{43}$); 3-guanidinylbenzylbromide (Br-L$_{44}$); N-Bromomethylenecarbonyl-N-quanidinyl piperazine (Br-L$_{45}$); N-guanidinylethyl-N-bromomethylenecarbonyl (Br-L$_{46}$); 3-aminobenzylbromide (Br-L$_{47}$); N-bromomethylenecarbonyl-piperazine (Br-L$_{48}$); 2-bromo-N-[2'-(N'-t-Boc)ethylamino]-acetamide (Br-L$_{49}$); N-(4-bromomethylenebenzoyl)-N-guanidinyl piperazine (Br-L$_{50}$); N-(3-bromomethylenebenzoyl)-piperazine (Br-L$_{51}$); chloromethylbenzimidazole (Cl-L$_{52}$); N-p-bromomethylenebenzoyl ethylenediamine (L$_{53}$); N-(3-chloromethylbenzoyl)-N-guanidinylpiperazine (Cl-L$_{54}$); 3-bromobenzyl bromide (Br-L$_{27}$); and bromoacetonitrile (Br-L$_{55}$); bromonitromethane (Br-L$_{56}$); N,N'-Bis(t-Boc)-amidine (L$_{57}$) (reagent-N,N'-Bis(t-Boc)-1H-pyrazol-1-carboxamidine); amidine (L$_{58}$); acetyl-N-(guanidinyl) piperazine (L$_{59}$) (reagent-N-bromoacetyl-N-[(N,N-Bis-t-Boc)-guanidinyl]piperazine); 3-(guanidinyl) benzylbromide (L$_{60}$) (reagent-3-[N-(N,N-(bis-t-Boc)-guanidinyl]-benzylbromide); methylene (L$_{61}$) (reagentformaldehyde); 4-methoxyphenol (L$_{62}$) (reagent for L$_{70}$); 4-methylphenol (L$_{63}$) (reagent for L$_{71}$); 4-nitrophenol (L$_{64}$) (reagent for L$_{72}$); 4-trifluoromethylphenol (L$_{65}$) (reagent for L$_{73}$); 4-chlorophenol (L$_{66}$) (reagent for L$_{74}$); 4-bromophenol (L$_{67}$) (reagent for L$_{75}$); 2,6-dimethylphenol (L$_{68}$) (reagent for L$_{76}$); 5-chloro-8-hydroxyquinoline (L$_{69}$) (reagent for L$_{77}$); 5-methoxy-2-hydroxybenzyl (L$_{70}$); 5-methyl-2-hydroxybenzyl (L$_{71}$) 5-nitro-2-hydroxybenzyl (L$_{72}$); 5-trifluoromethyl-2-hydroxybenzyl (L$_{73}$); 5-chloro-2-hydroxybenzyl (L$_{74}$); 5-bromo-2-hydroxybenzyl (L$_{75}$); 3,5-dimethyl-4-hydroxyphenol (L$_{76}$); 7-methylene-5-chloro-8-hydroxyquinoline (L$_{77}$); benzoic anhydride (L$_{78}$); 4-trifluoromethylbenzylbromide (Br-L$_{79}$); 4-fluorophenyl isocyanate (L$_{80}$); 2,5-dichlorophenyl isothiocyanate (L$_{81}$); 3-methoxyphenyl isocyanate (L$_{82}$); 4-trifluoromethoxyphenyl isocyanate (L$_{83}$); cyclohexyl isocyanate (L$_{84}$); 4-ethylesterphenyl isocyanate (L$_{85}$); 2-chloropyrimidine (Cl-L$_{86}$); 1,3-propane sultone (L$_{87}$); 4-trifluoromethylbenzylbromide (Br-L$_{88}$); 4-bromomethylpyridine (Br-L$_{89}$); 3-chloromethyl-1,2,3-oxadiazole (Cl-Br$_{90}$); bromoacetonitrile (Br-L$_{91}$); 2-trifluoromethylbenzylbromide (Br-L$_{92}$); and 2,6-dichlorobenzylbromide (Br-L$_{93}$).

EXAMPLE 1

3-[N-(N,N-(Bis-t-Boc)-guanidinyl]-benzyl alcohol

A solution of 3-aminobenzyl alcohol (Aldrich) (2.0 g, 16.2 mmol) and N,N'-bis(t-Boc)-1H-carboxamidine (prepared as per the procedure of Bernatowicz, M. S., *Tetrahedron Lett.*, 1993, 34, 3389–3392) (4.53 g, 14.62 mmol) in 30 mL of dry THF was stirred at room temperature for 2 days. The solvent was evaporated, and the residue was dissolved in CHCl$_3$. The solution was washed with water and brine, dried (Na$_2$SO$_4$) and concentrated. The residue was purified by flash chromatography on a silica gel column. Elution with 200:1 CH$_2$Cl$_2$—MeOH and then 4:1 hexanes-EtOAc gave the title compound as a white foam, yield 4.95 g (91.0%).

$^1$H NMR δ 1.51 (s, 9H), 1.54 (s, 9H), 4.68 (s, 2H), 7.12 (d, 1H, J=7.8 Hz), 7.34 (t, 1H, J=7.8 Hz), 7.58 (d, 2H, J=7.8 Hz), 10.36 (s, 1H), 11.61 (s, 1H). $^{13}$C NMR δ 25.5, 27.9, 28.2, 28.6, 64.0, 79.6, 83.6, 120.6, 120.9, 121.0, 123.2, 123.5, 128.6, 128.9, 136.4, 142.3, 153.2, 153.7, 163.3. HRMS (FAB) m/z 366.201 (M+H)$^+$ (C$_{18}$H$_{28}$N$_4$O$_5$ requires 366.202).

EXAMPLE 2

3-[N-(N,N-(Bis-t-Boc)-guanidinyl]-benzylbromide (Br-L$_1$)

To a solution of 3-guanidinylbenzyl alcohol (1.45 g, 3.97 mmol) in 15 mL of CH$_2$Cl$_2$ were added N-bromosuccinimide (NBS) (0.78 g, 4.4 mmol) and PPh$_3$ (1.25 g, 4.76 mmol). The resulting solution was stirred at room temperature for 2 h and the solvent was evaporated. The residue was purified by flash chromatography on a silica gel column. Elution with 50:1 hexanes-EtOAc gave the title compound as a white foam: yield 1.21 g (71.6%).

$^1$H NMR δ 1.51 (s, 9H), 1.54 (s, 9H), 4.47 (s, 2H), 7.14 (d, 1H, J=7.6 Hz), 7.32 (t, 1H, J=7.9 Hz), 7.58–7.64 (m, 2H), 10.37 (s, 1H), 11.63 (s, 1H). HRMS (FAB) m/z 428.117 (M+H)$^+$ (C$_{18}$H$_{27}$BrN$_3$O$_4$ requires 428.118). Anal. Calcd. for C$_{18}$H$_{26}$BrN$_3$O$_4$: C, 50.57; H, 6.14; N, 9.84. Found: C, 50.55; H, 6.12; N, 9.99.

EXAMPLE 3

3-(N-t-Boc)aminobenzyl alcohol

A solution of 3-aminobenzyl alcohol (0.62 g, 5.0 mmol), di-tert-butyl dicarbonate (1.09 g, 5.0 mmol) and triethylamine (1.5 g, 15 mmol) in 20 mL of dry THF was stirred at room temperature for two days. The solvent was evaporated under vacuum. The residue was dissolved in a mixture of CHCl$_3$ and H$_2$O. The layers were separated and the aqueous phase was extracted with CHCl$_3$. The combined organic phase was washed with brine, dried (Na$_2$SO$_4$) and concentrated. The residue was purified by flash chromatography on a silica gel column. Elution with 200:1 CH$_2$Cl$_2$—MeOH gave the title compound as oil: yield 0.88 g (79.3%).

$^1$H NMR δ 1.48 (s, 9H), 3.69 (t, 1H, J=5.0 Hz; ex D$_2$O), 4.49 (d, 2H, J=5.5 Hz), 6.92 (d, 1H, J=7.0 Hz), 7.10–7.26 (m, 3H). $^{13}$C NMR δ 28.3, 64.6, 80.5, 117.1, 117.5, 121.3, 128.9, 138.6, 142.0, 153.3. HRMS (FAB) m/z 223.129 (M+H)$^+$ (C$_{12}$H$_{18}$NO$_3$ requires 223.128). Anal. Calcd. for C$_{12}$H$_{17}$NO$_3$: C, 64.54; H, 7.68; N, 6.28. Found: C, 64.31; H, 7.59; N, 6.37.

EXAMPLE 4

3-(N-t-Boc) aminobenzylbromide (Br-L$_2$)

To a solution of 3-(N-t-Boc)aminobenzyl alcohol (8.25 g, 37 mmol) in 145 mL of CH$_2$Cl$_2$ were added PPh$_3$ (11.64 g, 44.4 mmol) and NBS (7.24 g, 41 mmol). The resulting solution was stirred at room temperature for two h. The solvent was evaporated under vacuum. The residue was purified by flash chromatography on a silica gel column. Elution with 50:1 hexanes-EtOAc gave compound the title compound as a white solid: yield 6.8 g (64.5%).

$^1$H NMR δ 1.52 (s, 9H), 4.42 (s, 2H), 6.77 (s, 1H), 7.04–7.07 (m, 1H), 7.20–7.25 (m, 2H), 7.51(s, 1H). $^{13}$C NMR δ 28.4, 33.5, 80.8, 118.9, 123.9, 129.7, 138.7, 152.8; HRMS (FAB) m/z 308.027 (M+Na)$^+$ (C$_{12}$H$_{16}$BrNO$_2$Na requires 308.026). Anal. Calcd. for C$_{12}$H$_{16}$BrNO$_2$: C, 50.52; H, 5.66; N, 4.91. Found: C, 50.30; H, 5.49; N, 4.74.

EXAMPLE 5

N-(N,N-Bis-t-Boc)-guanidinyl piperazine

A mixture of piperazine (34.46 g, 0.4 mol), 1,3-bis(t-Boc)-2-methyl-2-thiopseudourea (Aldrich) (29.0 g, 0.1 mol) in 260 mL of DMF was stirred at 50–60° C. for 2 h. The solvent was evaporated to dryness and the residue was dissolved in water-chloroform. The organic phase was separated and the aqueous phase was extracted with chloroform. The combined organic phase was washed with brine, dried (Na$_2$SO$_4$) and concentrated. The residue was purified by flash chromatography on silica gel using 1:2 hexanes-EtOAc, and then 1:1 EtOAc—MeOH as eluents to afford 27.2 g (83%) of the title compound as a white solid; silica gel TLC R$_f$ 0.34 (100% MeOH).

$^1$H NMR δ 1.42 (s, 18H), 2.78–2.91 (m, 4H), 3.40–3.66 (m, 4H). HRMS (FAB) m/z 329.218 (M+H)$^+$ (C$_{15}$H$_{29}$N$_4$O$_4$ requires 329.218). Anal. Calcd. for C$_{15}$H$_{28}$N$_4$O$_4$: C, 54.86; H, 8.58; N, 17.06. Found: C, 54.87; H, 8.48; N, 17.20.

EXAMPLE 6

N-Bromoacetyl-N-[(N,N-Bis-t-Boc)-guanidinyl] piperazine (Br-L$_3$)

A solution of bromoacetyl bromide (2.06 g, 10.2 mmol) in 20 mL of THF was added dropwise to a stirred solution of N-(N,N-Bis-t-Boc)-guanidinyl piperazine (3.28 g, 10 mmol) and diisopropylethylamine (2.1 mL, 1.56 g, 12 mmol) in 50 mL of THF at −30° C. The cooling bath was removed and the reaction mixture was stirred for 1.5 h. After the solvent was evaporated, the residue was dissolved in chloroform. This solution was washed with water, brine, dried (Na$_2$SO$_4$) and concentrated. The residue was purified by flash chromatography on silica gel column. Elution with 5:1, 2:1 and then 1:1 hexanes-EtOAc afforded 3.5 g (78%) of the title compound as a white solid.

Silica gel TLC R$_f$ 0.45 (1:2 hexanes-EtOAc). $^1$H NMR δ 1.46 (s, 18H), 3.48–3.75 (m, 8H), 3.85 (s, 2H); HRMS (FAB) m/z 449.141 (M+H)$^+$ (C$_{17}$H$_{30}$BrN$_4$O$_5$ requires 449.140). Anal. Calcd. for C$_{17}$H$_{29}$BrN$_4$O$_5$: C, 45.44; H, 6.49; N, 12.46. Found: C, 45.54; H, 6.25; N, 12.66.

EXAMPLE 7

N-(4-Chloroacetyl)-N-[(N,N-bis-t-Boc)-guanidinyl]-piperazine (Cl-L$_4$)

A solution of chloroacetyl chloride (1.77 g, 15.6 mmol) in 20 mL of THF was added to a stirred solution of compound N-(N,N-Bis-t-Boc)-guanidinyl piperazine (4.93 g, 15 mmol) and diisopropylethyl amine (3.2 mL, 2.34 g, 18 mmol) in 80 mL of THF at 0° C. The resulting reaction mixture was allowed to warmed to rt and stirred for 2 h. The solvent was evaporated and the residue was dissolved in chloroform. The chloroform solution was washed with water, dried (Na$_2$SO$_4$), and concentrated. The residue was purified by flash chromatography on a silica gel column. Elution with 5:1, 2:1 and then 1:1 hexanes-EtOAc afforded 5.76 g of the title compound as a white solid, yield 95%.

Silica gel TLC R$_f$ 0.48 (1:2 hexanes-EtOAc); $^1$H NMR δ 1.38 (s, 18H), 3.40–3.66 (m, 8H), 4.00 (s, 2H), 10.00 (br, 1H). HRMS (FAB) m/z 537.086 (M+Cs)$^+$ (C$_{17}$H$_{29}$ClN$_4$O$_5$Cs requires 537.088). Anal. Calcd. for C$_{17}$H$_{29}$ClN$_4$O$_5$: C, 50.43; H, 7.21; N, 13.83. Found: C, 50.56; H, 7.12; N, 14.00.

EXAMPLE 8

N-(3-chloromethylbenzoyl)-N(N,N-bis-t-Boc-guanidinyl)piperazine (Cl-L$_5$)

The title compound was prepared as described above for compound N-(4-chloroacetyl)-N-[(N,N-bis-t-Boc)-guanidinyl]piperazine from N,N-bis-t-Boc-guanidinyl piperazine (Cl-L$_4$) (3.28 g, 10 mmol), 3-(chloromethyl)benzyl chloride (1.94 g, 10.26 mmol), and diisopropylethyl amine (2.1 mL, 1.56 g, 12 mmol) in 70 mL of THF. Flash chromatographic purification afforded 4.33 g of the title compound as a white solid, yield 90%.

Silica gel TLC R$_f$ 0.42 (1:1 hexanes-EtOAc). $^1$H NMR δ 1.37 (s, 18H), 3.28–3.85 (m, 8H), 4.48 (s, 2H), 7.20–7.40 (m, 4H), 10.10 (s, 1H). MS (FAB) m/z 503 (M+Na)$^+$. HRMS (FAB) m/z 481.222 (M+H)$^+$ (C$_{23}$H$_{34}$ClN$_4$O$_5$ requires 481.221). Anal. Calcd. for C$_{23}$H$_{33}$ClN$_4$O$_5$: C, 57.43; H, 6.90; N, 11.64. Found: C, 57.33; H, 6.72; N, 11.86.

EXAMPLE 9

N-(4-chloromethylbenzoyl)-N(N,N-bis-t-Boc-guanidinyl)piperazine (Cl-L$_6$)

The title compound was prepared as described above for compound N-(4-chloroacetyl)-N-[(N,N-bis-t-Boc)-guanidinyl]piperazine (Cl-L$_4$) from N,N-bis-t-Boc-guanidinyl piperazine (6.56 g, 20 mmol), 4-(chloromothyl)benzoyl chloride (3.88 g, 20 mmol), and diisopropylethyl amine (4.2 mL, 3.1 g, 24 mmol) in 150 mL of THF. Flash chromatographic purification afforded 9.5 g of the title compound as a white solid, yield 98%.

Silica gel TLC R$_f$ 0.38 (1:1 hexanes-EtOAc). $^1$H NMR δ 1.36 (s, 18H), 3.25–3.80 (m, 8H), 4.48 (s, 2H), 7.25–7.37 (m, 4H), 10.05 (br, 1H). MS (FAB) m/z 503 (M+Na)$^+$. HRMS (FAB) m/z 481.220 (M+H)$^+$ (C$_{23}$H$_{34}$ClN$_4$O$_5$ requires 481.221). Anal. Calcd. for C$_{23}$H$_{33}$ClN$_4$O$_5$: C, 57.43; H, 6.90; N, 11.64. Found: C, 57.30; H, 7.08; N, 11.40.

EXAMPLE 10

N-Boc-N-bromoacetyl-piperazine (Br-L$_7$)

The title compound was prepared as described above for N-bromoacetyl-N(N,N-bis-t-Boc-guanidinyl)piperazine from N-Boc-piperazine (prepared as per the procedure of Carpino, L. A., et al., *J. Org. Chem.*, 1983, 48, 661–665) (23.0 g, 123 mmol), bromoacetyl bromide (25.0 g, 123 mmol), and diisopropylethyl amine (21 mL, 156 g, 120 mmol) in 240 mL of CH$_2$Cl$_2$. Flash chromatographic purification afforded 25.0 g of the title compound as pale yellow crystals, yield 66%.

Silica gel TLC $R_f$ 0.34 (1:1 hexanes-EtOAc). $^1$H NMR δ 1.37 (s, 9H), 3.30–3.56 (m, 8H), 3.80 (s, 2H). $^{13}$C NMR δ 25.8, 28.2, 28.5, 41.9, 43.2, 46.5, 80.3, 154.4, 165.4. MS (FAB) m/z 331 (M+Na)$^+$. HRMS (FAB) m/z 307.066 (M+H)$^+$ ($C_{11}H_{20}BrN_2O_3$ requires 307.065). Anal. Calcd. for $C_{11}H_{19}BrN_2O_3$: C, 43.01; H, 6.22; N, 9.12. Found: C, 43.24; H, 6.22; N, 9.37.

EXAMPLE 11

N-Boc-N-chloroacetyl-piperazine (Cl-L$_8$)

The title compound was prepared as described above for compound N-(4-chloromethylbenzoyl)-N(N,N-bis-t-Boc-guanidinyl)piperazine from N-Boc-piperazine (prepared as per the procedure of Carpino, L. A., ibid.) (9.32 g, 50 mmol), chloroacetyl chloride (5.67 g, 50.2 mmol), and diisopropylethyl amine (10.5 mL, 7.79 g, 60 mmol) in 200 mL of THF. Flash chromatographic purification afforded 12.14 g of the title compound as a white solid, yield 92%.

Silica gel TLC $R_f$ 0.50 (1:2 hexanes-EtOAc). $^1$H NMR δ 1.39 (s, 9H), 3.30–3.56 (m, 8H), 4.02 (s, 2H). $^{13}$C NMR δ 28.3, 40.8, 41.9, 43.1, 43.4, 46.1, 80.4, 154.4, 165.3. MS (FAB) m/z 263 (M+H)$^+$. HRMS (FAB) m/z 285.098 (M+Na)$^+$ ($C_{11}H_{19}ClN_2O_3Na$ requires 285.098). Anal. Calcd. for $C_{11}H_{19}ClN_2O_3$: C, 50.29; H, 7.28; N, 10.66. Found: C, 50.10; H, 7.21; N, 10.90.

EXAMPLE 12

N-Boc-N-(4-chloromethylbenzoyl)-piperazine (Cl-L$_9$)

The title compound was prepared as described above for N-(4-chloromethylbenzoyl)-N(N,N-bis-t-Boc-guanidinyl) piperazine from N-Boc-piperazine (prepared as per the procedure of Carpino, L. A., ibid.) (3.82 g, 20.5 mmol), 4-(chloromethyl)benzoyl chloride (3.88 g, 20 mmol), and diisopropylethyl amine (3.92 mL, 2.91 g, 22.5 mmol) in 60 mL of THF. Flash chromatographic purification afforded 6.4 g of the title compound as a white solid, yield 94%.

Silica gel TLC $R_f$ 0.45 (1:1 hexanes-EtOAc). $^1$H NMR δ 1.44 (s, 18H), 3.25–3.70 (m, 8H), 4.57 (s, 2H), 7.30–7.48 (m, 4H); MS (FAB) m/z 361 (M+Na)$^+$. HRMS (FAB) m/z 339.146 (M+H)$^+$ ($C_{17}H_{24}ClN_2O_3$ requires 339.147). Anal. Calcd. for $C_{17}H_{23}ClN_2O_3$: C, 60.26; H, 6.83; N, 8.26. Found: C, 60.10; H, 6.88; N, 7.99.

EXAMPLE 13

N'-(t-Boc)-N"-(α-chloro)acetyl ethylenediamine (Cl-L$_{10}$)

A solution of chloroacetylchloride (2.82 g, 25 mmol) in 50 mL of dry THF was added dropwise to the solution of mono-(t-Boc)ethylenediamine (prepared as per the procedure of Demonchaux, P., et al., *Eur. J. Med. Chem.*, 1991, 26, 915–920) (4.0 g, 25 mmol) and diisopropylethyl amine (3.15 g, 27.5 mmol) in 100 mL of dry THF at −10° C. The resulting solution was stirred at −10° C. for 30 min, and the solvent was evaporated under vacuum. The residue was dissolved in a mixture of CHCl$_3$ and H$_2$O. The phases were separated and the aqueous phase was extracted with CHCl$_3$. The combined organic phase was washed with brine, dried (Na$_2$SO$_4$), concentrated. The residue was recrystallized from 1:3 EtOAc-hexanes to give the title compound as white crystals: yield 5.47 g (92.7%).

$^1$H NMR δ 1.44 (s, 9H), 3.29–3.44 (m, 4H), 4.03 (s, 2H), 4.92 (b, 1H), 7.21 (br, 1H). $^{13}$C NMR δ 28.5, 39.7, 41.0, 42.5, 79.7, 156.8, 166.9. HRMS (FAB) m/z 237.101 (M+H)$^+$ ($C_9H_{18}ClN_2O_3$ requires 237.100). Anal. Calcd. for $C_9H_{17}ClN_2O_3$: C, 45.75; H, 7.26; N, 11.86. Found: C, 46.00; H, 7.32; N, 12.04.

EXAMPLE 14

2-Bromomethyl Pyridine-6-methanol (Br-L$_{11}$)

To a solution of 2,6-pyridinedimethanol (4.17 g, 30 mmol) were added PPh$_3$ (5.24 g, 20 mmol) and NBS (3.56 g, 20 mmol). The resulting solution was stirred at room temperature for 1 h. The solvent was evaporated, and the residue was purified by flash chromatography on a silica gel column. Elution with 2:1 hexanes-EtOAc gave product 72 which was further purified by recrystallization from 1:5 CHCl$_3$-hexanes to give white crystals: yield 1.61 g (40%).

$^1$H NMR spectrum is consistent with that reported. (Newcomb, M.; Gokel, G. W.; Cram, D. J. *J. Am. Chem. Soc.* 1974, 96, 6810).

EXAMPLE 15

N'-(t-Boc)-N"-p-(chloromethyl)benzoyl ethylene diamine (Cl-L$_{12}$)

The title compound was synthesized as above for N-Boc-N-(3-chloromethylbenzoyl)-piperazine from mono-(t-Boc) ethylenediamine (4.1 g 25.7 mmol), 4-(chloromethyl) benzoyl chloride (5.0 g, 25.7 mmol) and diisopropylethyl amine (9.96 g, 77.1 mmol). The crude material was purified by flash chromatography on a silica gel column to give the title compound as a white solid: yield 7.52 g (93.5%).

$^1$H NMR δ 1.43 (s, 9H), 3.34–3.42 (m, 2H), 3.49–3.56 (m, 2H), 4.58 (s, 2H), 5.19(br, 1H), 7.38–7.42 (m, 3H), 7.78–7.82 (m, 2H). $^{13}$C NMR δ 27.9, 28.2, 28.5, 28.8, 40.0, 42.0, 45.5, 79.9, 127.6, 128.5, 128.76, 134.2, 140.7, 157.6, 167.4. HRMS (FAB) m/z 313.133 (M+H)$^+$ ($C_{15}H_{22}ClN_2O_3$ requires 313.131). Anal. Calcd. for $C_{15}H_{21}ClN_2O_3$: C, 57.67; H, 6.78; N, 8.97. Found: C, 57.47; H, 6.74; N, 8.93.

EXAMPLE 16

N-Boc-N-(3-chloromethylbenzoyl)-piperazine (Cl-L$_{13}$)

The title compound was prepared as described above for compound N-(4-chloromethylbenzoyl)-N (N,N-bis-t-Boc-guanidinyl)piperazine from N-Boc-piperazine (prepared as per the procedure of Carpino, L. A., ibid.) (3.15 g, 16.9 mmol), 3-(chloromethyl)benzoyl chloride (3.1 g, 16.3 mmol), and diisopropylethyl amine (4 mL, 2.96 g, 22.9 mmol) in 60 mL of THF. Flash chromatographic purification afforded 5.5 g (99%) of the title compound as a white solid.

Silica gel TLC $R_f$ 0.47 (1:1 hexanes-EtOAc). $^1$H NMR δ 1.40 (s, 9H), 3.25–3.70 (m, 8H), 4.52 (s, 2H), 7.24–7.41 (m, 4H). MS (FAB) m/z 361 (M+Na)$^+$. HRMS (FAB) m/z 339.148 (M+H)$^+$ ($C_{17}H_{24}ClN_2O_3$ requires 339.147). Anal. Calcd. for $C_{17}H_{24}ClN_2O_3$: C, 60.26; H, 6.83; N, 8.26. Found: C, 60.12; H, 6.66; N, 8.37.

EXAMPLE 17

N'-Boc-N"-(3-chloromethyl)phenylcarbonyl-1,2-diaminoethane (Cl-L$_{14}$)

A solution of mono-(t-Boc)ethylenediamine (prepared as per the procedure of Demonchaux, P., et al., *Eur. J. Med. Chem.*, 1991, 26, 915–920) (1.6 g, 10 mmol) in 15 mL of dry THF was added dropwise to a solution of 3-(chloromethyl) benzoyl chloride (1.89 g, 10 mmol) and diisopropylethyl amine in 35 mL of dry THF at 0° C. The resulting solution was stirred at 0° C. for 20 min, and the solvent was evaporated under vacuum. The residue was dissolved in $CHCl_3$. The solution was washed with $H_2O$, dried ($Na_2SO_4$), and concentrated. The residue was purified by flash chromatography on a silica gel column. Elution with 100:1 $CH_2Cl_2$—MeOH gave the title compound as a white solid: yield 1.55 g (49.5%).

$^1$H NMR (CDCl$_3$) δ 1.41 (s, 9H), 3.34–3.41 (m, 2H), 3.49–3.54 (m, 2H), 4.56 (s, 2H), 5.21 (br, 1H), 7.37–7.41 (m, 1H), 7.47–7.51 (m, 2H), 7.73–7.77 (m, 1H), 7.83 (s, 1H). $^{13}$C NMR (CDCl$_3$) δ 28.2, 28.5, 39.9, 42.1, 45.7, 80.0, 127.1, 127.4, 129.2, 131.4, 134.7, 137.9, 157.7, 167.4. HRMS (FAB) m/z 313.131 (M+H)$^+$ ($C_{15}H_{22}ClN_2O_3$ requires 313.131). Anal. Calcd. for $C_{15}H_{21}ClN_2O_3$: C, 57.67; H, 6.78; N, 8.97. Found: C, 57.68; H, 6.89; N, 9.01.

EXAMPLE 18

1-Boc-2-chloromethylbenzimidazole (Cl-L$_{15}$)

A solution of di-t-butyldicarbonate (6.6 g, 30.0 mmol) in THF (50 mL) was added slowly to a stirred solution of 2-(chloromethyl)benzimidazole (5.0 g, 30 mmol) and triethylamine (5.0 mL, 36 mmol) in THF (150 mL) at 0° C. The reaction mixture was stirred at rt overnight. The solvent was evaporated, and the residue was treated with $CH_2Cl_2.H_2O$. The layers were separated and the aqueous phase was extracted with $CH_2Cl_2$. The combined organic phase was washed with brine, dried ($Na_2SO_4$), and concentrated under high vacuum. The residue was purified by flash chromatography on silica gel using 3:8 and then 4:6 EtOAc-Hexanes to give 1.8 g (25%) of the title compound as a pale oil.

$^1$H NMR (CDCl$_3$) δ 1.81 (s, 9H), 5.05 (s, 2H), 7.30–7.41 (m, 2H), 7.70–7.78 (m, 1H), 7.91–8.00 (m, 1H). $^{13}$C NMR δ 24.0, 39.9, 86.4, 115.5, 120.2, 124.4, 125.9, 133.5, 142.0, 148.0, 150.1. HRMS (FAB) m/z 267.090 (M+H)$^+$ ($C_{13}H_{16}N_2O_2Cl$ requires 267.190).

EXAMPLE 19

N'-ethylenediamine-(bis-N-t-Boc)-1-carboxamidine 1,3-Bis(t-Boc)-2-methyl-2-thiopseudourea (11.62 g, 40.0 mmol) was dissolved in THF and added dropwise over 30 min to a stirred solution of ethylenediamine (26.74 mL, 400 mmol) in 2% water (5 mL) and THF (255 mL) which was preequilibrated and maintained at 50° C. The reaction mixture was stirred at 50° C. for an additional 10 min until the absence of thiopseudourea by TLC. Prolonged reaction times resulted in degradation of the product. The solvent was evaporated in vacuo to give an oil which was dissolved in $CHCl_3$ and washed with saturated $NaHCO_3$ (×3). The organic layer was separated, dried with $MgSO_4$, and the solvent was evaporated in vacuo to give an oil. The oil was purified by flash chromatography using hexane:$CH_2Cl_2$:NEt$_3$ (20:80:1, v/v/v) to afford the title compound as a white solid (9.30 g, 77%).

$^1$H NMR (CDCl$_3$): δ 11.5 (br, 1H), 8.66 (br, 1H), 3.62 (m, 2H), 3.48 (m, 2H), 2.90 (m, 2H), 1.50 (s, 18H). $^{13}$C NMR (CDCl$_3$): δ 163.4, 156.2, 153.0, 82.9, 79.0, 43.2, 40.8, 28.3, 28.1. HRMS (ES+): M+H, calcd 303.2032, found 303.2039. Anal. Calcd. for $C_{13}H_{26}N_4O_4$: C, 51.64, H, 8.67, N, 18.53. Found: C, 51.44, H, 8.63, N, 18.13.

EXAMPLE 20

2-Bromo-N'-[2'-(bis-N-t-Boc)ethylguanidino]-acetamide (Br-L$_{16}$)

To a solution of N'-ethylenediamine-(bis-t-Boc)-1-carboxamidine (8.55 g, 28.3 mmol) dissolved in $CH_2Cl_2$ (140 mL) and THF (140 mL) was added pulverized $NaHCO_3$ (23.8 g, 283 mmol) and the mixture was stirred for 5 min at ambient temperature then cooled to −50°. Bromoacetylbromide (2.71 mL, 31.1 mmol) was added dropwise and the reaction mixture was allowed to slowly warm to ambient temperature over several hours. The solvent was evaporated in vacuo to give a solid which was suspended in $CH_2Cl_2$. The suspension was washed with water (×3). The organic layer was separated, dried with $MgSO_4$, and the solvent evaporated in vacuo to give an oil. The oil was purified by flash chromatography using hexane:EtOAc (30:70, v/v) to give the title compound as a white foam (7.84 g, 65%).

$^1$H NMR (CDCl$_3$): δ 11.45 (br, 1H), 8.65 (br, 1H), 8.20 (br, 1H), 3.85 (s, 2H), 3.60 (m, 2H), 3.45 (m, 2H), 1.50 (s, 18H). $^{13}$C NMR (CDCl$_3$): δ 166.1, 162.6, 157.2, 152.7, 83.2, 79.2, 77.6, 77.0, 76.3, 41.7, 39.4, 28.5, 28.2, 27.8, 27.6. HRMS (ES+): M+Cs, calcd 555.0219/557, found 555.0231/557. M+H, calcd 423/425, found 423/425. Anal. Calcd for $C_{15}H_{27}BrN_4O_5$: C, 42.56; H, 6.43; N, 13.24. Found: C, 43.12, H, 6.24, N, 12.88.

EXAMPLE 21

2-Bromo-N-[2'-(N'-t-Boc)ethylamino]-acetamide (Br-L$_{17}$)

The title compound was synthesized as per the procedure of Arimoto, M., et al., *J. Antibiot.*, 1986, 39, 1243–56. N1-t-Boc-ethylenediamine (9.61 g, 60.0 mmol) was dissolved in $CH_2Cl_2$ (600 mL), diethylisopropylamine (12.54 mL, 72.0 mmol) was added, the reaction mixture was cooled to −50°, and bromoacetylbromide (5.75 mL, 66.0 mmol) was added slowly to give a dark solution which was allowed to slowly warm to ambient temperature. Water (100 mL) was added to the reaction mixture, and it was stirred for 10 min. The organic layer was separated, washed with water twice and brine, and the organic layer was separated, dried with $MgSO_4$, and the solvent was evaporated in vacuo to give an oil. The crude product was purified by flash chromatography using hexane:EtOAc (20:80, v/v) to afford a beige solid (7.13 g, 42%).

$^1$H NMR (CDCl$_3$): δ 7.1 (br, 1H), 4.86 (br, 1H), 3.86 (s, 2H), 3.36 (m, 4H), 1.44 (s, 9H). $^{13}$C NMR (CDCl$_3$): δ 166.4, 156.7, 79.6, 41.2, 39.6, 28.7, 28.2. HRMS (ES+): M+H, calcd 281.0501/283, found, 281.0509/283. Anal. Calcd for $C_9H_{17}BrN_2O_3$: C, 38.45; H, 6.09; N, 9.96. Found: C, 38.78, H, 5.60, N, 9.82.

EXAMPLE 22

2,9-Bis(L$_{18-27}$)diaza-6-(t-Boc)azadecane[2.6] pyridinophane, Library 1 a) Preparation of protected bridge segment, N1-[(2-trifloroacetamido)ethan-1-yl]-N2-(trifloroacetyl)-1,3-diaminopropane(trifloroacetyl salt, N1)

Ethyl trifluoroacetate (16.7 mL, 19.89 g, 0.14 mol, 3.5 eq) was added to a solution of N-(2-aminoethyl)-1,3-propanediamine (Aldrich) (4.7 g, 40 mmol) in acetonitrile (25 mL) followed by water (0.72 g, 40 mmol, 1 eq). The resulting reaction mixture was refluxed overnight and the solvent was evaporated under reduced pressure. The residue was dried under high vacuum to give 16.8 g (99.4%) of the title compound as a white solid.

$^1$H NMR (CD$_3$OD+D$_2$O) δ 1.88–2.05 (m, 2H), 3.08 (t, 2H, J=7.6 Hz), 3.23 (t, 2H, J=6.0 Hz), 3.40 (t, 2H, J=6.8 Hz), 3.63 (t, 2H, J=6.0 Hz).

b) Protection of secondary amine of bridge segment, N1-[(t-Boc)2-trifloroacetamidoethan-1-yl]-N2-trifloroacetyl-1,3-diaminopropane Di-t-butyldicarbonate (13.2 g, 60 mmol, 1.5 eq) was added to a cooled solution of N1-[(2-trifloroacetamido)ethan-1-yl]-N2-(trifloroacetyl)-1,3-diaminopropane (trifloroacetyl salt, N1) (16.8 g, 40 mmol) and triethylamine (10.9 g, 108 mmol, 2.7 eq) in THF (140 mL). The resulting reaction mixture was stirred at room temperature overnight. Saturated ammonium chloride (270 mL) was added and the mixture was extracted with chloroform. The chloroform extract was washed with brine, dried (Na$_2$SO$_4$, and filtered. The solvent was evaporated and the residue was purified by flash chromatography on a silica gel column (17 cm×7 cm). Elution with dichloromethane and dichloromethane:methanol (20:1, v/v) afforded 16.4 g (100%) of the title compound as a white solid.

TLC: Rf 0.37; dichloromethane:methanol; 50:1, v/v; silica gel. $^1$H NMR (CDCl$_3$) δ 1.49 (s, 9 H), 1.65–1.88 (m, 2H), 3.20–3.37 (m, 4 H), 3.40–3.55 (m, 4H), 7.00 (bs, 1H), 8.10 (bs, 1H).

c) Deprotection of primary amines of bridge segment, N1-[(t-Boc)-2-aminoethyl]-1,4-diaminopropane N1-[(t-Boc)2-trifloroacetamidoethan-1-yl]-N2-trifloroacetyl-1,3-diaminopropane (16.4 g, 40 mmol) was treated with a mixture of methanol:30% aqueous ammonium hydroxide (270 mL) (1:2, v/v) and refluxed for 20 hours. The solvent was evaporated under reduced pressure and the residue was purified by flash chromatography on a silica gel column (25 cm×7 cm). Elution with methanol:30% aqueous ammonium hydroxide(50:1, 20:1 and 5:1, v/v) gave 6.0 g (69%) of the title compound as a colorless oil.

TLC: Rf 0.47; methanol:30% aqueous ammonium hydroxide; 10:1, v/v; silica gel. $^1$H NMR (CDCl$_3$) δ 1.45 (s, 9 H), 1.56–1.72 (m, 2H), 1.54 (bs, 4H, disappeared in D$_2$O), 2.68 (t, 2H, J=6.6 Hz), 2.81 (t, 2H, J=6.4 Hz), 3.18–3.35 (m, 4 H). $^{13}$C NMR (CDCl$_3$) δ 28.22, 31.75, 38.96, 40.43, 44.71, 49.81, 79.32, 155.73. Mass spectrum (HRFAB), m/z 218.186 (M+1)$^+$ (C$_{10}$H$_{24}$N$_3$O$_2$ requires 218.187).

d) Reprotection (orthogonal protection) of primary amines of bridge segment, N1-[(t-Boc)-N-(2-nitrobenzenesulfonyl)-2-aminoethyl]-N3-(2-nitrobenzenesulfonyl)-1,3-diaminopropane A solution of 2-nitrobenzenesulfonyl chloride (Aldrich, 15.2 g, 68.2 mmol, 2.33 eq) in dichloromethane (90 mL) was added dropwise to a stirred solution of N1-[(t-Boc)-2-aminoethyl]-1,4-diaminopropane (6.35 g, 29.2 mmol) and triethylamine (24 mL) in dichloromethane (90 mL) at 0° C. The resulting reaction mixture was allowed to warm to room temperature and stirred for 1 hour. The mixture was diluted with chloroform and washed with water and brine. The organic phase was dried (Na$_2$SO$_4$) and the solvent was evaporated under reduced pressure. The residue was purified by flash chromatography on a silica gel column (20 cm×5 cm). Elution with hexanes:ethyl acetate (2:1 and 1:1, v/v) afforded 11.5 g (67%) of the title compound as a ale yellow sticky oil.

TLC: Rf 0.52; hexanes:ethyl acetate; 1:2, v/v; silica gel. $^1$H NMR (CDCl$_3$) δ 1.40 (s, 9H), 1.56–1.75 (m, 2H), 2.98–3.10 (m, 2H), 3.14–3.36 (m, 6H), 5.60 (bs, 1H, disappeared in D$_2$O), 6.20 (bs, 1H, disappeared in D$_2$O), 7.66–7.88 (m, 6H), 8.02–8.13 (m, 2H). $^{13}$C NMR (CDCl$_3$) δ 23.25, 40.68, 42.43, 44.18, 45.17, 46.89, 80.64, 125.32, 130.07, 132.94, 133.13, 133.99, 147.85, 156.07. Mass spectrum (HRFAB), m/z 720.039 (M+Cs)$^+$ (C$_{22}$H$_{29}$N$_5$O$_{10}$S$_2$Cs requires 720.041).

e) Preparation of orthogonally protected cyclic moiety, 2,9-bis(2-nitrobenzenesulfonyl)diaza-6-(t-Boc)azadecane [2.6]pyridinophane A mixture of 2,6-bis(bromomethyl)pyridine (4.93 g, 18.6 mmol), cesium carbonate (24 g, 73.6 mmol) and N1-[(t-Boc)-N-(2-nitrobenzenesulfonyl)-2-aminoethyl]-N3-(2-nitrobenzenesulfonyl)-1,3-diaminopropane (10.98 g, 18.6 mmol) in anhydrous DMF (500 mL) was stirred at room temperature for 24 hours. The solvent was evaporated under reduced pressure and the residue was dissolved in a mixture of water and chloroform. The layers were separated and the aqueous phase was extracted with chloroform. The organic extract was washed with brine, dried (Na$_2$SO$_4$) and concentrated. The residue was purified by flash chromatography on a silica gel column (18 cm×5 cm). Elution with hexanes:ethyl acetate (1:1, 1:2 and 1:4, v/v) gave 2.63 g (73%) of the title compound as a white foam.

A mixture of 2,6-bis(bromomethyl)pyridine (4.93 g, 18.6 mmol), cesium carbonate (24 g, 73.6 mmol) and N1-[N-(2-nitrobenzenesulfonyl)-2-aminoethyl]-N3-(2-nitrobenzenesulfonyl)-1,3-diaminopropane (10.98 g, 18.6 mmol) in anhydrous DMF (500 mL) was stirred at room temperature for 24 hours. The solvent was evaporated under reduced pressure and the residue was dissolved in a mixture of water and chloroform. The layers were separated and the aqueous phase was extracted with chloroform. The organic extract was washed with brine, dried (Na$_2$SO$_4$) and concentrated. The residue was purified by flash chromatography on a silica gel column (18 cm×5 cm). Elution with hexanes:ethyl acetate (1:1, 1:2 and 1:4, v/v) gave 10.3 g (80%) of the title compound as a white foam.

TLC: Rf 0.50; hexanes:ethyl acetate; 1:4, v/v; silica gel. $^1$H NMR (CDCl$_3$) δ 1.40 (s, 9H), 1.67–1.85 (m, 2H), 2.60–2.80 (m, 2H), 3.04–3.15 (m, 2H), 3.25–3.46 (m, 4H), 4.55 (s, 4H), 7.48–7.80 (m, 9H), 7.96–8.10 (m, 2H). $^{13}$C NMR (CDCl$_3$) δ 26.98, 28.34, 45.36, 46.40, 47.07, 49.26, 55.24, 55.65, 79.83, 123.97, 124.25, 124.41, 130.67, 130.92, 131.91, 133.98, 138.64, 148.13, 148.36, 155.06, 155.67. Mass spectrum (HRFAB), m/z 823.086 (M+Cs)$^+$ (C$_{29}$H$_{34}$N$_6$O$_{10}$S$_2$Cs requires 823.083).

f) Selective deprotection of orthogonally protected amine positions, 2,9-diaza-6-(t-Boc)azadecane-[2.6]pyridinophane Thiophenol (Aldrich, 1.5 mL, 1.6 g, 14.5 mmol, 2.46 eq.) was added to a stirred mixture of 2,9-bis(2-nitrobenzenesulfonyl)diaza-6-(t-Boc)azadecane[2.6]pyridinophane (4.15 g, 6.0 mmol) and potassium carbonate (6.63 g, 48 mmol, 8 eq) in DMF (80 mL). The resulting blue mixture was stirred at room temperature for 2 hours. The yellow reaction mixture was concentrated under reduced pressure and the residue was dissolved in water. The solution was made basic (e.g. pH 13–14) with aqueous sodium hydroxide and extracted with chloroform. The organic extract was washed with brine, dried (Na$_2$SO$_4$), filtered, and the solvent evaporated. The residue was purified by flash chromatography on a silica gel column (20 cm×3 cm). Elution with methanol and methanol:30% aqueous ammonium hydroxide (100:1 and 50:1, v/v) afforded 1.81 g (94%) of the title compound as a colorless oil.

TLC: Rf 0.42; methanol:30% aqueous ammonium hydroxide; 50:1, v/v; silica gel. $^1$H NMR (CDCl$_3$) δ 1.35 (s, 9H), 1.48–1.65 (m, 2H), 2.19 (bs, 2H, disappeared in $D_2O$), 2.62 (t, 2H, J=6.4 Hz), 2.78 (t, 2H, J=6.2 Hz), 3.00 (t, 2H, J=6.2 Hz), 3.28 (t, 2H, J=6.4 Hz), 3.90 (s, 4H), 7.04 (t, 2H, J=7.0 Hz), 7.56 (t, 1H, J=7.0 Hz). $^3$C NMR ($CDCl_3$) δ 28.43, 29.89, 46.09, 46.39, 48.31, 48.60, 54.25, 54.67, 79.25, 120.91, 121.31, 137.14, 156.04, 159.95, 160.11. Mass spectrum (HRFAB), m/z 321.230 $(M+H)^+$ ($C_{17}H_{29}N_4O_2$ requires 321.229).

g) Preparation of Library 1, 2,9-Bis($L_{18-27}$)diaza-6-(t-Boc)azadecane[2.6]pyridinophane A mixture of benzyl bromide ($L_{18}$) (147 μL, 207 mg, 1.2 mmol), α-bromo-m-xylene ($L_{19}$) (169 μL, 222 mg, 1.2 mmol), 3-fluorobenzyl bromide ($L_{20}$) (149 μL, 227 mg, 1.2 mmol), 3-cyanobenzyl bromide ($L_{21}$) (237 mg, 1.2 mmol), cinnamyl bromide ($L_{22}$) (237 mg, 1.2 mmol), 3-chlorobenzyl bromide ($L_{23}$) (163 μL, 248 mg, 1.2 mmol), 3-nitrobenzyl bromide ($L_{24}$) (259 mg, 1.2 mmol), methyl 3-(bromomethyl)benzoate ($L_{25}$) (276 mg, 1.2 mmol), α'-bromo-α,α,α-trifluoro-m-xylene ($L_{26}$) (185 μL, 288 mg, 1.2 mmol), and 3-bromobenzyl bromide ($L_{27}$) (300 mg, 1.2 mmol) (total 12 mmol, 2.4 equiv) in 50 mL of anhydrous acetonitrile was added to a stirred mixture of compound 2,9-diaza-6-(t-Boc)azadecane[2.6]-pyridinophane (1.60 g, 5.0 mmol), and anhydrous potassium carbonate (10.0 g, 72 mmol) in 130 mL of acetonitrile. The resulting reaction mixture was stirred at rt overnight and concentrated. The residue was dissolved in a mixture of chloroform-water. The organic phase was separated, and the aqueous phase was extracted with chloroform. The combined organic phase was washed with brine, dried ($Na_2SO_4$), and concentrated. The residue was purified by flash chromatography on a silica gel column using 15:1 hexanes-EtOAc, 100% EtOAc, and then 20:1 EtOAc—MeOH as eluents. The library fractions, monitored by TLC, were collected and concentrated to afforded 2.80 g (97%) of the title library as a pale yellow oil.

MS (ES) m/z 501–659 $(M+H)^+$.

EXAMPLE 23

2,9-Bis($L_{1-10}$)diaza-6-azadecane[2.6]pyridinophane, Library 2

Trifluoroacetic acid (TFA) (35 mL,) was added to a stirred solution of Library 1 (2.80 g, 4.87 mmol) in 7 mL of chloroform at 0° C. The resulting reaction mixture was stirred at rt for 3 h, and concentrated to remove excess amount of TFA. The residue was dissolved in chloroform. The solution was washed with aqueous sodium carbonate solution, brine, dried ($Na_2SO_4$), and then concentrated. The residue was purified by flash chromatography using 100:0, 40:1 and then 5:1 MeOH-30% $NH_4OH$ to afford 2.30 g (88%) of the title library as a light yellow oil.

Silica gel TLC $R_f$ 0.35 (5:1 MeOH-30% $NH_4OH$). $^1$H NMR δ 1.65–1.82 (m, 2H), 2.28–2.35 (m, 0.3H), 2.45–2.65 (m, 4H), 2.64–2.96 (m, 4H), 3.40–4.00 (m, 10.3H), 6.20–8.40 (m, 11.3H). MS (ES) m/z 401–559 $(M+H)^+$.

EXAMPLE 24

2,9-Bis ($L_{1-10}$) diaza-6-($L_{18, 19, 20, 21, 22,\ and\ 28}$) azadecane-[2.6]pyridinophane, General Procedure for the Preparation of Libraries 3–8

A mixture of library 2 (105 mg, 0.22 mmol), a corresponding bromide of a selected letter (0.266 mmol) and $K_2CO_3$ (0.5 g, 3.6 mmol) in acetonitrile (5 mL) was stirred at rt overnight. After the solvent was evaporated, the residue was dissolved in a mixture of water-chloroform. The layers were separated, and the aqueous phase was extracted with chloroform. The combined organic phase was washed with brine, dried ($Na_2SO_4$) and concentrated. The residue was purified by preparative TLC using 90:1 MeOH-30% $NH_4OH$ as developing agent to afford libraries 3–8 as colorless to light yellow oils in 80–96% yields.

| Library # | Letter used |
|---|---|
| 3 | benzyl bromide ($L_{18}$) |
| 4 | α-bromo-m-xylene ($L_{19}$) |
| 5 | 3-fluorobenzyl bromide ($L_{20}$) |
| 6 | 3-cyanobenzyl bromide ($L_{21}$) |
| 7 | cinnamyl bromide ($L_{22}$) |
| 8 | α-Bromoacetamide ($L_{28}$) |

EXAMPLE 25

General procedures for library synthesis

A. Synthesis of libraries having 2,9-Bis($L_{n-m}$)diaza-6-(t-Boc)azadecane[2.6]pyridinophane scaffolds, Libraries 9–14

A solution containing equal molar amounts of the selected bromide or chloride letters ($R_nBr$, $R_nCl$) or 1,3-propane sultone (total 1.1 equiv per reactive site on scaffold) in acetonitrile was added to a mixture of 2,9-diaza-6-(t-Boc) azadecane[2.6]pyridinophane (1.0 equiv), and $K_2CO_3$ (5.0 g, 36 mmol) in acetonitrile (20 mL). The resulting reaction mixture was stirred at rt or 2–4 h (monitored by TLC). For the preparation of libraries using chloride functionalities, the reaction mixtures were stirred at 50–60 ° C. overnight. The reaction mixture was worked up and purified as illustrated in Example 22 for Library 1. The purified libraries were obtained as pale yellow oils or light yellow foams in 80–99% yields.

| Library # | Letters used (n-m) |
|---|---|
| 9 | 1, 3, 16, 26 and 29 |
| 10 | 2, 7, 10, 20 and 29 |
| 11 | 29–34 |
| 12 | 1, 3, 16, 2, 7, 10, 35 and 36 |
| 13 | 5, 6, 9, 15 and 37 |
| 14 | 18, 29, 36, 38, 39 and 40 |

B. Synthesis of libraries having 2,11-Bis($L_{n-m}$)diaza-7-(t-Boc)azadodecane[2.6]pyridinophane scaffolds, Libraries 15–20

Libraries 15–20 were synthesized as illustrated above for libraries 9–14 using 2,11-diaza-7-(t-Boc)azadodecane[2.6] pyridinophane as the scaffold.

| Library # | Letters used (n-m) |
|---|---|
| 15 | 1, 3, 16, 26 and 29 |
| 16 | 2, 7, 10, 20 and 29 |
| 17 | 29–34 |
| 18 | 1, 3, 16, 2, 7, 10, 35 and 36 |
| 19 | 5, 6, 9, 15 and 37 |
| 20 | 18, 29, 36, 38, 39 and 40 |

C. Synthesis of libraries having 2,11-Bis($L_{n-m}$)diaza-7-($L_{n-m}$)azadodecane[2.6]pyridinophane scaffolds, Libraries 21–27

Libraries 21–27 were synthesized as illustrated above for libraries 9–14 using 2,11-diaza-7-azadodecane-[2.6] pyridinophane as the scaffold. Prior to library synthesis the scaffold used in part B above was deblocked as per the procedures of Example 23 and functionalized at all 3 sites simultaneously to make libraries 21–27.

| Library # | Letters used (n-m) |
| --- | --- |
| 21 | 1, 3, 16, 29, 41 and 42 |
| 22 | 2, 7, 17, 29, 41 and 42 |
| 23 | 1, 4, 7, 11, 26, 29 and 35 |
| 24 | 5, 6, 9, 10, 12, 15 and 37 |
| 25 | 1, 2, 3, 7, 16, 29 and 35 |
| 26 | 29–33 and 43 |
| 27 | 28, 36, 38, 39, 40 and 41 |

EXAMPLE 26

General procedures for library synthesis via deblocking of preexisting library

A. Synthesis of libraries having 2,9-Bis($L_{n-m}$)diaza-6-azadecane[2.6]pyridinophane scaffolds, Libraries 28–33

Libraries 9–14 were each deblocked using the procedures of Example 23, thereby giving libraries 28–33 respectively. The deblocking process removes all t-Boc blocking groups whether attached directly to a scaffold or to a letter. After evaporation of the excess TFA, the libraries were dissolved in hydrochloride saturated methanol. Evaporation of the solvent gave the hydrochloride salts of the corresponding libraries as foams without further purification.

| Library # | Letters (n-m) |
| --- | --- |
| 28 | 26, 29, 44, 45 and 46 |
| 29 | 20, 29, 47, 48 and 49 |
| 30 | 29–34 |
| 31 | 30, 36 and 44–49 |
| 32 | 37, 50–52 and 54 |
| 33 | 18, 29, 36 and 38–40 |

B. Synthesis of libraries having 2,11-Bis($L_{n-m}$)diaza-7-azadodecane[2.6]pyridinophane scaffolds, Libraries 34–39

Libraries 15–20 were each deblocked using the procedures of Example 23, thereby giving libraries 34–39 respectively. The workup was as illustrated in part A above.

| Library # | Letters (n-m) |
| --- | --- |
| 34 | 26, 29, 44, 45 and 46 |
| 35 | 20, 29, 47, 48 and 49 |
| 36 | 29–34 |
| 37 | 30, 36 and 44–49 |
| 38 | 37 and 49–52 |
| 39 | 18, 29, 36 and 38–40 |

C. Synthesis of libraries having 2,11-Bis($L_{n-m}$)diaza-7-($L_{n-m}$)azadodecane[2.6]pyridinophane scaffolds, Libraries 40–44

Libraries 21–25 were each deblocked using the procedures of Example 23, thereby giving libraries 40–44 respectively. The workup was as illustrated in part A above.

| Library # | Letters (n-m) |
| --- | --- |
| 40 | 29, 41, 42 and 44–46 |
| 41 | 29, 41, 42 and 47–49 |
| 42 | 11, 26, 29, 30, 44, 45 and 48 |
| 43 | 31 and 49–54 |
| 44 | 29, 30 and 44–48 |

EXAMPLE 27

General procedures for library synthesis via treatment of preexisting library, synthesis of Libraries 45, 46 and 47

A library selected from Library 33, 39 or 44 (0.5 mmol), 8 mL of MeOH and 4 mL of concentrated aqueous NaOH was stirred at rt for 1 day. Acetic acid (2 mL) was added to destroy the excess NaOH. The mixture was concentrated to dryness under vacuum, and the residue was triturated with MeOH to give the corresponding acetate libraries as white foams in 95–98% yields.

| Starting Library | Final Library |
| --- | --- |
| 33 | 45 |
| 39 | 46 |
| 44 | 47 |

EXAMPLE 28

General procedures for library synthesis via treatment of preexisting library, synthesis of Libraries 48, 49 and 50

A mixture of guanidine chloride (202 mg, 2.1 mmol) and sodium methoxide (120 mg, 2.1 mmol) in MeOH (10 mL) was stirred at rt for 2 h. The solvent was evaporated giving the neutralized guanidine. The neutral guanidine was mixed with a library selected from Library 33, 39 or 27 (0.7 mmol) in DMF (10 mL) and was stirred at 80° C. for 1 day. The solvent was evaporated, and the residue was triturated with MeOH. The MeOH solution was saturated with HCl (g), and the solution was concentrated to give the hydrochloride salt of the corresponding library as white foam in 95–98% yields.

| Starting Library | Final Library |
| --- | --- |
| 33 | 48 |
| 39 | 49 |
| 27 | 50 |

EXAMPLE 29

N,N-Di-(2-hydroxymethyl-pyridine-6-methyl)-N-2-nitrobenzenesulfonyl amine

A solution of diethyl azodicarboxylate (DEAD) (18.8 g, 0.108 mol) in anhydrous THF (100 mL) was added dropwise to a mixture of 2,6-pyridinedimethanol (Aldrich) (16.7 g, 0.12 mol) and $PPh_3$ (28.3 g, 0.108 mol) in anhydrous THF (200 mL) at rt. The resulting solution was stirred at rt for 30 min. 2-Nitrobenzensulfonamide (Aldrich) (8.1 g, 0.04 mol) in anhydrous THF (200 mL) was added dropwise to the above stirred solution very slowly. The resulting solution was stirred at rt overnight. The solvent was evaporated, and the residue was dissolved in $CHCl_3$. The solution was washed with water to remove excess starting material. The organic phase was dried ($Na_2SO_4$) and concentrated. The residue was purified by flash chromatography on a silica gel column using 50:1 and 30:1 $CH_2Cl_2$—MeOH as eluents to give 6.01 g (34%) of compound the title compound as a white foam.

$^1$H NMR ($CDCl_3$) δ 4.35 (b, 2H, ex $D_2O$), 4.49 (s, 4H), 4.61 (s, 4H), 7.02 (d, 2H, J=7.4 Hz), 7.06 (d, 2H, J=7.4 Hz), 7.43–7.63 (m, 5H), 7.94 (d, 1H, J=7.3 Hz). $^{13}$C NMR ($CDCl_3$) δ 52.89, 63.97, 119.47, 120.96, 124.28, 130.86, 131.90, 133.47, 133.81, 137.52, 147.75, 154.40, 159.17. HRMS (FAB) m/z 577.0167 $(M+Cs)^+$ ($C_{20}H_{20}N_4O_6SCs$ requires 577.0158). Anal. Calcd for $C_{20}H_{20}N_4O_6S$: C, 54.04; H, 4.54; N, 12.61. Found: C, 54.36; H, 4.70; N, 12.67.

EXAMPLE 30

N,N-Di-(2-tosylmethyl-pyridine-6-methyl)-N-2-nitrobenzene-sulfonyl amine

A solution of tosyl chloride (1.72 g, 9.0 mmol) in THF (20 mL) was added dropwise into a mixture of N,N-Di-(2-hydroxymethyl-pyridine-6-methyl)-N-2-nitrobenzenesulfonyl amine (1.05 g, 2.25 mmol) and NaOH (0.54 g, 13.5 mmol) in THF (15 mL) and $H_2O$ (15 mL) at 0° C. The resulting solution was stirred at rt for 3 h. The reaction mixture was poured onto a mixture of ice (30 g) and hydrochloric acid solution (2 mL, 37%). The resulting solution was extracted with $CHCl_3$ and the combined organic phase was washed with $H_2O$, 5% aqueous $NaHCO_3$, and $H_2O$. After drying ($Na_2SO_4$), the organic solution was concentrated. The residue was purified by flash chromatography on a silica gel column using $CH_2Cl_2$ and then 100:1 $CH_2Cl_2$—MeOH as eluents to give 1.51 g (89%) of the title compound as a white foam.

$^1$H NMR ($CDCl_3$) δ 2.45 (s, 6H), 4.62 (s, 4H), 4.90 (s, 4H), 7.19 (m, 4H), 7.35 (d, 4H, J=8.2 Hz), 7.53–7.62 (m, 5H), 7.80 (d, 4H, J=8.3 Hz), 7.98 (d, 1H, J=8.4 Hz). $^{13}$C NMR ($CDCl_3$) δ 21.64, 52.67, 71.54, 120.84, 122.18, 123.99, 127.72, 127.98, 130.03, 131.04, 131.65, 132.77, 133.60, 133.79, 137.71, 145.28, 147.89, 153.24, 155.54. HRMS (FAB) m/z 885.0345 $(M+Cs)^+$ ($C_{34}H_{32}N_4O_{10}S_3Cs$ requires 885.0335). Anal. Calcd for $C_{34}H_{32}N_4O_{10}S_3$: C, 54.25; H, 4.29; N, 7.45. Found: C, 54.10; H, 4.43; N, 7.49.

EXAMPLE 31

5-(N-t-Boc)-amino-1-pentanol

A solution of $(t-Boc)_2O$ (21.8 g, 100 mmol) in anhydrous THF (100 mL) was added to a solution of 5-aminopentan-1-ol (10.3 g, 100 mmol) and $Et_3N$ (30.3 g, 300 mmol) in anhydrous THF (20 mL) at 0° C. The resulting solution was stirred at rt overnight. The solvent was evaporated, and the residue was dissolved in $CHCl_3$. The solution was washed with brine, dried ($Na_2SO_4$), and concentrated. The residue was purified by flash chromatography on a silica gel column using $CH_2Cl_2$ and then 20:1 $CH_2Cl_2$—MeOH as eluents to give 19.3 g (95%) of the title compound as a pale yellow oil.

$^1$H NMR ($CDCl_3$) δ 1.50–1.80 (m, 6H), 2.57–2.85 (m, 8H), 3.85 (s, 4H), 3.94 (s, 2H), 3.95 (s, 2H), 7.08 (d, 2H, J=7.4 Hz), 7.57 (d, 2H, J=7.5 Hz). $^{13}$C NMR ($CDCl_3$) δ 26.04, 26.76, 26.98, 47.51, 47.76, 47.96, 48.08, 49.27, 53.84, 54.06, 120.48, 120.69, 136.73, 157.86, 158.15, 158.84. HRMS (FAB) m/z 369.2758 $(M+H)^+$ ($C_{21}H_{33}N_6$ requires 369.2767).

EXAMPLE 32

N1-(2-Nitrobenzenesulfonyl)-1,4-diaminobutane

A solution of 2-nitrobenzenesulfonyl chloride (44.2 g, 200 mmol) in dry $CH_2Cl_2$ (200 mL) was added dropwise to a solution of 1,4-butanediamine (Aldrich) (53.0 g, 600 mmol) and $Et_3N$ (80 mL) in dry $CH_2Cl_2$ (300 mL) at 0° C. The resulting solution was stirred at rt for 3 h. The solvent was evaporated and the residue was dissolved in $H_2O$/$CHCl_3$. The organic phase was separated and the aqueous phase was extracted with $CHCl_3$. The combined organic phase was washed with brine, dried ($Na_2SO_4$), and concentrated. The residue was purified by flash chromatography on a silica gel column using 2:1 $CH_2Cl_2$—MeOH as an eluent to give 39.81 g (73%) of the title compound as a yellow solid.

$^1$H NMR ($CDCl_3$) δ 1.43–1.63 (m, 4H), 2.68 (t, 2H, J=6.0 Hz), 3.07 (t, 2H, J=6.4 Hz), 3.12 (b, 3H, ex $D_2O$), 7.68–7.82 (m, 3H), 8.08–8.12 (m, 1H). HRMS (FAB) m/z 274.0869 $(M+H)^+$ ($C_{10}H_{16}N_{13}O_4S$ requires 274.0862). Anal. Calcd for $C_{10}H_{15}N_{13}O_4S$: C, 43.94; H, 5.53; N, 15.38. Found: C, 44.16; H, 5.47; N, 15.60.

EXAMPLE 33

N1-(2-Nitrobenzenesulfonyl)-N4-t-Boc-1,4-diaminobutane

A solution of $(t-Boc)_2O$ (3.63 g, 16.7 mmol) in anhydrous THF (15 mL) was added to a solution of N1-(2-nitrobenzenesulfonyl)-1,4-diaminobutane (3.05 g, 11.1 mmol) and $Et_3N$ (3.36 g, 33.3 mmol) in anhydrous THF (30 mL) at 0° C. The resulting solution was stirred at rt overnight. The solvent was evaporated and the residue was dissolved in $CHCl_3$. The solution was washed with $H_2O$, dried ($Na_2SO_4$) and concentrated. The residue was purified by flash chromatography on a silica gel column using $CH_2Cl_2$ and then 100:1 $CH_2Cl_2$—MeOH as eluents to give 4.08 g (99%) of the title compound as a yellow solid.

$^1$H NMR ($CDCl_3$) δ 1.37 (s, 9H), 1.44–1.50 (m, 4H), 3.00–3.07 (m, 4H), 4.73 (b, 1H), 5.52 (b, 1H, ex $D_2O$), 7.68–7.80 (m, 3H), 8.04–8.08 (m, 1H). HRMS (FAB) m/z 396.1215 $(M+Na)^+$ ($C_{15}H_{23}N_3O_6SNa$ requires 396.1205). Anal. Calcd for $C_{15}H_{23}N_3O_6S$: C, 48.24; H, 6.21; N, 11.26. Found: C, 48.25; H, 6.05; N, 11.31.

EXAMPLE 34

N1-[N-(t-Boc)-4-aminobutan-1-yl]-N1-(2-nitrobenzenesulfonyl)-N4-(t-Boc)-1,5-diaminopentane A solution of DEAD (3.66 g, 21.0 mmol) in anhydrous THF (100 mL) was added dropwise to a solution of 5-(N-t-Boc)-amino-1-pentanol (4.27 g, 21.0 mmol), N1-(2-nitrobenzenesulfonyl)-N4-t-Boc-1,4-diaminobutane (7.14 g, 19.1 mmol) and $PPh_3$ (5.52 g, 21.0 mmol) in anhydrous THF (200 mL) at rt. The resulting solution was stirred at rt for 2 h. The solvent was evaporated and the residue was dissolved in anhydrous diethyl ether. The solution was refrigerated overnight and filtered. The filtrate was concentrated and the residue was purified by flash chromatography on a silica gel column using 2:1 and 1:1 hexanes-EtOAc as eluents to give 9.95 g (93%) of the title compound as a yellow solid.

¹H NMR (CDCl₃) δ 1.20–1.62 (m, 28 H), 3.01–3.12 (m, 4H), 3.23–3.31 (m, 4H), 4.58 (b, 2H), 7.57–7.70 (m, 3H), 7.93–8.03 (m, 1H). ¹³C NMR (CDCl₃) δ 23.66, 25.47, 27.16, 27.77, 28.43, 29.53, 33.93, 40.23, 47.08, 47.29, 79.13, 124.14, 130.5.8, 131.69, 133.50, 148.02, 156.09. HRMS (FAB) m/z 691.1757 (M+Cs)⁺ ($C_{25}H_{42}N_4O_8SCs$ requires 691.1778).

EXAMPLE 35

N1-(N-4-Aminobutan-1-yl)-N1-(2-nitrobenzenesulfonyl)-1,5-diaminopentane·2HCl

A solution of N1-[N-(t-Boc)-4-aminobutan-1-yl]-N1-(2-nitrobenzenesulfonyl)-N4-(t-Boc)-1,5-diaminopentane (1.85 g, 3.31 mmol) and TFA (35 mL) in CH₂Cl₂ (5 mL) was stirred at rt for 5 h. The solvent was evaporated and the residue was dissolved in MeOH-HCl (14%). The resulting solution was evaporated under high vacuum to give 1.20 g (92%) of the title compound (2×HCl salt) as a yellow foam.

¹H NMR (CD₃OD) δ 1.35–1.71 (m, 10H), 2.87–2.96 (m, 4H), 3.30–3.39 (m, 4H), 7.78–7.85 (m, 3H), 8.01–8.06 (m, 1H). HRMS (FAB) m/z 359.1744 (M+H)⁺ ($C_{15}H_{27}N_4O_4S$ requires 359.1753).

EXAMPLE 36

N1-(2-Nitrobenzenesulfonyl)-1,7-diaminoheptane

The title compound was synthesized as illustrated in Example 32 above from 1,7-diaminoheptane (2.60 g, 20 mmol), 2-nitrobenzenesulfonyl chloride (2.2 g, 10 mmol) in the presence of Et₃N (4 mL). The product was purified by flash chromatography on a silica gel column using 200:1 CH₂Cl₂—MeOH and then 150:1 MeOH-30% NH₄OH as eluents to give 2.10 g (68%) of the title compound as a yellow oil.

¹H NMR (CDCl₃) δ 1.10–1.40 (m, 10H), 2.51 (t, 2H, J=6.8 Hz), 2.92 (t, 2H, J=7.1 Hz), 3.35 (b, 3H, ex D₂O), 7.58–7.66 (m, 3H), 7.95–7.98(m, 1H). ¹³C NMR (CDCl₃) δ 26.31, 26.52, 28.70, 29.41, 32.91, 41.47, 43.42, 124.96, 130.76, 132.65, 133.57, 147.92. HRMS (FAB) m/z 316.1338 (M+H)⁺ ($C_{13}H_{22}N_3O_4S$ requires 316.1331). Anal. Calcd for $C_{13}H_{21}N_3O_4S·H_2O$: C, 46.82; H, 6.90; N, 12.61. Found: C, 46.74; H, 6.79; N, 12.68.

EXAMPLE 37

N1-(2-Nitrobenzenesulfonyl)-N7-t-Boc-1,7-diaminoheptane

The title compound was synthesized as illustrated in Example 33 above using N1-(2-nitrobenzenesulfonyl)-1,7-diaminoheptane (5.5 g, 17.9 mmol), (t-Boc)₂O (5.0 g, 23.3 mmol) in the presence of Et₃N (7.06 g, 70 mmol). The product was purified by flash chromatography on a silica gel column using CH₂Cl₂ and then 50:1 CH₂Cl₂—MeOH to give 6.90 g (93%) of the title compound as a yellow solid.

¹H NMR (CDCl₃) δ 1.23–1.53 (m, 19H), 3.00–3.11 (m, 4H), 4.51 (b, 1H), 5.31 (t, 1H, J=5.7 Hz, ex D₂O), 7.70–7.86 (m, 3H), 8.09–8.13 (m, 1H). ¹³C NMR (CDCl₃) δ 26.30, 26.47, 28.35, 28.50, 29.41, 29.85, 40.46, 43.76, 78.91, 125.26, 130.93, 132.81, 133.62, 148.03, 156.08. HRMS (FAB) m/z 416.1842 (M+H)⁺ ($C_{18}H_{30}N_3O_6S$ requires 416.1855). Anal. Calcd for $C_{18}H_{29}N_3O_6S·H_2O$: C, 52.03; H, 7.04; N, 10.12. Found: C, 52.17; H, 6.97; N, 10.25.

EXAMPLE 38

N1-[N-(t-Boc)-4-aminopentan-1-yl]-N1-(2-nitrobenzenesulfonyl)-N4-(t-Boc)-1,7-diaminoheptane The title compound was synthesized as illustrated in Example 34 above using N1-(2-nitrobenzenesulfonyl)-N7-t-Boc-1,7-diaminoheptane (1.21 g, 2.97 mmol), 5-(N-t-Boc)-amino-1-pentanol (0.60 g, 2.97 mmol), PPh₃ (0.78 g, 2.97 mmol) and DEAD (0.52 g, 2.97 mmol). The product was purified by flash chromatography on a silica gel column using CH₂Cl₂ and then 100:1 CH₂Cl₂—MeOH as eluents to give 1.25 g (70%) of the title compound as a yellow oil.

¹H NMR (CDCl₃) δ 1.26–1.58 (m, 34 H), 3.02–3.10 (m, 4H), 3.21–3.30 (m, 4H), 4.53 (b, 2H), 7.55–7.70 (m, 3H), 7.97–8.03 (m, 1H). HRMS (FAB) m/z -601.3287 (M+H)⁺ ($C_{28}H_{49}N_4O_8S$ requires 601.3271). Anal. Calcd for $C_{28}H_{48}N_4O_8S·H_2O$: C, 55.97; H, 8.06; N, 9.33. Found: C, 55.83; H, 7.88; N, 9.60.

EXAMPLE 39

N1-(N-4-aminopentan-1-yl)-N1-(2-nitrobenzenesulfonyl)-N4-1,7-diaminoheptane·2HCl A solution of N1-[N-(t-Boc)-4-aminopentan-1-yl]-N1-(2-nitrobenzenesulfonyl)-N4-(t-Boc)-1,7-diaminoheptane (1.15 g, 1.90 mmol) and TFA (20 mL) in CH₂Cl₂ (5 mL) was stirred at rt for 5 h. The solvent was evaporated and the residue was dissolved in MeOH-HCl (14%). The resulting solution was evaporated under high vacuum to give 0.81 g (90%) of the title compound as a yellow foam.

¹H NMR (DMSO-d₆) δ 1.12–1.21 (m, 8H), 1.35–1.56 (m, 8H), 2.66–2.73 (m, 4H), 3.18–3.26 (m, 4H), 7.82–8.03 (m 10H, 6H ex D₂O) ; MS (ESI) m/z 401 (M+H)⁺ ($C_{19}H_{32}N_4O_4S$ requires 401).

EXAMPLE 40

Synthesis of bridge segments having Formula I

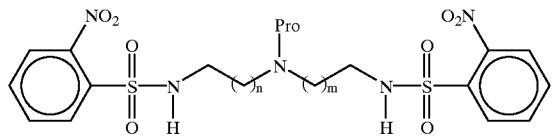

Formula I

| Section | n | m | Pro |
|---|---|---|---|
| A | 1 | 2 | t-Boc |
| B | 1 | 2 | o-nitrobenzenesulfonyl |
| C | 2 | 3 | t-Boc |
| D | 2 | 3 | o-nitrobenzenesulfonyl |
| E | 3 | 4 | o-nitrobenzenesulfonyl |
| F | 4 | 6 | o-nitrobenzenesulfonyl |

A. N1-[N-(2-nitrobenzenesulfonyl)-2-aminoethyl-1-yl]-N1-t-Boc-N3-(2-nitrobenzenesulfonyl)-1,3-diaminopropane A solution of 2-nitrobenzenesulfonyl chloride (Aldrich, 15.2 g, 68.2 mmol, 2.33 eq) in dichloromethane (90 mL) was added dropwise to a stirred solution of N1-[(t-Boc)-2-aminoethyl]-1,4-diaminopropane (6.35 g, 29.2 mmol) and triethylamine (24 mL) in dichloromethane (90 mL) at 0° C. The resulting reaction mixture was allowed to warm to room temperature and stirred for 1 hour. The mixture was diluted with chloroform and washed with water and brine. The organic phase was dried (Na₂SO₄) and the solvent was evaporated under reduced pressure. The residue was purified by flash chromatography on a silica gel column (20 cm×5 cm). Elution with hexanes:ethyl acetate (2:1 and 1:1, v/v) afforded 11.5 g (67%) of the title compound as a pale yellow sticky oil.

TLC: Rf 0.52; hexanes:ethyl acetate; 1:2, v/v; silica gel. $^1$H NMR (CDCl$_3$) δ 1.40 (s, 9H), 1.56–1.75 (m, 2H), 2.98–3.10 (m, 2H), 3.14–3.36 (m, 6H), 5.60 (bs, 1H, disappeared in D$_2$O), 6.20 (bs, 1H, disappeared in D$_2$O), 7.66–7.88 (m, 6H), 8.02–8.13 (m, 2H). $^{13}$C NMR (CDCl$_3$) δ 23.25, 40.68, 42.43, 44.18, 45.17, 46.89, 80.64, 125.32, 130.07, 132.94, 133.13, 133.99, 147.85, 156.07. Mass spectrum (HRFAB), m/z 720.039 (M+Cs)$^+$ (C$_{22}$H$_{29}$N$_5$O$_{10}$S$_2$Cs requires 720.041).

B. N1-[N-(2-nitrobenzenesulfonyl)-2-aminoethyl-1-yl]-N1-(2-nitrobenzenesulfonyl)-N3-(2-nitrobenzenesulfonyl)-1,3-diaminopropane A solution of 2-nitrobenzenesulfonyl chloride (69.8 g, 31.5 mmol) in anhydrous CH$_2$Cl$_2$ (200 mL) was added dropwise to a stirred solution of N-(2-aminoethyl)-1,3-propanediamine (11.7 g, 10 mmol) and Et$_3$N (50.5 g, 0.50 mol) at 0° C. The resulting reaction mixture was stirred at rt overnight. The solvent was evaporated and the residue was dissolved in H$_2$O-CHCl$_3$. The organic phase was separated and the aqueous phase was extracted with CHCl$_3$. The combined organic phase was washed with 5% aqueous NaHCO$_3$ and then brine. After drying (Na$_2$SO$_4$), the organic solution was concentrated. The residue was purified by flash chromatography on a silica gel column using 4:1, 1:1 and 1:4 EtOAc-hexanes to give 5.84 g (87%) of the title compound as a yellow foam.

$^1$H NMR (CDCl$_3$) δ 1.84–1.95 (m, 4H), 3.17 (t, 2H, J=6.4 Hz), 3.29 (t, 2H, J=6.4 Hz), 3.0–3.54 (m, 4H), 7.25–7.89 (m, 9H), 8.05–8.13 (m, 3H). HRMS (FAB) m/z 804.9637 (M+Cs)$^+$ (C$_{23}$H$_{24}$N$_6$O$_{12}$S$_3$Cs requires 804.9669).

C. N1-[N-(2-nitrobenzenesulfonyl)-3-aminopropan-1-yl]-N1-t-Boc-N4-(2-nitrobenzenesulfonyl)-1,4-diaminobutane A solution of 2-nitrobenzenesulfonyl chloride (Aldrich, 5.32 g, 24 mmol, 2.4 eq) in dichloromethane (30 mL) was added dropwise to a stirred solution of N1-[t-Boc(3-aminopropyl)]-1,4-diaminobutane (2.45 g, 10 mmol) (prepared as per the reported procedures of M. C. O'Sullivan, D. M. Dalrymple, Tet. Lett. 1995, 36, 345) and triethylamine (8 mL) in dichloromethane (30 mL) at 0° C. The resulting reaction mixture was allowed to warm to room temperature and further stirred for 1 hour. The mixture was diluted with chloroform and washed with water and brine. The organic phase was dried (Na$_2$SO$_4$) and the solvent was evaporated under reduced pressure. The residue was purified by flash chromatography on a silica gel column (20 cm×3 cm). Elution with hexanes:ethyl acetate (2:1 and 1:1, v/v) afforded 5.62 g (91%) of the title compound as a pale yellow sticky oil.

TLC: Rf 0.57; hexanes-ethyl acetate; 1:2, v/v; silica gel. $^1$H NMR (CDCl$_3$) δ 1.36 (s, 9H), 1.40–1.52 (m, 4 H), 1.58–1.74 (m, 2H), 2.98–3.25 (m, 8H), 5.45 (b-s, 1H, disappeared in D$_2$O), 6.31 (bs, 1H, disappeared in D$_2$O), 7.65–7.85 (m, 6H), 8.00–8.11 (m, 2H). $^{13}$C NMR (CDCl$_3$) δ 25.37, 26.87, 28.35, 40.81, 43.45, 46.39, 79.92, 125.18, 125.33, 130.78, 130.94, 132.77, 132.92, 133.51, 133.79, 148.02, 156.00. Mass spectrum (HRFAB), m/z 748.075 (M+Cs)$^+$, (C$_{24}$H$_{33}$N$_5$O$_{10}$S$_2$Cs requires 748.072).

D. N1-[N-(2-nitrobenzenesulfonyl)-3-aminopropan-1-yl]-N1-(2-nitrobenzenesulfonyl)-N4-(2-nitrobenzenesulfonyl)-1,4-diaminobutane The title compound was synthesized as per the procedures in Section B using spermidine for the starting material.

E. N1-[N-(2-nitrobenzenesulfonyl)-4-aminobutan-1-yl]-N1-(2-nitrobenzenesulfonyl)-N4-(2-nitrobenzenesulfonyl)-1,5-diaminopentane A mixture of N1-(N-4-aminobutan-1-yl)-N1-(2-nitrobenzenesulfonyl)-1,5-diaminopentane·2HCl and K$_2$CO$_3$ (4.0 g, 28.9 mmol) in DMF (50 mL) and CH$_3$CN (100 mL) was stirred at rt for 1 h. The solution was cooled to 0° C. and a solution of 2-nitrobenzenesulfonyl chloride (1.41 g, 6.35 mmol) was added dropwise. The resulting reaction mixture was stirred at rt overnight. The solvent was evaporated and the residue was dissolved in H$_2$O/CHCl$_3$. The organic phase was separated and the aqueous phase was extracted with CHCl$_3$. The combined organic phase was washed with brine, dried (Na$_2$SO$_4$), and concentrated. The residue was purified by flash chromatography on a silica gel column using 5:1, 2:1 and 1:1 hexanes-EtOAc as eluents to give 1.57 g (71%) of the title compound as a yellow foam.

$^1$H NMR (CDCl$_3$) δ 1.15–1.22 (m, 2H), 1.46 (m, 8H), 2.96–3.05 (m, 4H), 3.11–3.18 (m, 4H), 5.46–5.56 (m, 2H), 7.55–8.04 (m, 12H). $^{13}$C NMR (CDCl$_3$) δ 23.34, 25.24, 26.58, 27.67, 28.94, 43.20, 43.54, 47.13, 47.49, 124.19, 125.30, 130.18, 130.84, 132.09, 133.04, 133.29, 133.93, 147.93. MS (ESI) m/z 751 (M+Na)$^+$ (C$_{27}$H$_{32}$N$_6$O$_{12}$S$_3$Na requires 751).

F. N1-[N-(2-nitrobenzenesulfonyl)-5-aminopentane-1-yl]-N1-(2-nitrobenzenesulfonyl)-N4-(2-nitrobenzenesulfonyl)-1,7-diaminoheptane The title compound was synthesized as per the procedures illustrated in section E above from N1-(N-4-aminopentan-1-yl)-N1-(2-nitrobenzenesulfonyl)-N4-1,7-diaminoheptane·2HCl (7.0 g, 14.8 mmol) and 2-nitrobenzenesulfonyl chloride (6.90 g, 31.14 mmol) in the presence of K$_2$CO$_3$ (21.5 g, 155.7 mmol). The product was purified by flash chromatography on a silica gel column using 200:1 CH$_2$Cl$_2$—MeOH as an eluent to give 8.81 g (77%) of the title compound as a yellow oil.

$^1$H NMR (CDCl$_3$) δ 1.22–1.31 (m, 8H), 1.46–1.56 (m, 8H), 2.96–3.11 (m, 4H), 3.22 (t, 4H, J=7.8 Hz), 5.26 (b, 2H), 7.68–8.15 (m, 12 H). HRMS (FAB) m/z 903.0892 (M+Cs)$^+$ (C$_{30}$H$_{38}$N$_6$O$_{12}$S$_3$Cs requires 903.0764).

EXAMPLE 41

General procedure for synthesis of macrocyclic scaffolds of formula II

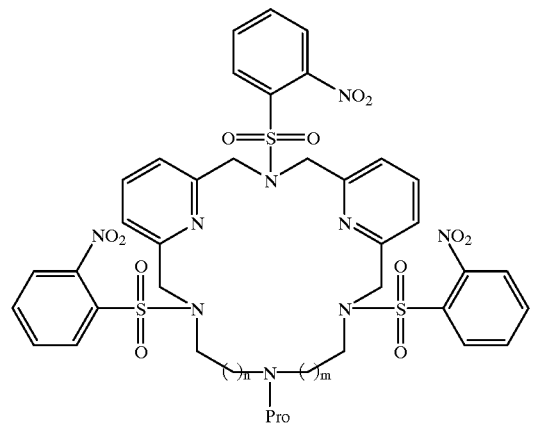

Formula II

| Section | Scaffold | n | m | Pro |
|---|---|---|---|---|
| A | 41-A | 1 | 2 | t-Boc |
| B | 41-B | 1 | 2 | 2-nitro-benzenesulfonyl |
| C | 41-C | 2 | 3 | L-Boc |

-continued

General procedure for synthesis of macrocyclic scaffolds of formula II

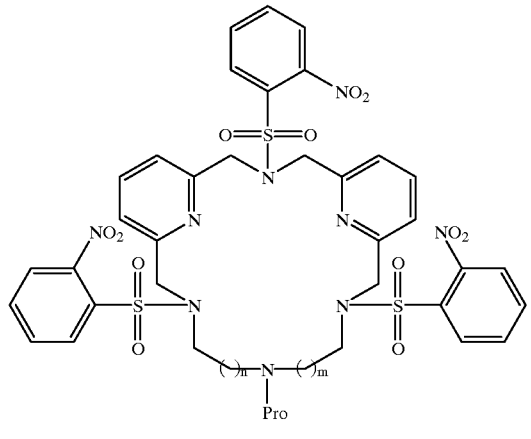

Formula II

| Section | Scaffold | n | m | Pro |
|---|---|---|---|---|
| D | 41-D | 2 | 3 | 2-nitro-benzenesulfonyl |
| E | 41-E | 3 | 4 | 2-nitro-benzenesulfonyl |
| F | 41-F | 4 | 6 | 2-nitro-benzenesulfonyl |

A. Scaffold 41-A

A mixture of compound N,N-Di-(2-tosylmethyl-6-methylene pyridine)-N-2-nitrobenzenesulfonyl amine (7.0 g, 9.3 mmol), compound N1-[N-(2-nitrobenzenesulfonyl)-2-aminoethyl-1-yl]-N1-t-Boc-N3-(2-nitrobenzenesulfonyl)-1,3-diaminopropane (5.75 g, 9.3 mmol) and anhydrous $Cs_2CO_3$ (12.12 g, 37.2 mmol) in anhydrous DMF (450 mL) was stirred at rt overnight. The solvent was evaporated and the residue was dissolved in $H_2O$-$CHCl_3$. The organic phase was separated and the aqueous phase was extracted with $CHCl_3$. The combined organic phase was washed with brine, dried ($Na_2SO_4$), and concentrated. The residue was purified by flash chromatography on a silica gel column using 200:1 $CH_2Cl_2$—MeOH as the eluent to give 7.13 g (77%) of the title compound as a white foam.

$^1$H NMR (CDCl$_3$) δ 1.31 (s, 9H), 1.63 (b, 2H), 3.05 (t, 2H, J=5.8 Hz), 3.23–3.30 (m, 4H), 3.44–3.48 (m, 2H), 4.41 (s, 2H), 4.55 (s, 2H), 4.71 (b, 4H), 7.17–7.28 (m, 4H), 7.53–8.00 (m, 14 H). HRMS (FAB) m/z 1128.1343 (M+Cs)$^+$ ($C_{42}H_{45}N_9O_{14}S_3Cs$ requires 1128.1302). Anal. Calcd for $C_{42}H_{45}N_9O_{14}S_3 \cdot 3H_2O$: C, 48.03; H, 4.86; N, 12.01. Found: C, 47.68; H, 4.42; N, 11.90.

B. Scaffold 41-B

The title compound was synthesized as illustrated in section A above using N,N-Di-(2-tosylmethyl-6-methylene pyridine)-N-2-nitrobenzenesulfonyl amine (2.36 g, 3.13 mmol) and N1-[N-(2-nitrobenzenesulfonyl)-2-aminoethyl-1-yl]-N1-(2-nitrobenzenesulfonyl)-N3-(2-nitrobenzenesulfonyl)-1,3-diaminopropane (2.10 g, 3.13 mmol) in the presence of $Cs_2CO_3$ (4.08 g, 12.52 mmol). The product was purified by flash chromatography on a silica gel column using 100% $CH_2Cl_2$, 500:1, and 300:1 $CH_2Cl_2$/MeOH as the eluents to give 3.21 g (95%) of the title compound as a yellow foam.

$^1$H NMR (CDCl$_3$) δ 1.75 (m, 2H), 3.20–3.60 (m, 8H), 4.40 (s, 2H), 4.55 (s, 2H), 4.70 (s, 4H), 7.10–7.25 (m, 4H), 7.50–8.10 (m, 18H). MS (ESI) m/z 1081 (M+H)$^+$ ($C_{43}H_{41}N_{10}O_{16}S_4$ requires 1081).

C. Scaffold 41-C

The title compound was synthesized as illustrated in section A above using N,N-Di-(2-tosylmethyl-6-methylene pyridine)-N-2-nitrobenzenesulfonyl amine (9.16 g, 9.51 mmol), N1-[N-(2-nitrobenzenesulfonyl)-3-aminopropan-1-yl]-N1-t-Boc-N4-(2-nitrobenzenesulfonyl)-1,4-diaminobutane (5.86 g, 9.51 mmol) in the presence of $Cs_2CO_3$ (12.4 g, 38.04 mmol). The product was purified by flash chromatography on a silica gel column using 100% $CH_2Cl_2$ and then 200:1 $CH_2Cl_2$/MeOH as eluents to give 6.14 g (63%) of the title compound as a yellow foam.

$^1$H NMR (CDCl$_3$) δ 1.25 (s, 13H), 1.56 (b, 2H), 2.78–2.92 (m, 4H), 3.18 (b, 4H), 4.27 (s, 2H), 4.35 (s, 2H), 4.70 (s, 4H), 7.01–7.21 (m, 6H), 7.40–7.91 (m, 12H). $^{13}$C NMR (CDCl$_3$) δ 25.18, 25.62, 26.90, 28.34, 44.96, 46.15, 46.51, 46.83, 48.07, 52.86, 77.64, 79.39, 121.05, 121.37, 121.65, 122.21, 123.85, 124.25, 125.28, 128.21, 129.01, 130.49, 130.78, 131.61, 131.95, 132.98, 133.68, 133.91, 137.84, 147.82, 148.07, 155.18, 155.64, 155.96, 156.11. HRMS (FAB) m/z 1136.1666 (M+Cs)$^+$ ($C_{44}H_{49}N_9O_{14}S_3Cs$ requires 1136.1615).

D. Scaffold 41-D

The title compound was synthesized as illustrated in section A above using N,N-Di-(2-tosylmethyl-6-methylene pyridine)-N-2-nitrobenzenesulfonyl amine (2.28 g, 3.0 mmol) and N1-[N-(2-nitrobenzenesulfonyl)-3-aminopropan-1-yl]-N1-(2-nitrobenzenesulfonyl)-N4-(2-nitrobenzenesulfonyl)-1,4-diaminobutane (2.12 g, 3.0 mmol) in the presence of $Cs_2CO_3$ (3.90 g, 12.0 mmol). The product was purified by silica gel flash column chromatography using 100% $CH_2Cl_2$ followed by $CH_2Cl_2$:MeOH (200/1, v/v) as the eluents to give 2.46 g (74%) of the title compound as a white foam.

$^1$H NMR (CDCl$_3$) δ 1.25–1.54 (m, 4H), 1.60–1.85 (m, 2H), 2.95–3.35 (m, 8H),4.32 (s, 2H), 4.39 (s, 2H), 4.74 (s, 4H), 712–799 (m, 22H). $^{13}$C NMR (CDCl$_3$) δ 24.98, 25.56, 26.90, 45.65, 45.93, 47.61, 47.91, 53.03, 53.73, 121.10, 121.50, 121.92, 122.19, 123.88, 124.23, 130.16, 130.42, 130.67, 131.79, 132.13, 132.47, 132.66, 132.82, 133.50, 134.02, 137.88, 147.96, 155.20, 155.63, 155.82. HRMS (FAB) m/z 1241.0922 (M+Cs)$^+$ ($C_{45}H_{44}N_{10}O_{16}S_4Cs$ requires 1241.0874). Anal. Calcd for $C_{45}H_{44}N_{10}O_{16}S_4$: C, 48.72; H, 4.00; N, 12.64. Found: C, 48.64; H, 4.28; N, 12.59.

E. Scaffold 41-E

The title compound was synthesized as illustrated in section A above using N,N-Di-(2-tosylmethyl-6-methylene pyridine)-N-2-nitrobenzenesulfonyl amine (1.52 g, 2.02 mmol) and N1-[N-(2-nitrobenzenesulfonyl)-4-aminobutan-1-yl]-N1-(2-nitrobenzenesulfonyl)-N4-(2-nitrobenzenesulfonyl)-1,5-diaminopentane (1.47 g, 2.02 mmol) in the presence of $Cs_2CO_3$ (2.63 g, 8.08 mmol). The product was purified by flash chromatography on a silica gel column using 1:2, 1:1, 2:1 EtOAc/hexanes as eluents to give 1.25 g (54%) of the title compound as a yellow foam.

$^1$H NMR (CDCl$_3$) δ 1.00–1.20 (m, 2H), 1.37 (b, 8H), 3.01–3.10 (m, 4H), 3.17–3.28 (m, 4H), 4.40 (s, 4H), 4.68 (s, 2H), 4.69 (s, 2H), 7.15–7.98 (m, 22H). HRMS (FAB) m/z 1269.1258 (M+Cs)$^+$ ($C_{47}H_{48}N_{10}O_{16}S_4Cs$ requires 126.9.1187).

F. Scaffold 41-F

The title compound was synthesized as illustrated in section A above using N,N-Di-(2-tosylmethyl-6-methylene pyridine)-N-2-nitrobenzenesulfonyl amine (1.70 g, 2.26 mmol) and N1-[N-(2-nitrobenzenesulfonyl)-5-aminopentane-1-yl]-N1-(2-nitrobenzenesulfonyl)-N4-(2-nitrobenzenesulfonyl)-1,7-diaminoheptane (1.75 g, 2.26 mmol) in the presence of $CS_2CO_3$ (3.0 g, 9.3 mmol). The product was purified by flash chromatography on a silica gel column using 2:1 hexanes-EtOAc and 200:1 $CH_2Cl_2$—MeOH as eluents to give 1.07 g (40%) of the title compound as a yellow foam.

$^1$H NMR (CDCl$_3$) δ 1.09–1.42 (m, 16H), 3.05–3.12 (m, 4H), 3.24 (m, 4H), 4.42 (s, 4H), 4.65 (s, 4H), 7.15–7.27 (m, 4H), 7.53–7.68 (m, 14 H), 7.87–7.99 (m, 4H). MS (ESI) m/z 1179 (M+H)$^+$ ($C_{50}H_{55}N_{10}O_{16}S_4$ requires 1179).

EXAMPLE 42

General procedures for deprotection of scaffolds 41-A through 41-F, having Formula III

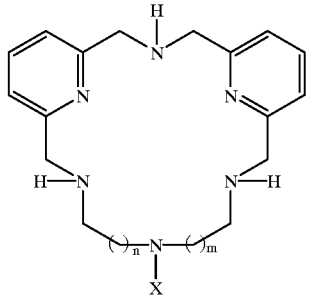

Formula III

| Section | Scaffold | n | m | X |
|---------|----------|---|---|-------|
| A | 42-A | 1 | 2 | t-Boc |
| B | 42-B | 1 | 2 | H |
| C | 42-C | 2 | 3 | t-Boc |
| D | 42-D | 2 | 3 | H |
| E | 42-E | 3 | 4 | H |
| F | 42-F | 4 | 6 | H |

A. Scaffold 42-A

To a stirred mixture of Scaffold 41A (7.09 g, 7.13 mmol) and anhydrous $K_2CO_3$ (13.8 g, 100 mmol) in anhydrous DMF (160 mL) was added thiophenol (3.3 g, 29.95 mmol). The resulting mixture was stirred at rt overnight. The solvent was evaporated, and the residue was dissolved in $H_2O$/CHCl$_3$. The organic phase was separated and the aqueous phase was extracted with CHCl$_3$. The combined organic phase was washed with brine, dried (Na$_2$SO$_4$), and concentrated. The residue was purified by flash chromatography on a silica gel column using 20:1 CH$_2$Cl$_2$/MeOH and then 30:1 MeOH-30% NH$_4$OH as eluents to give 3.10 g (99%) of the title scaffold as a pale yellow oil.

$^1$H NMR (CDCl$_3$) δ 1.44 (s, 9H), 1.77 (m, 2H), 2.64 (t, 2H, J=5.5 Hz), 2.50–2.70 (b, 3H, ex D$_2$O), 2.81 (t, 2H, J=6.2 Hz), 3.27–3.37 (m, 4H), 3.85 (s, 2H), 3.88 (s, 2H), 3.95 (s, 2H), 3.97 (s, 2H), 7.02–7.13 (m, 4H), 7.54–7.62 (m, 2H). $^{13}$C NMR (CDCl$_3$) δ 28.45, 29.01, 46.42, 46.71, 48.12, 48.31, 54.55, 54.65, 79.23, 120.77, 136.60, 136.70, 155.56, 158.90. HRMS (FAB) m/z 441.2968 (M+H)$^+$ ($C_{24}H_{37}N_6O_4$ requires 441.2978). Anal. Calcd for $C_{24}H_{36}N_6O_4 \cdot H_2O$: C, 62.84; H, 8.29; N, 18.33. Found: C, 62.70; H, 7.93; N, 18.13.

B. Scaffold 42-B

Scaffold 42-B was synthesized as illustrated above for Scaffold 42-A using Scaffold 41-B (3.13 g, 1.50 mmol) and thiophenol (2.84 g, 25.8 mmol) in the presence of $K_2CO_3$ (11.75 g, 85.01 mmol). The crude product was purified by flash chromatography on a silica gel column using CH$_2$Cl$_2$ and then 20:1 MeOH/30% NH$_4$OH as eluents to give 0.76 g (72%) of the title scaffold as a pale yellow oil.

$^1$H NMR (CD$_3$OD) δ 1.76–1.86 (m, 2H), 2.82–2.90 (m, 8H), 3.92 (s, 2H), 3.95 (s, 2H), 3.97 (s, 2H), 3.99 (s, 2H), 7.23–7.33 (m, 4H), 7.71–7.78 (m, 2H). $^{13}$C NMR (CD$_3$OD) δ 30.58, 49.87, 50.73, 56.53, 123.15, 126.52, 138.71, 139.42, 152.29, 161.29, 161.74, 161.94; MS (ESI) m/z 341 (M+H)$^+$ ($C_{19}H_{29}N_6$ requires 341).

C. Scaffold 42-C

Scaffold 42-C was synthesized as illustrated above for Scaffold 42-A using Scaffold 41-C (5.94 g, 5.81 mmol) and thiophenol (2.69 g, 24.4 mmol) in the presence of $K_2CO_3$ (10.2 g, 73.8 mmol). The product was purified by flash chromatography on a silica gel column using CH$_2$Cl$_2$ and then 30:1 MeOH-30% NH$_4$OH as eluents to give 2.66 g (98%) of the title scaffold as a pale yellow oil.

$^1$H NMR (CDCl$_3$) δ 1.33 (s, 9H), 1.45 (m, 4H), 1.68 (m, 2H), 2.54–2.61 (m, 4H), 2.95 (s, 4H, ex D$_2$O), 3.06–3.19 (m, 4H), 3.77 (s, 4H), 3.85 (s, 4H), 6.99–7.09 (m, 4H), 7.44–7.51 (m, 2H). $^{13}$C NMR (CDCl$_3$) δ 26.55, 27.13, 28.43, 29.27, 45.97, 46.78, 47.99, 48.79, 53.37, 54.74, 79.01, 120.77, 136.69, 155.58, 158.64, 158.85, 159.06. HRMS (FAB) m/z 469.3280 (M+H)$^+$ ($C_{26}H_{41}N_6O_2$ requires 469.3291).

D. Scaffold 42-D

Scaffold 42-D was synthesized as illustrated above for Scaffold 41-A using Scaffold 41-D (2.29 g, 2.0 mmol) and thiophenol (1.23 g, 11.2 mmol) in the presence of $K_2CO_3$ (4.64 g, 33.6 mmol). The product was purified by flash chromatography on a silica gel column using CH$_2$Cl$_2$ and then 10:1 MeOH-30% NH4OH as eluents to give 0.67 g (91%) of the title scaffold as a pale yellow oil.

$^1$H NMR (CDCl$_3$) δ 1.33 (s, 9H), 1.45 (m, 4H), 1.68 (m, 2H), 2.54–2.61 (m, 4H), 2.95 (s, 4H, ex D$_2$O), 3.06–3.19 (m, 4H), 3.77 (s, 4H), 3.85 (s, 4H), 6.99–7.09 (m, 4H), 7.44–7.51 (m, 2H). $^{13}$C NMR (CDCl$_3$) δ 26.55, 27.13, 28.43, 29.27, 45.97, 46.78, 47.99, 48.79, 53.37, 54.74, 79.01, 120.77, 136.69, 155.58, 158.64, 158.85, 159.06. HRMS (FAB) m/z 469.3280 (M+H)$^+$ ($C_{26}H_{41}N_6O_2$ requires 469.3291).

E. Scaffold 42-E

Scaffold 42-E was synthesized as illustrated above for Scaffold 41-A using Scaffold 41-E (1.22 g, 1.06 mmol) and thiophenol (0.61 g, 5.52 mmol) in the presence of $K_2CO_3$ (2.3 g, 16.5 mmol). After the reaction was completed, the reaction mixture was filtered to remove part of $K_2CO_3$. The solution was evaporated, and the residue was purified by flash chromatography on a silica gel column using CH$_2$Cl$_2$ and then 20:1 MeOH/30% NH$_4$OH as eluents to give 0.37 g (88%) of the title scaffold as a pale yellow oil.

$^1$H NMR (CDCl$_3$) δ 1.05–1.32 (m, 10 H), 2.31–2.41 (m, 12H, 4H ex D$_2$O), 3.61 (s, 4H), 3.73 (s, 4H), 6.86–6.99 (m, 4H), 7.27–7.39 (m, 2H). $^{13}$C NMR (CDCl$_3$) δ 36.63, 39.40, 39.74, 41.05, 41.55, 60.73, 61.07, 67.03, 89.02, 89.66, 89.87, 90.30, 132.58, 132.73, 148.75, 171.37, 171.46. HRMS (FAB) m/z 397.3093 (M+H)$^+$ (C$_{23}$H$_{37}$N$_6$ requires 397.3080).

F. Scaffold 42-F

Scaffold 42-F was synthesized as illustrated above for Scaffold 41-A using Scaffold 41-F (1.06 g, 0.899 mmol) and thiophenol (0.52 g, 4.67 mmol) in the presence of K$_2$CO$_3$ (1.93 g, 14 mmol). After the reaction was completed, the reaction mixture was filtered to remove part of K$_2$CO$_3$. The solution was evaporated and the residue was purified by silica gel flash column chromatography using CH$_2$Cl$_2$, CH$_2$Cl$_2$:MeOH (5/1, v/v) followed by MeOH:30% NH$_4$OH (20/1, v/v) as eluents to give 0.19 g (48%) of the title scaffold as a pale yellow oil.

$^1$H NMR (CDOD) δ 1.29–1.65 (m, 16H), 2.60–2.76 (m, 8H), 3.91 (s, 4H), 3.95 (s, 4H), 7.29–7.38 (m, 4H), 7.77 (t, 2H, J 7.7 Hz). $^{13}$C NMR (CDOD) δ 25.27, 27.34, 27.51, 28.41, 29.43, 29.56, 29.81, 55.15, 122.41, 138.77, 159.61, 160.01. HRMS (FAB) m/z 439.3535 (M+H)$^+$ (C$_{26}$H$_{42}$N$_6$ requires 439.3549).

EXAMPLE 43

Synthesis of Libraries based on Scaffold 42-A and 42-B having formula IV, Libraries 51–60

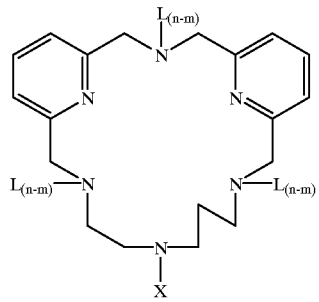

Formula IV

| Section | Library | X | L(n-m) |
|---|---|---|---|
| A | 51 | t-Boc | 18–21, 23–27 and 55 |
| B | 52 | H | 18–21, 23–27 and 55 |
| C | 53 | L$_{28}$ | 18–21, 23–27 and 55 |
| D | 54 | L$_{56}$ | 18–21, 23–27 and 55 |
| E | 55 | L$_{57}$ | 18–21, 23–27 and 55 |
| F | 56 | L$_{58}$ | 18–21, 23–27 and 55 |
| G | 57 | L$_3$ | 18–21, 23–27 and 55 |
| H | 58 | L$_{59}$ | 18–21, 23–27 and 55 |
| I | 59 | L$_1$ | 18–21, 23–27 and 55 |
| J | 60 | L$_{60}$ | 18–21, 23–27 and 55 |

A. Library 51

A solution containing equimolar amounts benzyl bromide (Br-L$_{18}$), α-bromo-m-xylene (Br-L$_{19}$), 3-fluorobenzyl bromide (Br-L$_{20}$), 3-cyanobenzyl bromide (Br-L$_{21}$), 3-chlorobenzyl bromide (Br-L$_{23}$), 3-nitrobenzyl bromide (Br-L$_{24}$), methyl 3-(bromomethyl)benzoate (Br-L$_{25}$), α'-bromo-α,α,α-trifluoro-m-xylene (Br-L$_{26}$), 3-bromobenzyl bromide (Br-L$_{27}$) and bromoacetonitrile (L$_{55}$) (total 23.25 mmol) in anhydrous CH$_3$CN (50 mL) was added to a stirred mixture of Scaffold 42-A (3.10 g, 7.045 mmol) and anhydrous K$_2$CO$_3$ (11.7 g, 84.54 mmol) in CH$_3$CN (150 mL). The resulting reaction mixture was stirred at rt for one day. The solvent was evaporated, and the residue was dissolved in H$_2$O:CHCl$_3$. The organic phase was separated and the aqueous phase was extracted with CHCl$_3$. The combined organic phase was washed with brine, dried (Na$_2$SO$_4$), and concentrated. The residue was purified by flash chromatography on a silica gel column using 200:1, 100:1 and then 20:1:MeOH as eluents to give 4.98 g (88%) of Library 51 as a yellow foam.

B. Library 52

A solution of Library 51 (4.98 g, 6.22 mmol) and TFA (50 mL) in CHCl$_3$ (15 mL) was stirred at rt overnight. The solvent was evaporated and the residue was dissolved in H$_2$O and adjusted pH to 7–8 with aqueous hydrochloric acid (37%). The solution was extracted with CHCl$_3$. The combined organic phase was washed with brine, dried (Na$_2$SO$_4$) and concentrated. The residue was purified by flash chromatography on a silica gel column using MeOH and then 30:1 MeOH:30% NH$_4$OH as eluents to give 3.98 g (91%) of Library 52 as a yellow oil.

C. Library 53

To a mixture of Library 52 (0.20 g, 0.286 mmol) and K$_2$CO$_3$ (0.60 g, 4.3 mmol) in anhydrous CH$_3$CN (10 mL) was added 2-bromoacetamide (Br-L$_{28}$) (51 mg, 0.372 mmol). The resulting mixture was stirred at rt overnight. The solvent was evaporated, and the residue was dissolved in H$_2$O/CHCl$_3$. The organic phase was separated and the aqueous phase was extracted with CHCl$_3$. The combined organic phase was washed with brine, dried (Na$_2$SO$_4$) and concentrated. The residue was purified by flash chromatography on a silica gel column using 100:1 and 20:1 CH$_2$Cl$_2$:MeOH as eluents to give 0.13 g (60%) of Library 53 as a yellow oil.

D. Library 54

Library 54 was synthesized as illustrated above for Library 53 from Library 52. Library 52 (0.21 g, 0.30 mmol) was treated with bromonitromethane (Br-L$_{56}$) (54.6 mg, 0.39 mmol, 1.3 equiv) in the presence of K$_2$CO$_3$ (0.62 g, 4.5 mmol). The product was purified by flash chromatography on a silica gel column using 100:1, 50:1:MeOH as eluents to give 73 mg (32.0%) of Library 54 as a yellow oil.

E. Library 55

A solution of Library 52 (0.28 g, 0.40 mmol) and N,N'-Bis(t-Boc)-1H-pyrazol-1-carboxamidine (to give L$_{57}$) (prepared as per Bernatowicz, M. S., et al., *Tetrahedron Lett.*, 1993, 34, 3389, Bernatowicz, M. S., et al., *J. Org. Chem.*, 1992, 57, 2497) (148 mg, 0.48 mmol, 1.2 equiv) in anhydrous THF (10 mL) was stirred at 60–70° C. for 24 h. The solvent was evaporated, and the residue was dissolved in CHCl$_3$. The resulting solution was washed with H$_2$O and brine, dried (Na$_2$SO$_4$) and concentrated. The residue was purified by flash chromatography on a silica gel column using CH$_2$Cl$_2$ and then 100:1, 30:1 CH$_2$Cl$_2$:MeOH as eluents to give 220 mg (59%) of Library 55 as a yellow foam.

F. Deblocking of Library 55, Library 56

A solution of Library 55 (0.21 g, 0.22 mmol) and TFA (2 mL) in CH$_2$Cl$_2$ (1.5 mL) was stirred at rt overnight. The solvent and excess TFA were evaporated and the residue was dissolved in H$_2$O. The pH of the resulting solution was adjusted to 7–8 with aqueous hydrochloric acid (37%), and extracted with $CHCl_3$. The combined organic phase was washed with brine, dried ($Na_2SO_4$) and evaporated under high vacuum to give a quantitative yield of Library 56 as a yellow foam.

G. Library 57

Library 52 (0.12 g, 0.17 mmol), N-bromoacetyl-N(N,N-bis-t-Boc-guanidinyl)piperazine (Br-$L_3$) (94 mg, 0.21 mmol) and $K_2CO_3$ was stirred at rt overnight. The solvent was evaporated, and the residue was dissolved in $H_2O$/$CHCl_3$. The organic phase was separated and the aqueous phase was extracted with $CHCl_3$. The combined organic phase was washed with brine, dried ($Na_2SO_4$), and evaporated under high vacuum to give a quantitative yield of Library 57.

H. Deblocking of Library 57, Library 58

A solution of Library 57 and TFA (1.4 mL) in $CH_2Cl_2$ (1 mL) was stirred at rt overnight. The solvent and excess TFA were evaporated, and the residue was dissolved in $H_2O$. The resulting solution was adjusted pH to 7–8 with aqueous hydrochloric acid (37%), and extracted with $CHCl_3$. The combined organic phase was washed with brine, dried ($Na_2SO_4$), and evaporated under high vacuum to give 123 mg (90%) of library 58 as a yellow foam.

I. Library 59

Library 59 was synthesized as illustrated above for Library 57 from library 52 (176 mg, 0.25 mmol) and 3-[N-(N,N-(bis-t-Boc)-guanidinyl]-benzylbromide (Br-$L_1$) (118 mg, 0.276 mmol) in the presence of $K_2CO_3$ (0.52 g, 3.77 mmol). The product was purified by flash chromatography on a silica gel column using 100:1 $CH_2Cl_2$:MeOH as an eluent to give 220 mg (85%) of Library 59 as a yellow foam.

J. Deblocking of Library 59, Library 60

Library 60 was synthesized as illustrated above for library 58 from library 59 (207 mg, 0.197 mmol) and TFA (1.6 mL) in $CH_2Cl_2$ (1 mL). The product was purified by flash chromatography on a silica gel column using 50:1 MeOH:30% $NH_4OH$ to give 137 mg (82%) of library 60 as a yellow foam.

EXAMPLE 44

Synthesis of Libraries based on Scaffold 42-B having formula IV with X being a substituted phenol, Libraries 52a and 61–68

A solution of Library 52 (1.0 equiv), $CH_2O$ (5 equiv) and $CH_3OH$ (3 mL/mmol of Library 52) was stirred at rt overnight. The solvent was evaporated under high vacuum. The resulting intermediate Library (52a) was dissolved in benzene (2 mL/mmol of Library 52a) and treated with a selected substituted phenol (1.3 eq). The resulting solution was refluxed for 24 h. The solvent was evaporated, and the residue was purified by preparative thin layer chromatography (PLC) or flash chromatography on a silica gel column to afford the respective library in 50–60% yields.

| Library # | Substituted phenol | X |
|---|---|---|
| 52a | | ($L_{61}$) |
| 61 | 4-methoxyphenol ($L_{62}$) | ($L_{70}$) |
| 62 | 4-methylphenol ($L_{63}$) | ($L_{71}$) |
| 63 | 4-nitrophenol ($L_{64}$) | ($L_{72}$) |
| 64 | 4-trifluoromethyl phenol ($L_{65}$) | ($L_{73}$) |
| 65 | 4-chlorophenol ($L_{66}$) | ($L_{73}$) |
| 66 | 4-bromophenol ($L_{67}$) | ($L_{74}$) |
| 67 | 2,6-dimethylphenol ($L_{68}$) | ($L_{75}$) |
| 68 | 5-chloro-8-hydroxy-quinoline ($L_{69}$) | ($L_{76}$) |

EXAMPLE 45

Synthesis of Libraries based On Scaffold 42-B having formula IV, Libraries 69–79

| Section | Library | L(n-m) |
|---|---|---|
| A | 69 | 1, 3, 8, 16 and 78 |
| B | 70 | 44, 45, 46, 11 and 29 |
| C | 71 | 11, 29, 2, 7 and 17 |
| D | 72 | 11, 29, 49, 47 and 48 |
| E | 73 | 1, 11, 29, 79 and 17 |
| F | 74 | 44, 11, 29, 49 79 |
| G | 75 | 3, 5, 46, 12 and 6 |
| H | 76 | 45, 49, 51, 53 and 50 |
| I | 77 | 3, 39, 2, 81 and 20 |
| J | 78 | 45, 39, 47, 82 and 20 |
| K | 79 | 80, 81, 83, 84 and 85 | note: isocyanate and thioisocyanate reactive functionalities give 2-substituted acetamides and 2-substituted thioacetamides respectively, upon attachment to the scaffold.

A. Preparation of Library 69

To the completely deprotected scaffold 42-B (1.0 equiv) and $K_2CO_3$ (15 equiv) in anhydrous $CH_3CN$ (10 mL) was added a solution of 3-[N-(N,N-(bis-t-Boc)-guanidinyl]-benzylbromide (Br-$L_1$), N-bromoacetyl-N(N,N-bis-t-Boc-guanidinyl)piperazine (Br-$L_3$), 2-bromo-N'-[2'-(bis-N-t-Boc)ethylguanidino]-acetamide (Br-$L_{16}$), N-Boc-N-chloroacetylpiperazine (Cl-$L_8$) and benzoic anhydride ($L_{78}$) (total 4.2 equiv) in anhydrous $CH_3CN$ (5 mL). The resulting reaction mixture was stirred at rt for 4 h. The solvent was evaporated, and the residue was dissolved in $H_2O$/$CHCl_3$. The organic phase was separated and the aqueous phase was extracted with $CHCl_3$. The combined organic phase was washed with brine, dried ($Na_2SO_4$) and concentrated. The residue was purified by silica gel flash column chromatography using $CH_2Cl_2$ and then $CH_2Cl_2$:MeOH (1/1, v/v) as eluents to give 255 mg (79%) of the title library as a yellow foam.

B. General Procedure for Deprotection, Preparation of Library 70

A solution of the t-Boc protected Library 69 (1.0 equiv) and TFA in $CH_2Cl_2$ (1 mL) was stirred at rt for 5 h. The solvent and the excess TFA were evaporated and the residue was dissolved in $CH_3OH$/HCl (14%). The resulting solution was evaporated under high vacuum to give a quantitative yield of the title library as the HCl salt. The letters attached to the scaffold are subsequently 3-guanidinylbenzyl ($L_{44}$), N-methylenecarbonyl-N-guanidinyl piperazine ($L_{45}$), N-guanidinylethyl-N-methylenecarbonyl ($L_{46}$), 2-bromomethyl Pyridine-6-methanol (Br-$L_{11}$) and benzoyl-bromide (Br-$L_{29}$).

C. Preparation of Library 71

Library 71 was synthesized as per the procedure illustrated for library 69 above using 2-bromomethyl pyridine-6-methanol (Br-$L_{11}$), benzoylbromide (Br-$L_{29}$), 3-(N-Boc)-aminobromobenzene (Br-$L_2$), N-Boc-N-chloroacetylpiperazine (Cl-$L_8$) and 2-bromo-N-[2'-(N'-t-Boc)ethylamino]-acetamide (Br-$L_{17}$). The library was purified by silica gel flash column chromatography using $CH_2Cl_2$ and then $CH_2Cl_2$:MeOH (5/1, v/v) as eluents to give 298 mg (89%) of the title library as a yellow foam.

D. Preparation of Library 72

Following the procedures illustrated in Section B above, Library 71 was deprotected to give the letters 2-bromomethyl pyridine-6-methanol (Br-$L_{11}$), benzoylbromide (Br-$L_{29}$), 2-bromo-N-[2'-(N'-t-Boc)ethylamino]-acetamide ($L_{49}$), 3-aminobenzyl ($L_{47}$) and N-methylenecarbonyl-piperazine ($L_{48}$) attached to the scaffold.

E. Preparation of Library 73

Library 73 was synthesized as per the procedure illustrated for library 69 above using 3-[N-(N,N-(bis-t-Boc)-guanidinyl]-benzylbromide (Br-$L_1$), 2-bromomethyl pyridine-6-methanol (Br-$L_{11}$), benzoylbromide (Br-$L_{29}$), 4-trifluoromethylbenzylbromide (Br-$L_{79}$), and 2-bromo-N-[2'-(N'-t-Boc)ethylamino]-acetamide (Br-$L_{17}$). The library was purified by silica gel flash column chromatography using $CH_2Cl_2$ and then $CH_2Cl_2$:MeOH (4/1, v/v) as eluents to give 271 mg (86%) of the title library as a yellow oil.

F. Preparation of Library 74

Following the procedures illustrated in Section B above, Library 73 was deprotected to give the letters 2-bromomethyl pyridine-6-methanol (Br-$L_{11}$), 3-guanidinylbenzyl ($L_{44}$) benzoylbromide (Br-$L_{29}$), 2-bromo-N-[2'-(N'-t-Boc)ethylamino]-acetamide ($L_{49}$) and 4-trifluoromethylbenzylbromide (Br-$L_{79}$) attached to the scaffold.

G. Preparation of Library 75

To the completely deprotected scaffold 42-B (1.0 equiv) and $K_2CO_3$ (15 equiv) in anhydrous $CH_3CN$ (10 mL) was added a solution of N-bromoacetyl-N(N,N-bis-t-Boc-guanidinyl)piperazine (Br-$L_3$), N-(3-chloromethylbenzoyl)-N(N,N-bis-t-Boc-guanidinyl)piperazine (Cl-$L_5$), N-(4-chloromethylbenzoyl)-N(N,N-bis-t-Boc-guanidinyl) piperazine (Cl-$L_6$), N'-(Boc)-N"-p-(chloromethyl)benzoyl ethylenediamine (Cl-$L_{12}$) and N-guanidinylethyl-N-methylenecarbonyl ($L_{46}$) (total 4.8 equiv) in anhydrous $CH_3CN$ (5 mL). The resulting reaction mixture was stirred at 50–60° C. for 24 h. The solvent was evaporated, and the residue was dissolved in $H_2O$/$CHCl_3$. The organic phase was separated and the aqueous phase was extracted with $CHCl_3$. The combined organic phase was washed with brine, dried ($Na_2SO_4$), and concentrated. The library was purified by silica gel flash column chromatography using $CH_2Cl_2$ and then $CH_2Cl_2$:MeOH (4/1, v/v) as eluents to give a quantitative yield of Library 75 as a yellow foam.

H. Preparation of Library 76

Following the procedures illustrated in Section B above, Library 75 was deprotected to give the deprotected letters N-methylenecarbonyl-N-guanidinyl piperazine ($L_{45}$), 2-bromo-N-[2'-(N'-t-Boc)ethylamino]-acetamide ($L_{49}$), N-(3-methylenebenzoyl)-piperazine ($L_{51}$), N-p-methylenebenzoyl ethylenediamine ($L_{53}$) and N-(4-methylenebenzoyl)-N-guanidinyl piperazine ($L_{50}$) attached to the scaffold.

I. Preparation of Library 77

Library 77 was synthesized as per the procedure illustrated for library 69 above using p-Methylester benzylbromide (Br-$L_{39}$), 2,5-dichlorophenyl isothiocyanate ($L_{81}$), N-bromoacetyl-N(N,N-bis-t-Boc-guanidinyl)piperazine (Br-$L_3$), 3-(N-Boc)-aminobromobenzene (Br-$L_2$) and 3-fluorobenzyl bromide (Br-$L_{20}$) to give 165 mg (47%) of the title library.

J. Preparation of Library 78

Following the procedures illustrated in Section B above, Library 77 was deprotected to give the letters 3-methoxyphenyl isocyanate ($L_{82}$), 3-aminobenzyl ($L_{47}$), N-methylenecarbonyl-N-guanidinyl piperazine ($L_{45}$), p-Methylester benzylbromide (Br-$L_{39}$) and 3-fluorobenzyl bromide (Br-$L_{20}$) attached to the scaffold.

K. Preparation of Library 79

To the completely deprotected scaffold 42-B (1.0 equiv) and $K_2CO_3$ (15 equiv) in anhydrous $CH_3CN$ (10 mL) was added a solution of 4-fluorophenyl isocyanate ($L_{80}$), 2,5-dichlorophenyl isothiocyanate ($L_{81}$), 4-trifluoromethoxyphenyl isocyanate ($L_{83}$), cyclohexyl isocyanate ($L_{84}$) and 4-ethylesterphenyl isocyanate ($L_{85}$) (total 4.2 equiv) in DMF (5 mL) and $CH_3CN$ (10 mL) and the mixture was stirred at rt for 2 h. The resulting reaction mixture was stirred at 50–60° C. for 24 h. The solvent was evaporated, and the residue was purified by silica gel flash column chromatography using $CH_2Cl_2$ and then $CH_2Cl_2$:MeOH (5/1, v/v) as eluents to give 180 mg (61.8%) of the title library as a yellow foam.

EXAMPLE 46

4-Bromopyridine-2,6-dimethanol

The title compound was synthesized via modification of Acta Chem. Scand. B42, 373, 1988. A mixture of $NaBH_4$ (6.8 g, 180 mmol), diethyl 4-bromopyridine-2,6-dicarboxylate (12.1 g, 40 mmol) in absolute EtOH (500 mL) was heated under reflux for 18 h. The solvent was removed in vacuo and the residue was treated with hot saturated aqueous $NaHCO_3$. The mixture was extracted with EtOAc, the combined organic phase was dried ($Na_2SO_4$) and evaporated. The dried material was recrystallized from EtOAc to give 7.3 g (83%) of the title compound as white crystals.

$R_f$ 0.62 (EtOAc/MeOH 20:1). $^1H$ NMR (DMSO-$d_6$, 200 MHz) δ 4.54 (d, 4 H, J=5.4 Hz), 5.55 (5, 2 H, J=5.8 Hz), 7.53 (s, 2 H). $^{13}C$ NMR (DMSO-$d_6$) δ 63.69, 118.08, 121.10, 163.19.

EXAMPLE 47

4-Piperazinylpyridine-2,6-diethyldicarboxylate

A mixture of diethyl 4-bromopyridine-2,6-dicarboxylate (14.0 g, 46 mmol) and piperazine (12.2 g, 142 mmol) in dioxane (700 mL) was refluxed for 2 days. The solid was filtered and the collected solvent was evaporated in vacuo to a residue. The residue was diluted with $CH_2Cl_2$ and washed with NaCl. The layers were separated and the aqueous phase was extracted twice with $CH_2Cl_2$. The combined organic phase was washed with brine, dried ($Na_2SO_4$) and concentrated under reduced pressure. The crude white solid was purified by silica gel flash column chromatography using $CH_2Cl_2$:MeOH (9:1, 6:4) as the eluent. Further purification by recrystallization using hexanes/EtOAc gave 12.3 g (87%) of the title compound as white crystals.

$R_f$ 0.20 (MeOH:30% $NH_4OH$, 100:1). $^1H$ NMR ($CD_3OD$) δ 1.41–1.48 (m, 6 H), 1.63–1.80 (br, 1 H), 2.99–3.04 (m, 4 H), 3.42–3.47 (m, 4 H), 4.39–4.50 (m, 4 H), 7.63 (s, 2 H). $^{13}C$ NMR ($CD_3OD$) δ 14.19, 45.53, 46.96, 62.16, 111.34, 149.25, 156.38, 165.62. HRMS (FAB) m/z 308.162 $(M+H)^+$ ($C_{15}H_{22}N_3O_4$ requires 308.161).

EXAMPLE 48

4-Piperazinylpyridine-2,6-dimethanol

Method A

A mixture of 4-Bromopyridine-2,6-dimethanol (3.2 g, 15 mmol) and piperazine (13.0 g, 150 mmol) in dioxane (200 mL) was refluxed for 4 days. The solvent was evaporated, and the residue was thouroughly dried at elevated temperature under high vacuum to remove excess piperazine. The crude solid was purified by silica gel flash column chromatography using EtOAc:MeOH (10/1–1/1, v/v) and MeOH:$NH_4OH$ (1/0–50/1, v/v) as the eluent to afford 2.9 g (86%) of the title compound as a white solid.

Mp 178.0–179.5° C. $R_f$ 0.35 (MeOH/$NH_4OH$ 50:1). $^1H$ NMR ($CD_3OD$) δ 2.88–2.98 (m, 4 H), 3.33–3.42 (m, 4 H), 4.57 (s, 4 H), 6.86 (s, 2 H). $^{13}C$ NMR ($CD_3OD$) δ 46.15, 7.72, 65.55, 104.35, 158.58, 162.11. HRMS (FAB) m/z 24.139 $(M+H)^+$ ($C_{11}H_{19}N_3O_2$ requires 224.139).

Method B

The title compound was also prepared by using the procedure illustrated in Example 46. Using 4-piperazinyl-yridine-2,6-diethyldicarboxylate (4.2 g, 14 mmol) and $NaBH_4$ (5.2 g, 137 mmol) in absolute EtOH (250 mL) afforded 1.9 g (62%) the title compound.

EXAMPLE 49

4-[N4'-(t-Boc)-piperazin-N1'-yl]pyridine-2,6-dimethanol

A solution of di-tert-butyl dicarbonate (15.0 g, 69 mmol) in THF (100 mL) was added to a stirred solution of 4-Piperazinylpyridine-2,6-dimethanol (10.8 g, 48 mmol) and $Et_3N$ (14 mL, 100 mmol) in THF:MeOH (1/2, v/v) (300 mL) at 0° C. The reaction mixture was allowed to warm to rt and stirred for 24 h. The solvent was removed in vacuo, the residue diluted with $CH_2Cl_2$ and washed with $H_2O$. The layers were separated and the aquous phase was extracted twice with $CH_2Cl_2$. The combined organic phase was washed with brine, dried ($Na_2SO_4$), and concentrated under reduced pressure. The crude product was purified by column chromatography using EtOAc:MeOH (7/3–1/9, v/v) as the eluent to give 14.3 g (92%) of the title compound as a white solid.

$R_f$ 0.70 (MeOH/$NH_4OH$ 100:1). $^1H$ NMR ($CD_3OD$) δ 1.49 (s, 9 H), 3.44–3.47 (m, 4 H), 3.55–3.58 (m, 4 H), 4.57 (s, 4 H), 6.88 (s, 2 H). $^{13}C$ NMR ($CD_3OD$) δ 28.7, 44.0, 46.9, 65.5, 81.6, 104.5, 156.4, 158.1, 162.1. HRMS (FAB) m/z 346.173 $(M+Na)^+$ ($C_{16}H_{25}N_3O_4Na$ requires 2346.174. Anal. Calcd for $C_{16}H_{25}N_3O_4$: C, 59.42; H, 7.79; N, 12.99. Found: C, 59.37; H, 7.86; N, 12.71.

EXAMPLE 50

4-[N4'-(t-Boc)-piperazin-N1'-yl]-pyridine-2,6-dimethanolditosylate

4-[N4'-(t-Boc)-piperazin-N1'-yl]pyridine-2,6-dimethanol (3.9 g, 12 mmol) was dissolved in a mixture of THF (80 mL) and NaOH (14 mL, 4.3 M in $H_2O$). The reaction mixture was cooled to 0° C. and p-toluenesulfonyl chloride (5.5 g, 29 mmol) was added slowly. The reaction mixture was allowed to warm to rt and stirred for 24 h. The solvent was evaporated, and the residue was diluted with $CH_2Cl_2$ and washed with $H_2O$. The layers were separated and the aquous phase was extracted twice with $CH_2Cl_2$. The combined organic phase was washed with brine, dried ($Na_2SO_4$) and concentrated under reduced pressure. The crude product was purified by silica gel flash column chromatography using hexanes:EtOAc (8:2–6:4, v/v) as the eluent to give 6.0 g (79%) of the title compound as a white solid.

$R_f$ 0.52 (hexanes/EtOAc 3:7). $^1H$ NMR ($CDCl_3$) δ 1.49 (s, 9 H), 2.44 (s, 6 H), 3.30–3.32 (m, 4 H), 3.53–3.56 (m, 4 H), 4.93 (s, 4 H), 6.63 (s, 2 H), 7.31–7.33 (m, 4 H), 7.78–7.80 (m, 4 H). $^{13}C$ NMR ($CDCl_3$) δ 21.6, 28.4, 45.8, 71.7, 80.4, 105.2, 128.0, 130.0, 132.8. HRMS (FAB) m/z 764.108 $(M+Cs)^+$ ($C_{30}H_{37}N_3O_8S_2Cs$ requires 764.107). Anal. Calcd for $C_{30}H_{37}N_3O_8S_2$: C, 57.04; H, 5.90; N, 6.65. Found: C, 56.77; H, 6.06; N, 6.41.

EXAMPLE 51

N1,N6, N10-Tris(2-nitrobenzenesulfonyl) spezmidine

A solution of 2-nitrobenzenesulfonyl chloride (50.4 g, 227 mmol) in $CH_2Cl_2$ (150 mL) was added to a stirred solution of spermidine (10.0 g, 69 mmol) and $Et_3N$ (34 mL, 244 mmol) in $CH_2Cl_2$ (500 mL) at 0° C. The reaction mixture was allowed to warm to rt and stirred for 24 h. The solvent was removed in vacuo, and the residue was diluted with $CH_2Cl_2$ and washed with $H_2O$. The layers were separated and the aquous phase was extracted with $CH_2Cl_2$. The combined organic phase was washed with brine, dried ($Na_2SO_4$) and concentrated under reduced pressure. The crude product was purified by silica gel flash column chromatography using hexanes:EtOAc (1:1–9:1, v/v) as the eluent to afford 42.2 g (88%) of the title compound as a pale green foam.

$R_f$ 0.33 (hexanes/EtOAc 2:8). $^1H$ NMR ($CDCl_3$) δ 1.56–1.61 (m, 4 H), 1.84–1.91 (m, 2 H), 3.11–3.23 (m, 4 H), 3.28–3.43 (m, 4 H), 5.34–5.38 (m, 1 H), 5.63–5.69 (m, 1 H), 7.64–7.92 (m, 9 H), 8.02–8.06 (m, 1 H), 8.13–8.18 (m, 2 H). $^{13}C$ NMR ($CDCl_3$) δ 25.2, 26.6, 28.9, 40.8, 43.1, 45.1, 47.5, 124.3, 125.4, 127.6, 130.6, 131.0, 132.1, 132.8, 133.0, 133.4, 133.8, 134.1, 148.0. HRMS (FAB) m/z 832.995 $(M+Cs)^+$ ($C_{25}H_{28}N_6O_{12}S_3Cs$ requires 832.998).

EXAMPLE 52

N1,N3,N6-Tris(2-nitrobenzenesulfonyl)-1,6-diamino-3-azahexane

The title compound was synthesized following the procedure illustrated in Example 51. Using N-(2-aminoethyl)-1,3-propanediamine (8.0 g, 8.6 mL, 68 mmol), 2-nitrobenzenesulfonyl chloride (53.0 g, 239 mmol), and $Et_3N$ (33 mL, 237 mmol) in $CH_2Cl_2$ (600 mL) afforded 43.5 g (95%) of the title compound as a pale green foam.

$R_f$ 0.33 (hexanes/EtOAc 2:8). $^1H$ NMR ($CD_3OD$) δ 1.86–1.92 (m, 2 H), 3.12–3.16 (m, 8 H), 5.61–5.75 (m, 2 H), 7.61–8.30 (m, 12 H). $^{13}$C NMR (CD$_3$OD) δ 28.7, 40.7, 42.2, 46.0, 47.8, 124.4, 124.8, 125.5, 131.0, 132.2, 133.0, 133.1, 133.8, 133.9, 134.2, 135.9, 148.1. HRMS (FAB) m/z 804.963 (M+Cs)$^+$ (C$_{23}$H$_{24}$N$_6$O$_{12}$S$_3$Cs requires 804.966).

EXAMPLE 53

2,6,11-(tris-o-nitrobenzenesulfonyl)-triazadodecane [2.6]-[4-(N4-t-Boc-piperazine-1-yl)]pyridinophane A mixture of 4-[N4'-(t-Boc)-piperazin-N1'-yl]-pyridine-2,6-dimethanolditosylate (6.0 g, 9.5 mmol), N1,N6,N10-tris(2-nitrobenzenesulfonyl)spermidine (7.3 g, 10 mmol) and Cs$_2$CO$_3$ (12.4 g, 38 mmol) in DMF (350 mL) was stirred at rt for 24 h. The solvent was removed in vacuo and the residue was diluted with CH$_2$Cl$_2$ and washed with H$_2$O. The layers were separated, and the aqueous phase was extracted with CH$_2$Cl$_2$. The combined organic phase was washed with brine, dried (Na$_2$SO$_4$), and concentrated in vacuo. The residue was purified by silica gel flash column chromatography using hexanes:EtOAc (6/4–1/9, v/v) to give 8.3 g (88%) of the title compound as a white foam.

R$_f$ 0.48 (EtOAc 100%). $^1$H NMR (CDCl$_3$) δ 1.25–1.39 (m, 4 H), 1.48 (s, 9 H), 1.78–1.82 (m, 2 H), 3.02–3.05 (m, 2 H), 3.08–3.11 (m, 2 H), 3.22–3.24 (m, 2 H), 3.26–3.39 (m, 8 H), 3.54–3.57 (m, 4 H), 4.34 (s, 2 H), 4.48 (s, 2 H), 6.81 (s, 2 H), 7.52–7.76 (m, 9 H), 7.83–7.85 (m, 1 H), 8.01–8.05 (m, 2 H). $^{13}$C NMR (CDCl$_3$) δ 10.9, 14.0, 23.0, 23.7, 24.5, 25.0, 28.4, 28.6, 29.0, 30.3, 38.7, 45.7, 46.7, 47.4, 48.6, 49.9, 54.4, 54.8, 68.1, 80.2, 107.3, 107.6, 124.1, 124.2, 128.8, 130.5, 130.7, 130.8, 131.6, 131.8, 132.9, 133.6, 148.2, 148.4, 154.6, 156.1, 156.4, 156.5, 167.8. HRMS (FAB) m/z 1120.165 (M+Cs)$^+$ (C$_{41}$H$_{49}$N$_9$O$_{14}$S$_3$Cs requires 1120.161).

EXAMPLE 54

2,5,9-(tris-o-nitrobenzenesulfonyl)-triazadecane [2.6]-[4-(N4-t-B6c-piperazine-1-yl)]pyridinophane The title compound was prepared following the procedure illustrated in Example 53 above. 4-[N4'-(t-Boc)-piperazin-N1'-yl]-pyridine-2,6-dimethanolditosylate (14.5 g, 23 mmol), N1,N3, N6-tris(2-nitrobenzenesulfonyl)-1,6-diamino-3-azahexane (16.9 g, 25 mmol) and Cs$_2$CO$_3$ (29.8 g, 92 mmol) in DMF (750 mL) afforded 16.3 g (72%) of the title compound as a white foam.

R$_f$ 0.35 (EtOAc 100%). $^1$H NMR (CDCl$_3$) δ 1.49 (s, 9 H), 1.99–2.01 (m, 2 H), 2.92–2.94 (m, 2 H), 3.21–3.23 (m, 2 H), 3.25–3.39 (m, 8 H), 3.52–3.59 (m, 6 H), 4.42–4.44 (m, 4 H), 6.85 (s, 1 H), 6.96 (s, 1 H), 7.59–7.77 (m, 9 H), 7.92–8.09 (m, 3 H). $^{13}$C NMR (CDCl$_3$) δ 27.5, 28.4, 45.7, 47.1, 47.5, 49.0, 55.9, 56.0, 80.3, 108.0, 108.4, 124.2, 124.3, 130.7, 131.1, 131.8, 131.9, 132.0, 132.1, 132.3, 133.6, 133.8, 148.0, 148.3, 154.5, 156.1, 156.6, 157.2. HRMS (FAB) m/z 1092.126 (M+H)$^+$ (C$_{39}$H$_{45}$N$_9$O$_{14}$S$_3$Cs requires 1092.130).

EXAMPLE 55

2,6,11-Triazadodecane[2.6]-[4-(N4-t-Boc-piperazine-1-yl)]-pyridinophane

Thiophenol (2.8 mL, 27 mmol) was added to a stirred mixture of 2,11-(bis-o-nitrobenzenesulfonyl)-6-(o-nitrobenzenesulfonyl)triazadodecane[2.6]-[4-(N4-t-Boc-piperazine-1-yl)]pyridinophane (7.4 g, 7.5 mmole) and anhydrous K$_2$CO$_3$ (10.4 g, 75 mmol, 10 equiv) in DMF (80 mL). The reaction mixture was stirred at rt for 4 h, and the solvent was removed under reduced pressure. The residue was diluted with CH$_2$Cl$_2$ and washed with H$_2$O. The layers were separated, and the aqueous phase was extracted with CH$_2$Cl$_2$ (3×). The combined organic phase was washed with brine, dried (Na$_2$SO$_4$), and concentrated in vacuo. The crude product was purified by silica gel flash column chromatography using MeOH (100%), and MeOH:NH$_4$OH (100:1–9/1, v/v) as the eluent to give 2.6 g (79%) of the title compound as a pale yellow foam.

R$_f$ 0.33 (MeOH/NH$_4$OH 4:1). $^1$H NMR (CDCl$_3$) δ 1.47 (s, 9 H), 1.57–1.68 (m, 6 H), 2.56–2.62 (m, 4 H), 2.71–2.79 (m, 4 H), 3.39–3.41 (m, 4 H), 3.54–3.59 (m, 4 H), 3.78 (s, 2 H), 3.81 (s, 2 H), 6.70 (s, 2 H). $^{13}$C NMR (CDCl$_3$) δ 27.59, 27.92, 28.05, 28.62, 46.88, 47.04, 54.58, 55.63, 81.57, 107.22, 107.44, 156.36, 157.67, 160.20, 160.33. HRMS (FAB) m/z 433.330 (M+H)$^+$ (C$_{23}$H$_{41}$N$_6$O$_2$ requires 433.329).

EXAMPLE 56

2,5,9-Triazadecane[2.6]-[4-(N4-t-Boc-piperazine-1-yl)]pyridinophane

The title compound was prepared following the procedures of Example 55 using 2,9-(bis-o-nitrobenzenesulfonyl)-5-(o-nitrobenzenesulfonyl)triazadecane[2.6]-[4-(N4-t-Boc-piperazine-1-yl)]pyridinophane. After work up and purification 4.65 g (65%) of the title compound was obtained as a pale yellow foam.

R$_f$ 0.10 (MeOH/NH$_4$OH 4:1). $^1$H NMR (CDCl$_3$) δ 1.47 (s, 9 H), 1.75–1.85 (m, 2 H), 2.78–2.86 (m, 2 H), 2.89–2.90 (m, 4 H), 3.19–3.24 (m, 2 H), 3.39–3.42 (m, 4 H), 3.52–3.53 (m, 4 H), 3.87–3.89 (m, 4 H), 6.65 (s, 1 H), 6.68 (s, 1 H). $^{13}$C NMR (CDCl$_3$) δ 26.78, 27.42, 28.62, 46.88, 47.39, 52.23, 53.55, 55.02, 81.60, 106.09, 106.79, 156.34, 157.78, 159.91, 164.41. HRMS (FAB) m/z 405.297 (M+H)$^+$ (C$_{21}$H$_{36}$N$_6$O$_2$H requires 405.297).

EXAMPLE 57

Synthesis of Libraries based on Scaffolds having Formula V, Libraries 69–78

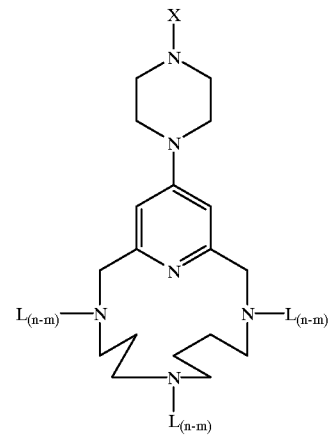

| Formula V | | | |
|---|---|---|---|
| Section | Library | X | L(n-m) |
| A | 80 | t-Boc | 18–21, 23–27 and 55 |
| B | 81 | H | 18–21, 23–27 and 55 |
| C | 82 | L$_{32}$ | 18–21, 23–27 and 55 |
| D | 83 | L$_{42}$ | 18–21, 23–27 and 55 |

43

-continued

Synthesis of Libraries based on Scaffolds having Formula V, Libraries 69–78

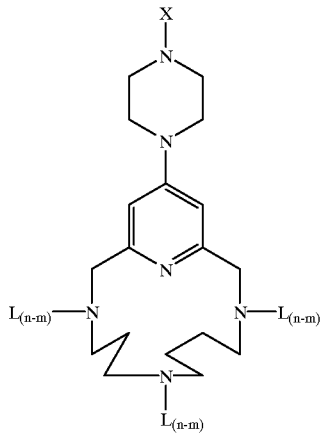

Formula V

| Section | Library | X | L(n-m) |
|---------|---------|---|--------|
| E | 84 | $L_{41}$ | 18–21, 23–27 and 55 |
| F | 85 | $L_{22}$ | 18–21, 23–27 and 55 |
| G | 86 | $L_{35}$ | 18–21, 23–27 and 55 |
| H | 87 | $L_{30}$ | 18–21, 23–27 and 55 |
| I | 88 | $L_{57}$ | 18–21, 23–27 and 55 |
| J | 89 | $L_{58}$ | 18–21, 23–27 and 55 |

A. Preparation of Library 80

A solution containing equimolar amounts of benzyl bromide (Br-$L_{18}$), α-bromo-m-xylene (Br-$L_{19}$), 3-fluorobenzyl bromide (Br-$L_{20}$, 3-cyanobenzyl bromide (Br-$L_{21}$), 3-chlorobenzyl bromide (Br-$L_{23}$), 3-nitrobenzyl bromide (Br-$L_{24}$), methyl 3-(bromomethyl)benzoate (Br-$L_{25}$), α'-bromo-α,α,α-trifluoro-m-xylene (Br-$L_{26}$), 3-bromobenzyl bromide (Br-$L_{27}$), and bromoacetonitrile ($L_{55}$) (total 11.1 mmol) in $CH_3CN$ (35 mL) was added to a stirred mixture of 2,6,11-triazadodecane[2.6]-[4-(N4-t-Boc-piperazine-1-yl)]pyridinophane (3.4 mmol) and $K_2CO_3$ (67.4 mmol) in $CH_3CN$ (20 mL). The resulting mixture was stirred at rt overnight. The solvent was evaporated and the residue was diluted with $CH_2Cl_2$ and washed with $H_2O$. The organic phase was separated and the aqueous phase was extracted with $CH_2Cl_2$. The combined organic phase was washed with brine, dried ($Na_2SO_4$) and concentrated. The residue was purified by silica gel flash column chromatography using hexanes:EtOAc (4/6–0/10, v/v), and EtOAc:MeOH (9/1, v/v) as eluents to afford 1.92 g (72%) of the title library.

$R_f$ 0.32–0.72 (MeOH:$NH_4OH$, 100/1).

B. Deprotection of Library 80, preparation of Library 81

Trifluoroacetic acid (TFA) (40 mL) was added to a stirred solution of Library 80 (1.9 g, 2.4 mmol) in $CH_2Cl_2$ (20 mL) at 0° C. The resulting reaction mixture was stirred at rt for 4 h. The solvent and excess TFA were evaporated, and the residue was diluted with $H_2O$ and extracted twice with $CH_2Cl_2$. The combined organic phase was washed with brine, dried ($Na_2SO_4$) and concentrated under reduced pressure. The residue was purified by silica gel flash column chromatography using EtOAc:MeOH (7/3–0/10, v/v) and MeOH:$NH_4OH$ (98/2, v/v) as the eluent to afford 1.08 g (66%) of the title library as a foam.

$R_f$ 0.11–0. 36 (MeOH:$NH_4OH$ 100/1).

C. General Procedure for Substitution at the X Position of Formula V, Preparation of Library 82

A mixture of Library 81 (0.15 mmol), anhydrous $K_2CO_3$ (2.70 mmol), and a selected activated letter (Br or Cl-$L_n$) (0.21 mmol) in $CH_3CN$ (5 mL) was stirred at rt overnight. The solvent was evaporated and the residue was diluted with $CH_2Cl_2$ and washed with $H_2O$. The layers were separated, and the aquous phase was extracted with $CH_2Cl_2$. The combined organic phase was washed with brine, dried ($Na_2SO_4$), and concentrated in vacuo. The residue was purified by preparative thin layer chromatography (PTLC) to give the respective library in an average of 53–91% yield.

Library 82 was prepared with this procedure from P-bromomethylbenzoic acid (Br-$L_{32}$). The Library was purified by PTLC (SiO$_2$, EtOAc/MeOH 2:4).

D. Preparation of Library 83

The title library was prepared following the procedures illustrated in Section C above using 3-nitro-4-bromomethylbenzoic acid (Br-$L_{42}$). The Library was purified by PTLC (SiO$_2$, MeOH/$NH_4OH$ 100:1).

E. Preparation of Library 84

The title library was prepared following the procedures illustrated in Section C above using 1,6-dichloro-4-bromomethylpyridine (Br-$L_{41}$). The Library was purified by PTLC (SiO$_2$, MeOH/$NH_4OH$ 100:1).

F. Preparation of Library 85

A solution of cinnamyl bromide (Br-$L_{22}$) (41 mg, 0.21 mmol) in THF (10 mL) was added to a stirred solution of Library 81 (148 mg, 0.21 mmol) and DIEA (44 μl, 0.25 mmol) in THF (10 mL) at 0° C. The reaction mixture was allowed to warm to rt and stirred for 4 h. The crude material was worked up as illustrated in Section C above. The material was purified by silica gel flash column chromatography using EtOAc:MeOH, (9/1, v/v) to give 58 mg (34%) of the title library.

$R_f$ 0.8–0.40 (EtOAc/MeOH 1:1).

G. Preparation of Library 86

The title library was prepared following the procedures illustrated in Section C above using t-butyl-α-bromoacetate (Br-$L_{35}$). The Library was purified by silica gel flash column chromatography using EtOAc.

H. Preparation of Library 87

The title library was prepared following the procedures illustrated for Section B above. Library 86 (0.14 g, 0.17 mmol) and TFA (4 mL) in $CH_2Cl_2$ (2 mL) were stirred at rt for 4 h. Purification by PTLC (SiO$_2$, MeOH 100%) gave 33 mg (25%) of the title library.

$R_f$ 0.12–0.34 (MeOH 100%).

I. Preparation of Library 88

A mixture of Library 81 (0.26 g, 0.38 mmol) and N,N'-Bis(t-Boc)-1H-pyrazol-1-carboxamidine ($L_{57}$) (0.22 g, 0.76 mmol) in DMF (3.8 mL) was heated at 60° C. for 24 h. The solvent was evaporated, and the residue was purified by silica gel flash column chromatography using EtOAc (100%) followed by EtOAc:MeOH (9/1–1/1, v/v) to give 0.12 g (35%) of the title library.

$R_f$ 0.23–0.48 (MeOH:NH$_4$OH 100/1).

J. Preparation of Library 89

TFA (8 mL) was added to a stirred solution of Library 88 (0.12 g, 0.13 mmol) in 2 mL of CH$_2$Cl$_2$ at 0° C. The reaction mixture was stirred at rt for 6 h and concentrated. The residue was treated with HCl/MeOH to yield 21 mg (23%) of the title library as the HCl salt.

EXAMPLE 58

Synthesis of Libraries based on Scaffolds having Formula VI, Libraries 90–95

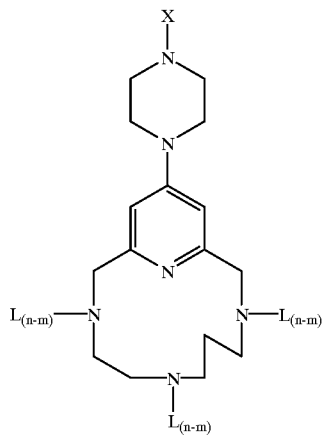

Formula VI

| Section | Library | X | L(n-m) |
|---------|---------|-----|--------|
| A | 90 | t-Boc | 1, 3, 16, 41, 42, 78 |
| B | 91 | t-Boc | 2, 7, 17, 41, 42, 78 |
| C | 92 | t-Boc | 28, 30, 32–34, 87 |
| D | 93 | t-Boc | 1, 2, 3, 7, 16, 17 |
| E | 94 | t-Boc | 5, 6, 9, 15, 37, 49 |
| F | 95 | t-Boc | 18, 25, 36, 38, 40, 78 |

A. General Procedure for Substitution at the X Position of Formula VI, Preparation of Library 90

The title library was prepared following the procedures of Example 57, Section A. To a mixture of 2,5,9-triazadecane [2.6]-[4-(N4-t-Boc-piperazine-1-yl)]pyridinophane (1.2 mmol) and K$_2$CO$_3$ (24 mmol) in CH$_3$CN (30 mL) was added 3-[N-(N,N-(bis-t-Boc)-guanidinyl]-benzylbromide (Br-L$_1$), N-bromoacetyl-N(N,N-bis-t-Boc-guanidinyl)piperazine (Br-L$_3$), 2-bromo-N'-[2'-(bis-N-t-Boc)ethylguanidino]-acetamide (Br-L$_{16}$), 3-nitro-4-bromomethylbenzoic acid (Br-L$_{42}$), 1,6-dichloro-4-bromomethylpyridine (Br-L$_{41}$) and benzoic anhydride (L$_{78}$) (3.60 mmol). The mixture was stirred at rt for 2 h and worked up as per Example 57, Section A. The crude product as purified by silica gel flash column chromatography using hexanes:EtOAc (2/8–0/10, v/v) as the eluent to give the title library as a foam.

B. Preparation of Library 91

Library 91 was prepared as illustrated in Section A above using 3-(N-Boc)-aminobenzylbromide (Br-L$_2$), benzoic anhydride (L$_{78}$), 1,6-dichloro-4-bromomethylpyridine (Br-L$_{41}$), 3-nitro-4-bromomethylbenzoic acid (Br-L$_{42}$), 2-bromo-N-[2'-(N'-t-Boc)ethylamino]-acetamide (Br-L$_{17}$) and N-Boc-N-bromoacetyl-piperazine (Br-L$_7$) as the active functionalities.

C. Preparation of Library 92

Library 91 was prepared as illustrated in Section A above using bromoacetic acid (Br-L$_{30}$), P-bromomethylbenzoic acid (Br-L$_{32}$), p-bromomethylphenylacetic acid (Br-L$_{33}$), p-cyano-benzylbromide (Br-L$_{34}$), α-bromoacetamide (Br-L$_{28}$) and 1,3-propane sultone (L$_{87}$) as the active functionalities.

D. Preparation of Library 93

Library 91 was prepared as illustrated in Section A above using 3-[N-(N,N-(bis-t-Boc)-guanidinyl]-benzylbromide (Br—), N-bromoacetyl-N(N,N-bis-t-Boc-guanidinyl) piperazine (Br-L$_3$), 1-Boc-2-chloromethylbenz-imidazole (Cl-L$_{15}$), 2-bromo-N-[2'-(N'-t-Boc)ethylamino]-acetamide (Br-L$_{17}$), N-Boc-N-bromoacetyl-piperazine (Br-L$_7$) and 3-(N-Boc)-aminobenzylbromide (Br-L$_2$) as the active functionalities.

E. Preparation of Library 94

Library 91 was prepared as illustrated in Section A above using 4-carboxymethyl benzylchloride (Cl-L$_{49}$), diethyl chloromethylphosphonate (Cl-L$_{37}$), 1-Boc-2-chloromethylbenzimidazole (Cl-L$_{15}$), N-Boc-N-(3-chloromethylbenzoyl)-piperazine (Cl-L$_9$), N-(4-chloromethylbenzoyl)-N(N,N-bis-t-Boc-guanidinyl) piperazine (Cl-L$_6$) and N-(3-chloromethylbenzoyl)-N(N,N-bis-t-Boc-guanidinyl)piperazine (Cl-L$_5$) as the active functionalities. The reaction mixture was heated to 68° C. and purification used hexanes:EtOAc (1/9, v/v) to give 950 mg of the title library as a foam.

F. Preparation of Library 95

Library 91 was prepared as illustrated in Section A. above using benzoic anhydride (L$_{78}$), Ethyl 6-chloro-5-cyano-2-trifluoromethyl-3-pyridinecarboxylate (Cl-L$_{40}$), methyl 2-chloro-4-trifluoromethyl-5-pyrimidine carboxylate (Cl-L$_{36}$), methyl α-bromoacetate (Br-L$_{38}$), methyl 3-(bromomethyl)benzoate (Br-L$_{25}$) and benzyl bromide (Br-L$_{18}$) as the active functionalities.

EXAMPLE 59

Deprotection and conversion of libraries 90–95 into HCl salts, preparation of Libraries 96–101

Following the procedures illustrated in Example 57, Section B libraries 90–95 are deblocked and further converted into their respective deprotected HCl salts having Formula VI.

| Library Init./final | X | L(n-m) |
|---------------------|---|--------|
| 90/96 | H | 29, 41, 42, 44, 45 and 46 |
| 91/97 | H | 28, 29, 41, 42, 48 and 86 |
| 92/98 | H | 28, 30, 32–34 and 87 |
| 93/99 | H | 44–49 |

-continued

| Library Init./final | X | L(n-m) |
|---|---|---|
| 94/100 | H | 33, 37, 50, 51, 52 and 54 |
| 95/101 | H | 18, 25, 29, 36, 38 and 40 |

EXAMPLE 60

General procedure for substitution at all positions of Formula VI

| Section | Library | X and L (n-m) |
|---|---|---|
| A | 102 | 1, 3, 16, 41, and 40 |
| B | 103 | 2, 7, 17, 36 and 26 |
| C | 104 | 4, 5, 6, 15 and 37 |
| D | 105 | 40, 41, 44, 45 and 46 |
| E | 106 | 26, 36, 47, 48 and 49 |
| F | 107 | 37, 45, 50, 52 and 54 |

A. Preparation of Library 102

The t-Boc group of 2,5,9-triazadecane[2.6]-[4-(N4-t-Boc-piperazine-1-yl)]pyridinophane was removed following the procedures illustrated in Example 57, Section B. TFA (15 mL) was added to a stirred solution of 2,5,9-triazadecane [2.6]-[4-(N4-t-Boc-piperazine-1-yl)]pyridinophane (2.0 g, 4.9 mmol) in $CH_2Cl_2$ (20 mL) at 0° C. The reaction mixture was stirred at rt for 4 h, and the solvent was removed under reduced pressure. The residue was purified by column chromatography using $MeOH:NH_4OH$ (100/0–7/3, v/v) to afford 1.4 g (96%) of the fully deprotected scaffold having Formula VI (each $L_{n-m}$=H and X=H) as a foam.

The fully deprotected scaffold was functionalized at all 4 positions simultaneously using 3-[N-(N,N-(bis-t-Boc)-guanidinyl]-benzylbromide (Br-$L_1$), N-bromoacetyl-N(N,N-bis-t-Boc-guanidinyl)piperazine (Br-$L_3$), 2-bromo-N'-[2'-(bis-N-t-Boc)ethylguanidino]-acetamide (Br-$L_{16}$), 1,6-dichloro-4-bromomethylpyridine (Br-$L_{41}$) and ethyl 6-chloro-5-cyano-2-trifluoromethyl-3-pyridinecarboxylate (Cl-$L_{40}$) as the reactive functionalities. Following the procedures illustrated in Examples 57 and 58 2,5,9-triazadecane [2.6]-[4-(piperazine-1-yl)]pyridinophane (1.3 mmol), reactive functionalities (5.2 mmol), and $K_2CO_3$ (26 mmol) in DMF (30 mL) was stirred at rt for 2 h. After the workup, the crude product was purified by silica gel flash column chromatography using EtOAc and EtOAc:MeOH (10:0–1:1, v/v) to give the title library. The yields for libraries 102–104 were on the average from about 59 to 73%. The libraries are isolated as foams.

B. Preparation of Library 103

The title library was prepared as per the procedures of Section A above using 3-(N-Boc)-aminobenzylbromide (Br-$L_2$), N-Boc-N-bromoacetyl-piperazine (Br-$L_7$), 2-bromo-N-[2'-(N'-t-Boc)ethylamino]-acetamide (Br-$L_{17}$), methyl 2-chloro-4-trifluoromethyl-5-pyrimidine carboxylate (Cl-$L_{36}$), α'-bromo-α,α,α-trifluoro-m-xylene (Br-$L_{26}$) as the reactive functionalities.

C. Preparation of Library 104

The title library was prepared as per the procedures of Section A above using N-(4-chloroacetyl)-N-[(N,N-bis-t-Boc)-guanidinyl]piperazine (Cl-$L_4$), N-(3-chloromethylbenzoyl)-N(N,N-bis-t-Boc-guanidinyl) piperazine (Cl-$L_5$), N-(4-chloromethylbenzoyl)-N(N,N-bis-t-Boc-guanidinyl)piperazine (Cl-$L_6$), 1-Boc-2-chloromethylbenzimidazole (Cl-$L_{15}$) and diethyl chloromethylphosphonate (Cl-$L_{37}$) as the reactive functionalities.

D. Preparation of Library 105

Library 102 was deblocked following the procedure of Example 57, Section B, to give the title library.

E. Preparation of Library 106

Library 103 was deblocked following the procedure of Example 57, Section B, to give the title library.

F. Preparation of Library 107

Library 104 was deblocked following the procedure of Example 57, Section B, to give the title library.

EXAMPLE 61

General procedure for preparation of libraries having Formula VII, preparation of Libraries 108, 109 and 110

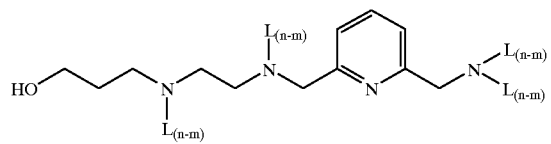

Formula VII

| Section | Ln-m |
|---|---|
| A | 1, 7, 11, 35, 36 and 87 |
| B | 2, 3, 17, 40, 43 and 79 |
| C | 5, 10, 15, 90, 37 and 86 |

A. Preparation of Library 108

A solution containing six reactive functionalities selected from bromide and chloride substituted compounds (0.68 mmol each, in a total of 4.08 mmol, 4.08 equiv, 1.02 equiv per reactive site) in anhydrous acetonitrile (30 mL) was added to a stirred mixture of 2-aminomethylene-6-{[N1-(methyl-1-yl)-N2-1-propanol-3-yl]-1,2-diaminoethane}pyridine (prepared as per the procedures illustrated in the PCT of ISIS-2274, international patent application PCT/US97/13530 filed Aug. 1, 1997, the contents of which are incorporated herein by reference. (238 mg, 1.0 mmol) and anhydrous potassium carbonate (3.0 g) in DMF (4 mL) and acetonitrile (10 mL). The resulting reaction mixture was stirred at room temperature for 2 h (at 50–60° C./8 h for Library 110), and aminomethylated polystyrene resin (0.5 g, 0.49 mmol) was added. After stirring for 1 h, the solvent was evaporated, and the residue was dissolved in a mixture of chloroform-water. The organic phase was separated, and the aqueous phase was extracted with chloroform. The combined organic phase was washed with brine, dried ($Na_2SO_4$), and concentrated. The residue was passed through a short silica gel column using hexanes:EtOAc (½, v/v), EtOAc and then MeOH as eluents. The library thus obtained, after evaporation of the solvent, was dissolved in chloroform (8 mL) and treated with TFA (12 mL) at room temperature for 3 h. The reaction mixture was concentrated and the residue was dissolved in HCl(g) saturated methanol. The solution was concentrated under vacuum to give 87 to 92% of the respective library as the hydrochloride salt as a pale yellow oil.

Library 108 was prepared using 3-[N-(N,N-(bis-t-Boc)-guanidinyll-benzylbromide (Br-$L_1$), N-Boc-N-bromoacetyl-piperazine (Br-$L_7$), 2-Bromomethyl Pyridine-6-methanol (Br-$L_{11}$), t-butyl-α-bromoacetate (Br-$L_{35}$), methyl 2-chloro-4-trifluoromethyl-5-pyrimidine carboxylate (Cl-$L_{36}$) and 1,3-propane sultone ($L_{87}$) as the reactive functionalities.

B. Preparation of Library 109

Library 109 was prepared using was prepared using 3-(N-Boc)-aminobenzylbromide (Br-$L_2$), N-bromoacetyl-N (N,N-bis-t-Boc-guanidinyl)piperazine (Br-$L_3$), 2-bromo-N-[2'-(N'-t-Boc)ethylamino]-acetamide (Br-$L_{17}$), ethyl 6-chloro-5-cyano-2-trifluoromethyl-3-pyridinecarboxylate (Cl-$L_{40}$), 4-bromomethyl-3-nitrobenzoic acid (Br-$L_3$) and 4-trifluoromethylbenzylbromide (Br-$L_{79}$) as the reactive functionalities.

C. Preparation of Library 110

Library 110 was prepared using N-(3-chloromethylbenzoyl)-N(N,N-bis-t-Boc-guanidinyl) piperazine (Cl-$L_5$), N'-(t-Boc)-N"-(α-chloro)acetyl ethylenediamine (Cl-$L_{10}$), 1-Boc-2-chloromethylbenzimidazole (Cl-$L_{15}$), diethyl chloromethylphosphonate (Cl-$L_{37}$), 2-chloropyrimidine (Cl-$L_{86}$) and 3-chloromethyl-1,2,3-oxadiazole (Cl-$Br_{90}$) as the reactive functionalities.

Library 108 was assayed as illustrated in the procedures to determine the minimum inhibitory concentration. The activity in the *S. pyogenes* procedure was 42 μM (94% inhibition).

The activity of Library 109 in the *S. pyogenes* procedure was 42 μM (95% inhibition). The activity in the *E. coli* procedure was 20 μM (86% inhibition). The activity in the Tat/tar assay was 100 μM (138% inhibition).

EXAMPLE 62

Preparation of libraries 111, 112 and 113 having Formula VII, deblocking of libraries 108–110

Libraries 111–113 were treated as per the procedures illustrated in Example 59, to remove all t-Boc blocking groups attached to the letter.

EXAMPLE 63

2-[(N-o-nitrosulfonyl-N-acetamide)-aminomethyl]-6-{[N1-methyl-N1-o-nitrosulfonyl)-N2-(Boc)-N2-1-propanol]-1,2-diaminoethane}pyridine A mixture of triprotected 2-[(N-o-nitrosulfonyl)-aminomethyl]-6-{[N1-methyl-N1-o-nitrosulfonyl)-N2-(Boc)1-propanol]-1,2-diaminoethane}pyridine (1.06 g, 1.5 mmol), bromoacetamide (227 mg, 1.65 mmol, 1.1 equiv), and potassium carbonate (1.5 g) in 20 mL of acetonitrile was stirred at room temperature overnight. The solvent was evaporated and the residue was dissolved in water-chloroform. The layers were separated, and the aqueous phase was extracted with chloroform. The combined organic phase was washed with brine, dried ($Na_2SO_4$) and concentrated. The residue was purified by flash chromatography on a silica gel column. Elution with 100% EtOAc and then 3:1 EtOAc—MeOH gave 0.93 g (81%) of the title compound as a white foam.

Silica gel TLC $R_f$ 0.51 (10:1 EtOAc—MeOH). $^1$H NMR (CDCl$_3$) δ 1.38 (s, 9H), 1.48–1.72 (m, 2H), 3.08–3.27 (m, 4H), 3.40–3.62 (m, 4H), 4.14 (s, 2H), 4.56 (s, 2H), 4.61 (s, 2H), 7.10 –7.30 (m, 3H), 7.58–7.78 (m, 6H), 7.90–8.06 (m, 2H). HRMS (FAB) m/z 898.117 (M+Cs)$^+$ ($C_{31}H_{39}N_7S_2O_{12}Cs$ requires 898.115).

EXAMPLE 64

2-(N-acetamide-aminomethyl)-6-{[N1-methyl)-N2-(Boc)-N2-1-propanol]-1,2-diaminoethane}pyridine A mixture of compound 2-[(N-o-nitrosulfonyl-N-acetamide)-aminomethyl]-6-{[N1-methyl-N1-o-nitrosulfonyl)-N2-(Boc)-N2-1-propanol]-1,2-diaminoethane}pyridine (0.90 g, 1.17 mmol), potassium carbonate (1.5 g) and thiophenol (290 μL, 311 mg, 2.82 mmol) in 30 mL of DMF was stirred at room temperature overnight. The solvent was evaporated, and the residue was dissolved in water-chloroform. The layers were separated, and the aqueous phase was extracted with chloroform. The combined organic phase was washed with brine, dried ($Na_2SO_4$), and concentrated. The residue was purified by flash chromatography on a silica gel column. Elution with 100% EtOAc, 100:1 and then 20:1 MeOH-30% $NH_4OH$ gave 123 mg (27%) of the title compound as a pale yellow oil.

Silica gel TLC $R_f$ 0.4 9 (100:1 MeOH-30% $NH_4OH$). $^1$H NMR (CDCl$_3$) δ 1.38 (s, 9H), 1.56–1.75 (m, 2H), 2.72–2.88 (m, 2H), 3.20–3.60 (m, 8H), 3.84 (s, 2H), 3.87 (s, 2H), 6.45 (br, 2H), 7.02 –7.20 (m, 2H), 7.55 (t, 1H, J=7.7 Hz). MS (FAB) m/z 396 (M+H )$^+$. HRMS (FAB) m/z 418.244 (M+Na)$^+$ ($C_{19}H_{33}N_5O_3Na$ requires 418.243).

EXAMPLE 65

2-[(N-m-trifluoromethylbenzyl-N-acetamide)-aminomethyl]-6-{[N1-methyl]-N1-m-trifluoromethylbenzyl)-N2-(Boc)-N2-1-propanol]-1,2-diaminoethane}pyridine The title compound was prepared as described above for 2-[(N-o-nitrosulfonyl-N-acetamide)-aminomethyl]-6-{[N1-methyl-N1-o-nitrosulfonyl)-N2-(Boc)-N2-1-propanol]-1,2-diaminoethane}pyridine from 2-(N-acetamide-aminomethyl)-6-{[N1-methyl)-N2-(Boc)-N2-1-propanol]-1,2-diaminoethane}pyridine (120 mg, 0.303 mmol), potassium carbonate (1.0 g) and α,α,α,-trifluoro-α'-bromo-m-xylene (112 μL, 173 mg, 0.72 mmol, 2.39 equiv) in 5 mL of acetonitrile. Flash chromatographic purification using 1:1 hexanes-EtOAc and then 5:1 EtOAc—MeOH as eluents afforded 199 mg (92%) of the title compound as a pale yellow oil.

Silica gel TLC $R_f$ 0.53 (5:1 EtOAc—MeOH). $^1$H NMR (CDCl$_3$) δ 1.25 (s, 9H), 1.40–1.70 (m, 2H), 2.56–2.72 (m, 2H), 3.10–3.35 (m, 6H), 3.40–3.55 (m, 2H), 3.69 (s, 4H), 3.75 (s, 2H), 3.78 (s, 2H), 6.48 (br, 1H), 6.99–7.10 (m, 1H), 7.30–7.68 (m, 9H), 8.20–8.45 (m, 1H). MS (FAB) m/z 712 (M+H )$^+$. HRMS (FAB) m/z 844.228 (M+Cs)$^+$ ($C_{35}H_{43}N_5O_4F_6Cs$ requires 844.227).

EXAMPLE 66

2-[(N-m-trifluoromethylbenzyl-N-acetamide)-aminomethyl]-6-{[N1-methyl]-N1-m-trifluoromethylbenzyl)-N2-1-propanol]-1,2-diaminoethane}pyridine TFA (5 mL) was added to a solution of compound 2-[(N-m-trifluoromethylbenzyl-N-acetamide)- aminomethyl]-6-{[N1-methyl-N1-m-trifluoromethylbenzyl)-N2-(Boc)-N2-1-propanol]-1,2-diaminoethane}pyridine (190 mg, 0.267 mmol) in 1 mL of chloroform at 0° C. The mixture was stirred at room temperature for 4 h, concentrated, and dissolved in aqueous potassium carbonate solution-chloroform. The layers were separated, and the aqueous phase was extracted with chloroform. The combined organic phase was washed with brine, dried ($Na_2SO_4$), and concentrated. Preparative thin layer chromatographic purification using 150:1 MeOH-30% $NH_4OH$ as developing agent gave 80 mg (53%) of the title compound as a pale yellow oil.

Silica gel TLC $R_f$ 0.56 (50:1 MeOH-30% $NH_4OH$). $^1H$ NMR ($CDCl_3$) δ 1.50–1.75 (m, 2H), 2.60–2.85 (m, 6H), 3.23 (s, 2H), 3.55–3.82 (m, 8H), 3.95–4.20 (m, 2H), 6.38 (br, 2H), 6.99–7.65 (m, 11H), 8.25 (br, 1H). $^{13}C$ NMR ($CDCl_3$) δ 30.4, 46.8, 48.9, 53.2, 57.6, 58.6, 58.8, 60.3, 60.4, 62.9, 121.7, 122.0, 124.0, 124.2, 125.4, 128.2, 128.9, 130.4, 131.0, 132.1, 137.2, 139.2, 140.2, 157.4, 159.2, 174.4. MS (FAB) m/z 744 (M+Cs)$^+$. HRMS (FAB) m/z 612.274 (M+H)$^+$ ($C_{30}H_{36}N_5O_2F_6$ requires 612.277).

The title compound was assayed in the *S. pyogenes* procedure and the activity was: 100 μM, 95% inhibition. The activity found in the *E. coli* procedure was: 100 μM, 87% inhibition.

EXAMPLE 67

2-(N,N-bis-t-Boc-guanidinyl)methyl-6-{[N1-methyl-N1-o-nitrosulfonyl-N2-Boc-N2-1-propanol]-1,2-diaminoethane}-pyridine A solution of 2-aminomethyl-6-{[N1-methyl-N1-o-nitrosulfonyl-N2-Boc-N2-1-propanol]-1,2-diaminoethane}-pyridine (1.35 g, 2.57 mmol) and 1,3-bis(t-Boc)-2-methyl-2-thiopseudourea (1.53 g, 5.26 mmol, 2.0 equiv) in 20 mL of DMF was stirred at 50–60° C. for 3 h, and room temperature overnight. The solvent was evaporated, and the residue was dissolved in water-chloroform. The layers were separated, and the aqueous phase was extracted with chloroform. The combined organic phase was washed with brine, dried ($Na_2SO_4$), and concentrated. The residue was purified by flash chromatography on a silica gel column. Elution with 10:1, 1:1 and then 0:1 hexanes-EtOAc afforded 0.98 g (50%) of the title compound as a white foam.

Silica gel TLC $R_f$ 0.51 (1:4 hexanes-EtOAc). $^1H$ NMR ($CDCl_3$) δ 1.30–1.75 (m, 29H), 3.20–3.70 (m, 8H), 4.60, 4.62 (s, 2H), 4.69 (s, 2H), 7.10–7.30 (m, 3H), 7.47–7.70 (m, 3H), 7.90 (d, 1H, J=7.2 Hz), 9.20 (br, 1H), 11.52 (br, 1H). $^{13}C$ NMR ($CDCl_3$) δ 28.1, 28.3, 30.4, 42.9, 45.4, 45.7, 46.9, 53.1, 58.2, 79.5, 80.7, 83.1, 120.8, 121.4, 124.0, 125.3, 128.2, 129.0, 130.7, 131.5, 133.5, 137.7, 148.0, 153.0, 155.4, 155.6, 156.0, 156.6, 163.5. HRMS (FAB) m/z 898.243 (M+Cs)$^+$ ($C_{34}H_{51}N_7O_{11}SCs$ requires 898.242). Anal. Calcd. for $C_{34}H_{51}N_7O_{11}S$: C, 53.32; H, 6.70; N, 12.80. Found: C, 53.42; H, 6.66; N, 12.57.

EXAMPLE 68

2-(N,N-bis-t-Boc-guanidinyl)methyl-6-{[N1-methyl-N2-Boc-N2-1-propanol]-1,2-diaminoethane}pyridine The title compound was prepared as described above for 2-(N-acetamide-aminomethyl)-6-{[N1-methyl)-N2-(Boc)-N2-1-propanol]-1,2-diaminoethane}pyridine from 2-aminomethyl-6-{[N1-methyl-N1-o-nitrosulfonyl-N2-Boc-N2-1-propanol]-1,2-diaminoethane}pyridine (0.87 g, 1.13 mmol), potassium carbonate (1.5 g), and thiophenol (200 μL, 215 mg, 1.9 mmol, 1.7 equiv) in 20 mL of DMF. Flash chromatographic purification using 100% EtOAc, 10:1 and then 5:1 EtOAc—MeOH as eluents afforded 655 mg (99%) of product 12 as a light yellow oil.

Silica gel TLC $R_f$ 0.50 (2:1 EtOAc—MeOH. $^1H$ NMR ($CDCl_3$) δ 1.37 (s, 9H), 1.48 (s, 18H), 1.55–1.70 (m, 2H), 2.70–2.88 (m, 2H), 3.15–3.60 (m, 6H), 3.89 (s, 2H), 4.68 (s, 1H), 4.70 (s, 1H), 7.07 (t, 2H, J=7.8 Hz), 7.57 (m, 1H, J=7.8 Hz), 9.70 (br, 1H), 11.49 (br, 1H). $^{13}C$ NMR ($CDCl_3$) δ 28.1, 28.3, 30.7, 43.6, 45.6, 47.6, 47.9, 54.1, 58.3, 79.3, 79.9, 82.9, 119.8, 120.7, 137.2, 153.1, 154.6, 155.7, 158.4, 163.5. MS (FAB) m/z 581 (M+H)$^+$. HRMS (FAB) m/z 713.262 (M+Cs)$^+$ ($C_{28}H_{48}N_6O_7Cs$ requires 713.263). Anal. Calcd. for $C_{28}H_{48}N_6O_7$: C, 57.91; H, 8.32; N, 14.47. Found: C, 57.67; H, 7.99; N, 14.61.

EXAMPLE 69

2-(N,N-bis-t-Boc-guanidinyl)methyl-6-{[N1-methyl-N2-Boc-N2-1-propanol]-1,2-diaminoethane}pyridine The title compound was prepared as described above for 2-[(N-m-trifluoromethylbenzyl-N-acetamide)-aminomethyl]-6-{[N1-methyl-N1-m-trifluoromethylbenzyl)-N2-1-propanol]-1,2-diaminoethane}pyridine from 2-(N,N-bis-t-Boc-guanidinyl)methyl-6-{[N1-methyl-N2-Boc-N2-1-propanol]-1,2-diaminoethane}pyridine (110 mg, 0.189 mmol) and 5 mL of TFA. The solvent was evaporated under reduced pressure, and the residue was dissolved in HCl (g) saturated methanol. The solution was concentrated under vacuum to afford 85 mg (97%) hydrochloride salt of the title compound as a white solid.

$^1H$ NMR ($D_2O$) δ 1.90–2.10 (m, 2H), 3.20–3.37 (m, 4H), 3.65 (s, 1H), 3.60–3.78 (m, 4H), 4.58 (s, 2H), 4.66 (s, 2H), 7.50 (t, 2H, J=7.8 Hz), 7.96 (t, 1H, J=7.8 Hz). MS (FAB) m/z 303 (M+Na)$^+$. HRMS (FAB) m/z 281.209 (M+H)$^+$ ($C_{13}H_{25}N_6O$ requires 281.209).

EXAMPLE 70

2-(N,N-bis-t-Boc-guanidinyl)methyl-6-{[N1-methyl-N1-m-trifluoromethylbenzyl-N2-Boc-N2-1-propanol]-1,2-diaminoethane}pyridine The title compound was prepared as described above for 2-[(N-m-trifluoromethylbenzyl-N-acetamide)-minomethyl]-6-{[N1-methyl-N1-m-trifluoromethylbenzyl)-N2-Boc)-N2-1-propanol]-1,2-diaminoethane}pyridine from 2-(N,N-bis-t-Boc-guanidinyl)methyl-6-{[N1-methyl-N2-Boc-N2-1-propanol]-1,2-diaminoethane}pyridine (0.53 g, 0.91 mmol), potassium carbonate (1.5 g), and α,α,α,-trifluoro-α'-bromo-m-xylene (155 μL, 240 mg, 1.0 mmol, 1.1 equiv) in 10 mL of acetonitrile. Flash chromatographic purification using 5:1 and then 1:2 hexanes-EtOAc as eluents afforded 580 mg (86%) of the title compound as a colorless oil.

Silica gel TLC $R_f$ 0.30 (1:1 hexanes-EtOAc). $^1H$ NMR ($CDCl_3$) δ 1.19 (s, 9H), 1.37 (s, 9H), 1.40 (s, 9H), 1.40–1.60 (m, 2H), 2.50–2.65 (m, 2H), 3.00–3.48 (m, 6H), 3.69 (s, 2H), 3.75 (s, 2H), 4.62 (s, 1H), 4.64 (s, 1H), 6.98–7.02 (m, 1H), 7.20–7.60 (m, 6H), 9.38 (br, 1H), 11.46 (br, 1H). $^{13}C$ NMR ($CDCl_3$) δ 27.9, 28.2, 30.5, 43.2, 45.0, 45.8, 51.9, 58.2, 58.7, 60.0, 79.1, 79.8, 82.7, 119.9, 121.5, 123.8, 125.2, 126.9, 128.7, 130.2, 130.8, 131.9, 137.1, 140.6, 152.8, 154.8, 155.9, 156.6, 158.6, 163.5. MS (FAB) m/z 739

(M+H)⁺. HRMS (FAB) m/z 871.296 (M+Cs)⁺ ($C_{36}H_{53}N_6O_7F_3Cs$ requires 871.298). Anal. Calcd. for $C_{36}H_{53}N_6O_7F_3$: C, 58.52; H, 7.22; N, 11.37. Found: C, 58.52; H, 6.93; N, 11.15.

EXAMPLE 71

2-(N,N-bis-t-Boc-guanidinyl)methyl-6-{[N1-methyl-N1-m-trifluoromethylbenzyl-N2-1-propanol]-1,2-diaminoethane}-pyridine The title compound was prepared as described above for compound 2-[(N-m-trifluoromethylbenzyl-N-acetamide)-aminomethyl]-6-{[N1-methyl-N1-m-trifluoromethylbenzyl)-N2-1-propanol]-1,2-diaminoethane}pyridine from 2-(N,N-bis-t-Boc-guanidinyl)methyl-6-{[N1-methyl-N1-m-trifluoromethylbenzyl-N2-Boc-N2-1-propanol]-1,2-diaminoethane}pyridine (540 mg, 0.73 mmol) and 8 mL of TFA. Flash chromatographic purification using 50:1 MeOH-30% $NH_4OH$ as eluent afforded 150 mg (47%) of the title compound as a pale yellow oil.

Silica gel TLC $R_f$ 0.49 (50:1 MeOH-30% $NH_4OH$). $^1H$ NMR (CDCl₃) δ 1.45–1.70 (m, 2H), 2.54–2.78 (m, 6H), 3.58–3.82 (m, 6H), 4.25–4.70 (m, 2H), 7.00–7.70 (m, 7H). HRMS (FAB) m/z 439.244 (M+H)⁺ ($C_{21}H_{30}N_6OF_6$ requires 439.243).

The title compound was assayed in the below procedure for S. pyogenes and was found to have activity at 100 μM (95% inhibition).

EXAMPLE 72

3,10-Bis(2-nitrobenzenesulfonyl)-3,6,10,16-tetraazabicyclo[10.3.1]hexadeca-1(16),12,14-triene A solution of compound 2,9-diaza-6-(t-Boc)azadecane [2.6]pyridinophane (from Example 22, 1.41 g, 2.04 mmol), 10 mL of trifluroacetic acid (TFA) and 10 mL of $CH_2Cl_2$ was stirred at rt overnight. The solvent and excess TFA were evaporated and the residue was dissolved in $H_2O$. The solution was adjusted to a pH of 10 and extracted with $CHCl_3$. The combined organic phase was washed with 5% $NaHCO_3$ solution and then brine, dried ($Na_2SO_4$) and concentrated. The residue was purified by flash chromatography on a silica gel column using 100:1 MeOH—$NH_4OH$ as an eluent to give 0.88 g (73%) of the title compound as a white foam.

$^1H$ NMR (CDCl₃) δ 1.49–1.68 (m, 2H), 1.95–2.25 (br, 1H, ex $D_2O$), 2.22 (t, 2H, J=4.8 Hz), 2.34 (t, 2H, J=5.4 Hz), 3.32–3.43 (m, 4H), 4.49 (s, 2H), 4.54 (s, 2H), 7.31 (d, 1H, J=7.3 Hz), 7.44(d, 1H, J=8 Hz), 7.60–7.74(m, 7H), 7.92–8.05 (m, 2H). $^{13}C$ NMR (CDCl₃) δ 27.5, 44.8, 46.2, 47.2, 50.4, 55.2, 55.5, 122.7, 123.8, 124.3, 130.4, 131.2, 131.9, 132.4, 142.6, 133.8, 138.2, 148.3, 148.5, 156.0, 156.2. HRMS (FAB) m/z 591.1342 (M+1)⁺ ($C_{26}H_{27}N_6O_8S_2$ requires 591.1332). Anal. Calcd for $C_{26}H_{26}N_6O_8S_2 \cdot H_2O$: C, 47.36; H, 4.64; N, 13.82. Found: C, 47.04; H, 4.50; N, 13.51.

EXAMPLE 73

6-(1-Anthraquinonemethyl)-3,10-bis(2-nitrobenzenesulfonyl)-3,6,10,16-tetraazabicyclo [10.3.1]hexadeca-1(16),12,14-triene A mixture of 3,10-bis(2-nitrobenzenesulfonyl)-3,6,10,16-tetraazabicyclo[10.3.1]hexadeca-1(16),12,14-triene (0.65 g, 1.1 mmol), 1-(bromomethyl) anthroquinone (0.35 g, 1.16 mmol) and $K_2CO_3$ (0.6 g, 4.4 mmol) in 15 mL of anhydrous DMF was stirred at rt overnight. The solvent was evaporated and the residue was dissolved in $CHCl_3$—$H_2O$. The organic phase was separated, and the aqueous phase was extracted with $CHCl_3$. The combined organic phase was washed with brine, dried ($Na_2SO_4$) and concentrated. The residue was purified by flash chromatography on a silica gel column using $CH_2Cl_2$ as an eluent to give 0.68 g (76%) of the title compound as a pale yellow foam.

$^1H$ NMR (CDCl₃) δ 1.20–1.45 (m, 2H), 2.01–2.25 (m, 4H), 3.10–3.42 (m, 4H), 3.45 (s, 2H), 4.51 (s, 4H), 7.40–8.10 (m, 18H). $^{13}C$ NMR (CDCl₃) δ 25.9, 46.8, 47.4, 50.2, 50.8, 54.8, 59.6, 124.1, 124.3, 125.3, 126.8, 127.0, 127.4, 128.2, 129.0, 130.3, 130.5, 131.9, 132.5, 133.5, 133.8, 134.2, 138.7, 146.7, 148.3, 155.2, 155.8, 182.7, 183.0. HRMS (FAB) m/z (M+1)⁺ 811.1851 ($C_{39}H_{35}N_6O_{10}S_2$ requires 811.1856). Anal. Calcd for $C_{39}H_{34}N_6O_{10}S_2$: C, 57.75; H, 4.23; N, 10.37. Found: C, 58.00; H, 4.45; N, 10.13.

EXAMPLE 74

6-(1-Anthraquinonemethyl)-3,6,10,16-tetraazabicyclo-[10.3.1]hexadeca-1(16),12,14-triene A mixture of compound 6-(1-anthraquinonemethyl)-3,10-bis(2-nitrobenzenesulfonyl)-3,6,10,16-tetraazabicyclo-[10.3.1]hexadeca-1(16),12,14-triene (0.62 g, 0.76 mmol), thiophenol (0.25 g, 2.3 mmol) and $K_2CO_3$ (0.95 g, 6.9 mmol) was stirred at rt overnight. The solvent was evaporated and the residue was dissolved in $CHCl_3$—$H_2O$. The organic phase was separated and the aqueous phase was extracted with $CHCl_3$. The combined organic phase was dried ($Na_2SO_4$), concentrated and the residue was purified by flash chromatography on a silica gel column using $CH_2Cl_2$ and then 1:1 $CH_2Cl_2$—MeOH as eluents to give 0.24 g (73%) of the title compound as a white foam.

$^1H$ NMR (CDCl₃) δ 1.75–1.90 (m, 2H), 2.32–2.53 (m, 6H), 2.74 (t, 2H, J=5.3 Hz), 3.70 (s, 2H), 3.73 (s, 2H), 3.91 (s, 2H), 3.90–4.20 (br, 2H, ex $D_2O$), 6.92 (d, 1H, J=7.8 Hz), 6.99 (d, 1H, J=7.3 Hz), 7.50 (t, 1H, J=7.5 Hz), 7.68–7.73 (m, 2H), 7.85–7.89 (m, 1H), 8.18–8.25 (m, 4H). $^{13}C$ NMR (CDCl₃) δ 26.7, 46.9, 49.3, 52.4, 53.5, 55.4, 55.8, 58.9, 120.4, 127.1, 127.7, 132.6, 133.6, 133.9, 134.8, 136.6, 146.5, 158.7, 159.0, 182.9, 183.1. HRMS (FAB) m/z 441.2309 (M+1)⁺ ($C_{27}H_{29}N_4O_2$ requires 441.2291). Anal. Calcd for $C_{27}H_{28}N_4O_2 \cdot 1.5 H_2O$: C, 69.68; H, 6.67; N, 12.04. Found: C, 69.26; H, 6.80; N, 11.76.

EXAMPLE 75

6-(1-Pyrenebutyryl)-3,10-bis(2-nitrobenzenesulfonyl)-3,6,10,16-tetraazabicyclo [10.3.1]hexadeca-1(16),12,14-triene A mixture of 1-pyrenebutyric acid (0.87 g, 3.0 mmol) and 4-methylmorpholine (0.59 g, 5.9 mmol) in 20 mL of anhydrous $CH_2Cl_2$ was stirred at rt for 30 min. After addition of 1,3-dicyclohexylcarbodiimide (DCC) (0.62 g, 3.0 mmol) and 1-hydroxybenzotriazole (HOBT) (0.41 g, 3.0 mmol), the resulting solution was stirred at rt for another 30 min. A solution of 3,10-bis(2-nitrobenzenesulfonyl)-3,6,10,16-tetraazabicyclo[10.3.1]hexadeca-1(16), 12,14-triene (from Example 72, 1.77 g, 3.0 mmol) was added to the above solution and the resulting solution was stirred at rt for 40 h. The solution was filtered and the filtrate was washed with brine, dried ($Na_2SO_4$) and concentrated. The residue was purified by flash chromatography on a silica gel column using 100:1 $CH_2Cl_2$—MeOH as an eluent to give 2.36 g (92%) of the title compound as a pale yellow foam.

¹H NMR (CDCl$_3$) δ 1.58 (m, 2H), 2.10–2.22 (m, 2H), 2.27–2.43 (m, 2H), 2.67–2.75 (m, 1H), 2.94 (m, 1H), 3.08–3.25 (m, 2H), 3.34–3.38 (m, 6H), 4.43–4.60 (m, 4H), 7.32–8.39 (m, 20H). HRMS (FAB) m/z 861.2351 (M+1)$^+$ (C$_{44}$H$_{41}$N$_6$O$_9$S$_2$ requires 861.2376). Anal. Calcd for C$_{44}$H$_{40}$N$_6$O$_9$S$_2$: C, 61.38; H, 4.69; N, 9.77. Found: C, 61.11; H, 4.80; N, 9.81.

EXAMPLE 76

6-(1-Anthraquinonecarbonyl)-3,10-bis (2-nitrobenzenesulfonyl)-3,6,10,16-tetraazabicylo [10.3.1]hexadeca-1(16),12,14-triene The title compound was prepared following the procedures illustrated above in Example 75 using 3,10-bis (2-nitrobenzenesulfonyl)-3,6,10,16-tetraazabicyclo-[10.3.1] hexadeca-1(16),12,14-triene (1.0 g, 1.7 mmol), anthraquinone-2-carboxylic acid (0.43 g, 1.7 mmol), DCC (0.35 g, 1.7 mmol), HOBT (0.23 g, 1.7 mmol) and 4-methylmorpholine (0.25 g, 2.5 mmol) in 10 mL of anhydrous THF and 20 mL of anhydrous DMF in 56 h. The compound was purified by flash chromatography on a silica gel column using 200:1 CH$_2$Cl$_2$—MeOH as an eluent to give 1.06 g (76%) of the title compound as a pale yellow foam.

¹H NMR (CDCl$_3$) δ 1.50–1.63 (m, 2H), 3.19–3.32 (m, 3H), 3.40–3.55 (m, 3H), 3.50–3.68 (m, 2H), 4.53–4.67 (m, 4H), 7.44–8.37 (m, 18H). HRMS (FAB) m/z 825.1666 (M+1)$^+$ (C$_{39}$H$_{33}$N$_6$O$_{11}$S$_2$ requires 825.1641). A satisfactory elemental analysis result was obtained for 6-(1-anthraquinonecarbonyl)- 3,6,10,16-tetraazabicyclo[10.3.1] hexadeca-1(16),12,14-triene, a derivative of the title compound which was prepared as illustrated in Example 79 below.

EXAMPLE 77

6-(1-Pyrenecarbonyl)-3,10-bis(2-nitrobenzenesulfonyl)-3,6,10,16-tetraazabicyclo [10.3.1]hexadeca-1(16),12,14-triene The title compound was prepared following the procedures illustrated above in Example 75 using 3,10-bis(2-nitrobenzenesulfonyl)-3,6,10,16-tetraazabicyclo-[10.3.1] hexadeca-1(16),12,14-triene (0.59 g, 1.0 mmol), 1-pyrenecarboxylic acid (0.25 g, 1.0 mmol), DCC (0.21 g, 1.0 mmol), HOBT (0.14 g, 1.0 mmol) and 4-methylmorpholine (0.15 g, 1.5 mmol) in 20 mL of CH$_2$Cl$_2$ and 10 mL of DMF. The compound was purified by flash chromatography on a silica gel column using 200:1 CH$_2$Cl$_2$—MeOH as an eluent to give 0.7 g (86%) of the title compound as a pale yellow foam.

¹H NMR (CDCl$_3$) δ 1.75–1.95 (m, 1H), 2.30–2.55 (m, 1H), 2.85–3.35 (m, 4H), 3.40–3.95 (m, 4H), 4.30–4.80 (m, 4H), 5.91 (t, 0.5 H, J=6.3 Hz), 6.18 (d, 0.5H, J=9.5 Hz), 6.99 (t, 0.5H, J=7.6 Hz), 7.13–8.40 (m, 18.5H). HRMS (FAB) m/z 819.1933 (M+1)$^+$ (C$_{41}$H$_{35}$N$_6$O$_9$S$_2$ requires 819.1899). Anal. Calcd for C$_{41}$H$_{34}$N$_6$O$_9$S$_2$: C, 60.13; H, 4.19; N, 10.27. Found: C, 60.30; H, 4.16; N, 10.35.

EXAMPLE 78

6-(1-Pyrenebutyryl)-3,6,10,16-tetraazabicyclo [10.3.1]-hexadeca-1(16),12,14-triene A mixture of 6-(1-Pyrenebutyryl)-3,10-bis(2-nitrobenzenesulfonyl)-3,6,10,16-tetraazabicyclo[10.3.1]-hexadeca-1(16),12,14-triene (2.26 g, 2.6 mmol), thiphenol (0.87 g, 7.8 mmol) and K$_2$CO$_3$ (3.22 g, 23.4 mmol) in 20 mL of DMF was stirred at rt overnight. The solvent was evaporated and the residue was dissolved in CHCl$_3$—H$_2$O. The organic phase was separated and the aqueous phase was extracted with CHCl$_3$. The combined organic phase was dried (Na$_2$SO$_4$) and concentrated. The residue was purified by flash chromatography on a silica gel column using CH$_2$Cl$_2$ and then 3:1 CH$_2$Cl$_2$—MeOH as eluents to give 1.12 g (65%) of the title compound as a white foam.

¹H NMR (CDCl$_3$) δ 1.10–1.35 (m, 1H), 1.45–1.65 (m, 1H), 2.00–2.95 (m, 12H, 2H ex D$_2$O), 3.10–3.38 (m, 4H), 3.65 (s, 1H), 3.68 (s, 1H), 3.79 (s, 1H), 3.82 (s, 1H). ¹³C NMR (CDCl$_3$) δ 27.0, 29.1, 32.2, 32.4, 32.7, 44.3, 46.0, 46.2, 46.5, 46.9, 48.1, 48.9, 54.1, 55.0, 55.3, 120.7, 120.9, 121.3, 123.6, 124.8, 125.0, 125.8, 126.6, 127.3, 127.5, 128.8, 129.8, 131.4, 136.3, 137.1, 159.7, 160.2, 172.7. HRMS (FAB) m/z 491.2830 (M+1)$^+$ (C$_{32}$H$_{35}$N$_4$O requires 491.2811). Anal. Calcd for C$_{32}$H$_{34}$N$_4$O.1.5H$_2$O: C, 74.27; H, 7.16; N, 10.83. Found: C, 74.68; H, 7.13; N, 10.62.

EXAMPLE 79

6-(1-Anthraquinonecarbonyl)-3,6,10,16-tetraazabicyclo-[10.3.1]hexadeca-1(16),12,14-triene The title compound was prepared following the procedures illustrated above in Example 78 using 6-(1-anthraquinonecarbonyl)-3,10-bis(2-nitrobenzenesulfonyl)-3,6,10,16-tetraazabicyclo[10.3.1]hexadeca-1(16),12,14-triene (1.02 g, 1.24 mmol), thiophenol (0.41 g, 3.72 mmol) and K$_2$CO$_3$ (1.7 g, 12.5 mmol). The crude material was purified by flash chromatography on a silica gel column using CH$_2$Cl$_2$ and then MeOH, 15:1 MeOH—NH$_4$OH (30%) as eluents to give 0.45 g (80%) of the title compound as a pale yellow foam.

¹H NMR (CDCl$_3$) δ, 1.30–1.52 (m, 1H), 1.55–1.82 (m, 1H), 2.27 (s, 2H ex D$_2$O), 2.55–3.02 (m, 4H), 3.07 (s, 2H), 3.45 (m, 1H), 3.64 (m, 1H), 3.94 (m, 4H), 7.08–7.12 (d, 2H, J=7.7 Hz), 7.52–7.89 (m, 4H), 8.17 (s, 4H), 8.26–8.31(m, 3H). ¹³H NMR (CDCl$_3$) δ 28.1, 28.4, 28.6, 29.0, 43.4, 43.6, 45.6, 47.3, 47.8, 48.1, 49.6, 54.7, 55.8, 121.1, 121.8, 125.0, 127.4, 127.5, 132.0, 133.4, 134.3, 137.5, 142.6, 160.3, 169.9, 182.5. HRMS (FAB) m/z 455.2070 (M+1)$^+$ (C$_{27}$H$_{27}$N$_4$O$_3$ requires 455.2077). Anal. Calcd for C$_{27}$H$_{26}$N$_4$O$_3$.2H$_2$O: C, 66.09; H, 6.11; N, 11.42. Found: C, 66.73; H, 5.70; N, 11.28.

EXAMPLE 80

6-(1-Pyrenecarbonyl)-3,6,10,16-tetraazabicyclo [10.3.1]-hexadeca-1(16),12,14-triene The title compound was prepared following the procedures illustrated above in Example 78 using 6-(1-pyrenecarbonyl)-3,10-bis(2-nitrobenzenesulfonyl)-3,6,10, 16-tetraazabicyclo[10.3.1]hexadeca-1(16),12,14-triene (0.64 g, 0.78 mmol), thiophenol (0.26 g, 2.34 mmol) and K$_2$CO$_3$ (1.0 g, 7.4 mmol) in 20 mL of DMF. The product was purified by flash chromatography on a silica gel column using 10:1 CH$_2$Cl$_2$—MeOH and then 10:1 MeOH—NH$_4$OH (30%) to give 0.27 g (77%) of the title compound as a pale yellow foam.

¹H NMR (CDCl$_3$) δ 1.18–1.40 (m, 1H), 1.72–1.95 (m, 1H), 2.36–2.43 (m, 1H), 2.63 (br, 4H, 2H ex D$_2$O), 2.85–3.06 (m, 1H), 3.03–3.35 (m, 2H), 3.32–3.56 (m, 1H), 3.72–4.12 (m, 5H). ¹³C NMR (CDCl$_3$) δ 28.3, 28.7, 43.2, 45.5, 46.7, 47.8, 48.4, 48.6, 49.4, 54.3, 54.6, 55.5, 55.9, 120.8, 121.1, 121.8, 123.5, 123.9, 124.0, 124.6, 125.5, 126.3, 127.2, 127.7, 128.0, 128.6, 130.8, 131.2, 131.4, 131.8, 137.4, 159.9, 160.3, 171.4, 171.6. HRMS (FAB) m/z 449.2318 (M+1)$^+$ (C$_{29}$H$_{29}$N$_4$O requires 449.2335 ). Anal. Calcd for C$_{29}$H$_{28}$N$_4$O.2H$_2$O: C, 71.87; H, 6.60; N, 11.57. Found: C, 71.30; H, 6.05; N, 11.26.

EXAMPLE 81

5-(t-Boc)amino-1-pentanyl tosylate

A solution of tosyl chloride (28.6 g, 0.15 mol) in 200 mL of THF was added dropwise into a mixture of NaOH (24.0 g, 0.6 mol) and 5-(t-Boc)amino-1-pentanol (prepared by treating 5-amino-1-pentanol with Di-t-butyldicarbonate as per the procedure of Example 22(b)) (20.3 g, 0.1 mol) in 200 mL of H$_2$O and 300 mL of THF at 0° C. The resulting solution was stirred at rt overnight. The reaction solution was poured onto 100 g of ice and 80 mL of HCl (37%) and extracted with CHCl$_3$. The combined organic phase was washed with 5% NaHCO$_3$ solution and brine, dried (Na$_2$SO$_4$) and concentrated. The residue was purified by flash chromatography on a silica gel column using CH$_2$Cl$_2$ as an eluent to give 15.6 g (46%) of the title compound as an pale yellow oil.

$^1$H NMR (CDCl$_3$) δ 1.21–1.45 (m, 4H), 1.42 (s, 9H), 1.57–1.70 (m, 2H), 2.44 (s, 3H), 3.00–3.10 (q, 2H, J=6.3 Hz), 4.00 (t, 2H, J=6.4 Hz), 4.50 (m, 1H), 7.33 (d, 2H, J=8.2 Hz), 7.77 (d, 2H, J=8.2 Hz). $^{13}$C NMR (CDCl$_3$) δ 21.5, 22.6, 28.4, 29.3, 40.1, 70.4, 78.8, 127.8, 129.8, 133.1, 144.7, 156.0. HRMS (FAB) m/z 358.1688 (M+1)$^+$ (C$_{17}$H$_{28}$NO$_4$S requires 358.1688). Anal. Calcd for C$_{17}$H$_{27}$NO$_4$S: C, 57.11; H, 7.62; N, 3.92. Found: C, 56.98; H, 7.59; N, 4.08.

EXAMPLE 82

6-[5-(t-Boc)amino-1-pentanyl]-3,10-bis(2-nitrobenzenesulfonyl)-3,6,10,16-tetraazabicyclo[10.3.1]-hexadeca-1(16),12,14-triene A mixture of compound 3,10-bis(2-nitrobenzenesulfonyl)-3,6,10,16-tetraazabicyclo[10.3.1]hexadeca-1(16),12,14-triene (2.0 g, 3.4 mmol), K$_2$CO$_3$ (1.0 g, 7.2 mmol) and 5-(t-Boc)amino- 1-pentanyl tosylate (Example 81, 1.39 g, 4.1 mmol) in 50 mL of anhydrous CH$_3$CN. The resulting mixture was refluxed for two days. The solvent was evaporated and the residue was dissolved in CHCl$_3$—H$_2$O. The organic phase was separated and the aqueous phase was extracted with CHCl$_3$. The combined organic phase was washed with brine, dried (Na$_2$SO$_4$) and concentrated. The residue was purified by flash chromatography on a silica gel column using 200:1 and then 100:1 CH$_2$Cl$_2$—MeOH as eluents to give 1.37 g (57%) of the title compound as a pale yellow foam.

$^1$H NMR (CDCl$_3$) δ 1.11–1.51 (m, 15 H), 1.95–2.10 (m, 2H), 2.06–2.25 (m, 4H), 2.90–3.09 (m, 4H), 3.10–3.30 (m, 4H), 4.55–4.65 (br, 1H), 4.91–5.00 (s, 4H), 7.35–7.47 (m, 2H), 7.55–7.76 (m, 7H), 7.89–8.02 (m, 2H). $^{13}$C NMR (CDCl$_3$) δ 23.0, 24.4, 25.6, 26.8, 28.4, 29.9, 32.3, 40.5, 46.7, 47.5, 49.8, 50.3, 54.7, 55.3, 62.3, 78.8, 124.0, 124.3, 130.3, 132.1, 132.5, 134.0, 138.7, 148.2, 155.1, 155.7, 156.1. HRMS (FAB) m/z 776.2761 (M+1)$^+$ (C$_{34}$H$_{46}$N$_7$O$_{10}$S$_2$ requires 776.2748). Anal. Calcd for C$_{34}$H$_{45}$N$_7$O$_{10}$S$_2$: C, 52.63; H, 5.85; N, 12.64. Found: C, 52.68; H, 6.00; N, 12.47.

EXAMPLE 83

6-(5-Amino-1-pentanyl)-3,10-bis(2-nitrobenzenesulfonyl)-3,6,10,16-tetraazabicyclo[10.3.1]hexadeca-1(16),12,14-triene A solution of compound 6-[5-(t-Boc)amino-1-pentanyl]-3,10-bis(2-nitrobenzenesulfonyl)-3,6,10,16-tetraazabicyclo[10.3.1]hexadeca-1(16),12,14-triene (1.28 g, 1.65 mmol) in 8 mL of TFA and 8 mL of CH$_2$Cl$_2$ was stirred at rt overnight. The solvent was evaporated and the residue was dissolved in H$_2$O. The solution was adjusted to a pH of about 10 with NaOH and extracted with CHCl$_3$. The combined organic phase was dried (Na$_2$SO$_4$) and concentrated. The residue was purified by flash chromatography on a silica gel column using 2:1 CH$_2$Cl$_2$—MeOH and then 10:1 MeOH—NH$_4$OH (30%) as eluents to give 0.97 g (87%) of the title compound as a yellow foam.

$^1$H NMR (CDCl$_3$) δ 1.18–1.55 (m, 10H, 2H ex D$_2$O), 2.05–2.14 (m, 2H), 2.26 (t, 4H, J=6.8 Hz), 2.65 (t, 2H, J=6.8 Hz), 3.22–3.34 (m, 4H), 4.54 (s, 2H), 4.55 (s, 2H); 7.46–7.60 (m, 2H), 7.62–7.80 (m, 7H), 8.00–8.12 (m, 2H). $^{13}$C NMR (CDCl$_3$) δ 24.5, 25.6, 27.0, 33.4, 42.0, 46.8, 47.4, 49.8, 50.4, 54.7, 55.4, 124.1, 124.3, 130.3, 132.0, 132.6, 133.9, 138.6, 148.2, 155.0, 155.7. HRMS (FAB) m/z 676.2241 (M+1)$^+$ (C$_{29}$H$_{38}$N$_7$O$_8$S$_2$ requires 676.2223). Anal. Calcd for C$_{29}$H$_{37}$N$_7$O$_8$S$_2$: C, 51.53; H, 5.52; N, 14.52. Found: C, 51.35; H, 5.70; N, 14.36.

EXAMPLE 84

6-[5-(1-Anthraquinonecarbonyl)amino-1-pentanyl]-3,10-bis(2-nitrobenzenesulfonyl)-3,6,10,16-tetraazabicyclo[10.3.1]-hexadeca-1(16),12,14-triene A solution of anthraquinone-2-carboxylic acid (151 mg, 0.6 mmol) and 4-methylmorpholine (91 mg, 0.9 mmol) in 10 mL of CH$_2$Cl$_2$ was stirred at rt for 30 min. After addition of DCC (124 mg, 0.6 mmol), HOBT (81 mg, 0.6 mmol), the solution was stirred another 30-min. A solution of 3,10-bis(2-nitrobenzenesulfonyl)-3,6,10,16-tetraazabicyclo-[10.3.1]hexadeca-1(16),12,14-triene (405 mg, 0.6 mmol) in 5 mL of CH$_2$Cl$_2$ was added to the above solution and the resulting solution was stirred for 30 h. The reaction solution was filtered and the filtrate was washed with brine, dried (Na$_2$SO$_4$) and concentrated. The residue was purified by flash chromatography on a silica gel column using EtOAc as eluent to give 0.41 g (76%) of the title compound as a yellow foam. $^1$H NMR (CDCl$_3$) δ 1.40–1.75 (m, 4H), 1.91–2.11 (m, 2H), 2.12–2.32 (m, 4H), 3.14–3.30 (m, 4H), 3.30–3.51 (m, 4H), 4.20–4.35 (m, 2H), 6.96–7.10 (br, 1H), 7.31–8.49 (m, 18H). HRMS (FAB) m/z 910.2506 (M+1)$^+$ (C$_{44}$H$_{44}$N$_7$O$_{11}$S$_2$ requires 910.2540). A satisfactory elemental analysis result was obtained for compound 6-[5-(1-Anthraquinonecarbonyl) amino-1-pentanyl]-3,6,10,16-tetraazabicyclo[10.3.1]hexadeca-1(16),12,14-triene (5) 5, a derivative of the title compound.

EXAMPLE 85

6-[5-(1-Pyrenecarbonylamino)-1-pentanyl]-3,10-bis(2-nitrobenzenesulfonyl)-3,6,10,16-tetraazabicyclo[10.3.1]-hexadeca-1(16),12,14-triene A solution of 1-pyrenecarboxylic acid (0.22 g, 0.89 mmol) and 4-methymoroholine (0.12 g, 1.14 mmol) in 5 mL of anhydrous THF was stirred for 30 min. After addition of DCC (0.16 g, 0.76 mmol) and HOBT (0.11 g, 0.76 mmol), the solution was stirred another 30 min. A solution of 6-(5-amino-1-pentanyl)-3,10-bis(2-nitrobenzenesulfonyl)-3,6,10,16-tetraazabicyclo[10.3.1]hexadeca-1(16),12,14-triene (0.51 g, 0.76 mmol) was added into the above solution and stirred at rt overnight. The solvent was evaporated and the residue was dissolved in CH$_2$Cl$_2$. The resulting solution was washed with 5% NaHCO$_3$ solution and brine, dried and concentrated. The residue was purified by flash chromatography on a silica gel column using 100:1 $CH_2Cl_2$—MeOH as an eluent to give 0.45 g (65%) of the title compound as a yellow foam.

$^1$H NMR (CDCl$_3$) δ 1.30–1.50 (m, 6H), 1.67 (s, 2H), 2.00–2.15 (m, 2H), 2.20–2.38 (m, 4H), 3.19–3.38 (m, 4H), 3.54–3.64 (q, 2H, J=6.0 Hz), 4.46 (s, 2H), 4.48 (s, 2H), 6.35 (br, 1H), 7.38–7.74 (m, 9H), 7.89–8.23 (m, 11H), 8.50–8.55 (d, 1H, J=9.0 Hz). $^{13}$C NMR (CDCl$_3$) δ 24.7, 25.7, 26.7, 29.4, 40.2, 46.8, 47.5, 49.8,.50.4, 54.6, 55.2, 123.9, 124.2, 124.4, 125.6, 126.3, 127.1, 128.3, 130.2, 130.5, 131.0, 131.5, 131.9, 132.0, 132.4, 1432.5, 133.7, 138.5, 148.1, 154.9, 155.6, 170.0. HRMS (FAB) m/z 904.2816 (M+1)$^+$ ($C_{46}H_{46}N_7O_9S_2$ requires 904.2798). Anal. Calcd for $C_{46}H_{45}N_7O_9S_2.2H_2O$: C, 58.76; H, 5.22; N, 10.85. Found: C, 59.06; H, 5.38; N, 10.42.

EXAMPLE 86

6-[5-(1-Anthraquinonecarbonyl)amino-1-pentanyl]-3,6,10,16-tetraazabicyclo[10.3.1]hexadeca-1(16),12,14-triene A mixture of compound 6-(5-amino-1-pentanyl)-3,10-bis(2-nitrobenzenesulfonyl)-3,6,10,16-tetraazabicyclo-[10.3.1]hexadeca-1(16),12,14-triene (0.4 g, 0.44 mmol), PhSH (0.15 g, 1.32 mmol) and K$_2$CO$_3$ (0.55 g, 3.96 mmol) was stirred at rt overnight. The solvent was evaporated and the residue was dissolved in CHCl$_3$—H$_2$O. The organic phase was separated and the aqueous phase was extracted with CHCl$_3$. The combined organic phase was dried (Na$_2$SO$_4$) and concentrated. The residue was purified by flash chromatography on a silica gel column using 1:1 CH$_2$Cl$_2$—MeOH as an eluent to give 80 mg (34%) of the title compound as a yellow foam.

$^1$H NMR (CDCl$_3$) δ 1.30–1.80 (m, 1OH, 2H ex D$_2$O), 2.15–2.25 (m, 2H), 2.25–2.49 (m, 6H), 3.32–3.60 (m, 4H), 3.74 (s, 2H), 3.80 (s, 2H), 6.87 (d, 2H, J=7.6 Hz), 7.39 (t, 1H, J=7.4 Hz), 7.75–7.80 (m, 2H), 8.05–8.38 (m, 5H), 8.60 (s, 1H). $^{13}$C NMR (CDCl$_3$) δ 24.9, 26.3, 27.2, 28.9, 40.2, 47.0, 49.8, 52.0, 53.3, 53.6, 56.0, 57.5, 120.4, 120.5, 125.4, 127.3, 127.6, 133.3, 133.4, 134.3, 136.5, 158.4, 158.7, 182.5, 182.6. HRMS (FAB) m/z 540.2953 (M+1)$^+$ ($C_{32}H_{38}N_5O_3$ requires 540.2966). Anal. Calcd for $C_{32}H_{37}N_3O_3.2H_2O$: C, 66.74; H, 7.13; N, 12.17. Found: C, 67.00; H, 6.77; N, 11.41.

EXAMPLE 87

6-[(5-(1-Pyrenecarbonyl)amino-1-pentanyl]-3,6,10,16-tetraazabicyclo[10.3.1]hexadeca-1(16),12,14-triene A mixture of compound 6-[5-(1-anthraquinonecarbonyl)amino-1-pentanyl]-3,10-bis(2-nitrobenzenesulfonyl)-3,6,10,16-tetraazabicyclo[10.3.1]hexadeca-1(16),12,14-triene (0.31 g, 0.34 mmol), PhSH (0.11 g, 1.02 mmol), and K$_2$CO$_3$ (0.42 g, 3.00 mmol.) in 10 mL of anhydrous DMF was stirred at rt overnight. The solvent was evaporated and the residue was dissolved in H$_2$O and extracted with CHCl$_3$. The combined organic solution was dried (Na$_2$SO$_4$), and concentrated. The residue was purified by flash chromatography on a silica gel column using CH$_2$Cl$_2$, 4:1 CH$_2$C$_2$—MeOH and then 5:1 MeOH—NH$_4$H (30%) as eluents to give 0.16 g (89%) of the title compound as a yellow foam.

$^1$H NMR (CDC$_3$) δ 1.42–1.65 (m, 6H), 1.65–1.82 (m, 2H), 2.01–2.14 (m, 2H), 2.15–2.48 (m, 8H),3.30 (s, 2H), 3.53 (s, 2H), 3.56–3.65 (m, 2H), 3.50–3.95 (br, 2H, ex D$_2$O). $^{13}$C NMR (CDCl$_3$) δ 24.9, 26.4, 27.2, 29.3, 40.3, 47.1, 49.7, 52.1, 53.2, 53.6, 56.1, 57.0, 120.0, 124.1, 124.7, 125.5, 126.1, 127.1, 128.2, 130.7, 131.1, 132.0, 136.0, 158.3, 158.5, 170.2. HRMS (FAB) m/z 534.3224 (M+1)$^+$ ($C_{34}H_{40}N_5O$ requires 534.3224). Anal. Calcd for $C_{34}H_{39}N_5O.2H_2O$: C, 71.70; H, 7.55; N, 12.30. Found: C, 71.61; H, 7.30; N, 12.15.

EXAMPLE 88

6-(5-t-Boc-amino-3-aza-2-carboxylpentanyl)-3,10-Bis(2-nitrobenzenesulfonyl)-3,6,10,16-tetraazabicyclo-[10.3.1]hexadeca-1(16),12,14-triene A mixture of 3,10-bis(2-nitrobenzenesulfonyl)-3,6,10,16-tetraazabicyclo[10.3.1]hexadeca-1(16),12,14-triene (2.0 g, 3.4 mmol), 2-bromo-N-[2'-(N'-t-Boc)ethylamino]-acetamide (L$_{17}$) (1.0 g, 3.57 mmol) and K$_2$CO$_3$ (2 g, 14. 1 mmol) in 20 mL of anhydrous CH$_3$CN was stirred at rt overnight. The solvent was evaporated and the residue was dissolved CHCl$_3$—H$_2$O. The organic phase was separated and the aqueous phase was extracted with CHCl$_3$. The combined organic phase was washed with brine, dried (Na$_2$SO$_4$) and concentrated. The residue was purified by flash chromatography on a silica gel column using 200:1 and 100:1 CH$_2$Cl$_2$—MeOH as eluents to give 2.17 g (81%) of the title compound as a yellow foam.

$^1$H NMR (CDCl$_3$) δ 1.38 (s, 9H), 1.35–1.50 (m, 2H), 2.22–2.45 (m, 4H), 2.95 (s, 2H), 3.13–3.42 (m, 8H), 4.54 (s, 2H), 4.56 (s, 2H), 5.03 (br, 1H), 7.10 (br, 1H), 7.48 (d, 2H, J=7.8 Hz), 7.61–7.80 (m, 7H), 8.01–8.08 (m, 2H). $^{13}$C NMR (CDCl$_3$) δ 25.0, 28.4, 39.7, 40.6, 46.8, 47.4, 50.5, 51.6, 54.5, 55.2, 59.4, 79.2, 123.8, 124.3, 130.6, 132.1, 132.6, 133.8, 134.1, 138.7, 148.2, 155.4, 155.9, 156.4, 171.3. HRMS (FAB) m/z 791.2489 (M+1)$^+$ ($C_{33}H_{43}N_8O_{11}S_2$ requires 791.2483). Anal. Calcd for $C_{33}H_{42}N_8O_{11}S_2.2H_2O$: C, 47.92; H, 5.57; N, 13.55. Found: C, 47.86; H, 5.71; N, 13.29.

EXAMPLE 89

6-(5-Amino-3-aza-2-carbonylpentanyl)-3,10-bis(2-nitrobenzenesulfonyl)-3,6,10,16-tetraazabicyclo [10.3.1]hexadeca-1(16),12,14-triene A solution of 6-(5-t-Boc-amino-3-aza-2-carboxylpentanyl)-3,10-Bis(2-nitrobenzenesulfonyl)-3,6,10,16-tetraazabicyclo[10.3.1]hexadeca-1(16),12,14-triene (2.0 g, 2.53 mmol) in 10 mL of TFA and 5 mL of CH$_2$Cl$_2$ was stirred at rt overnight. The solvent was evaporated and the residue was dissolved in H$_2$O. After adjusting the pH to about 10, the solution was extracted with CHCl$_3$. The combined organic phase was dried (Na$_2$SO$_4$) and concentrated. The residue was purified by flash chromatography on a silica gel column using 10:1 CH$_2$Cl$_2$—MeOH and then 20:1 MeOH—NH$_4$OH (30%) as eluents to give 1.42 g (82%) of the title compound as a yellow foam.

$^1$H NMR (CDCl$_3$) δ 1.42–1.58 (m, 2H), 1.70 (s, 2H, ex D$_2$O), 2.29–2.44 (m, 4H), 2.77 (t, 2H, J=5.8 Hz), 2.95 (s, 2H), 3.21–3.37 (m, 6H), 4.54 (s, 4H), 7.22 (br, 1H), 7.46 (d, 1H, J=7.2 Hz) , 7.62–7.81 (m, 7H), 8.00–8.05 (m, 2H). $^{13}$C NMR (CDCl$_3$) δ 24.6, 41.2, 46.8, 47.0, 50.0, 51.8, 54.0, 54.9, 59.4, 123.9, 124.3, 124.4, 130.5, 132.0, 132.1, 132.6, 133.9, 134.1, 138.7, 148.2, 155.3, 155.6, 170.9. HRMS (FAB) m/z 691.1981 (M+1)$^+$ ($C_{28}H_{35}N_8O_9S_2$ requires 691.1961 ). Anal. Calcd for $C_{28}H_{34}N_8O_9S_2.2H_2O$: C, 47.44; H, 5.08; N, 15.81. Found: C, 47.44; H, 5.19; N, 15.86.

EXAMPLE 90

6-[5-(1-Anthraquinonecarbonyl)amino-3-aza-2-carboxyl-pentanyl]-3,10-bis(2-nitrobenzenesulfonyl)-3,6,10,16-tetraazabicyclo [10.3.1]hexadeca-1(16),12,14-triene A solution of anthraquinone-2-carboxylic acid (0.18 g, 0.7 mmol) and 4-methylmorpholine in 10 mL of anhydrous DMF was stirred at rt for 30 minutes. After addition of DCC (0.14 g, 0.7 mmol) and HOBT (0.1 g, 0.7 mmol), the solution was stirred for another 30 minutes. A solution of 6-(5-amino-3-aza-2-carbonylpentanyl)-3,10-bis(2-nitrobenzenesulfonyl)-3,6,10,16-tetraazabicyclo-[10.3.1] hexadeca-1(16),12,14-triene (0.46 g, 0.67 mmol) in 10 mL of anhydrous DMF was added and the resulting solution was stirred at rt for 24 h. The solvent was evaporated and the residue was dissolved in $CHCl_3$—$H_2O$. The organic phase was separated and the aqueous phase was extracted with $CHCl_3$. The combined organic phase was dried ($Na_2SO_4$) and concentrated. The residue was purified by flash chromatography on a silica gel column using 100:1 $CH_2Cl_2$—MeOH as an eluent to give 0.45 g (73%) of the title compound as a yellow foam.

$^1$H NMR (CDCl$_3$) δ 1.34–1.58 (m, 2H), 2.32–2.43 (m, 4H), 3.01 (s, 2H), 3.33–3.42 (m, 4H), 3.59 (s, 4H), 4.49 (s, 2H), 4.52 (s, 2H), 7.27–7.44 (m, 3H), 7.59–7.88 (m, 10H), 7.95–8.05 (m, 2H), 8.18–8.32 (m, 4H), 8.65 (d, 1H, J=1.8 Hz). $^{13}$C NMR (CDCl$_3$) δ 25.0, 39.1, 41.2, 47.3, 50.9, 51.9, 54.2, 55.4, 59.2, 123.6, 123.9, 124.3, 126.0, 127.3, 127.6, 130.6, 131.8, 132.0, 132.6, 133.3, 134.1, 134.4, 134.8, 138.6, 139.4, 148.2, 155.4, 155.9, 166.0, 172.4, 182.2, 182.4. HRMS (FAB) m/z 925.2259 (M+1)$^+$ ($C_{43}H_{41}N_8O_{12}S_2$ requires 925.2245). Anal Calcd for $C_{43}H_{40}N_8O_{12}S_2 \cdot H_2O$: C, 53.75; H, 4.58; N, 11.66. Found: C, 53.96; H, 4.76; , N, 11.64.

EXAMPLE 91

6-[5-(1-Pyrenecarbonyl)amino-3-aza-2-carboxylpentanyl]-3,10-bis(2-nitrobenzenesulfonyl)-3,6,10,16-tetraazabicyclo[10.3.1]hexadeca-1(16),12,14-triene A solution of 1-pyrenecarboxylic acid (0.16 g, 0.65 mmol) and 4-methylmorpholine (84 mg, 0.83 mmol) in 5 mL of anhydrous THF was stirred at rt for 30 min. After addition of DCC (0.11 g, 0.56 mmol) and HOBT (75 mg, 0.56 mmol), the solution was stirred for another 30 min. A solution of 6-(5-amino-3-aza-2-carbonylpentanyl)-3,10-bis(2-nitrobenzenesulfonyl)-3,6,10,16-tetraazabicyclo-[10.3.1] hexadeca-1(16),12,14-triene (0.39 g, 0.56 mmol) in 5 mL of anhydrous THF was added and the resulting solution was stirred at rt for two days. The solvent was evaporated and the residue was dissolved in $CHCl_3$—$H_2O$. The organic phase was separated and the aqueous phase was extracted with $CHCl_3$. The combined organic phase was washed with brine, dried ($Na_2SO_4$) and concentrated. The residue was purified by flash chromatography on a silica gel column using 100:1 $CH_2Cl_2$—MeOH as an eluent to give 0.44 g (81%) of the title compound as a yellow foam.

$^1$H NMR (CDCl$_3$) δ 1.45–1.50 (m, 2H), 2.22–2.43 (m, 4H), 2.96 (s, 2H), 3.23–3.42 (m, 4H), 3.56–3.80 (m, 4H), 4.35 (s, 2H), 4.49 (s, 2H), 7.05–7.45 (m, 6H), 7.50–7.65 (m, 5H), 7.90–8.22 (m, 10H), 8.55 (d, 1H, J=9.2 Hz). $^{13}$C NMR (CDCl$_3$) δ 24.7, 24.9, 33.8, 39.4, 40.5, 47.2, 50.7, 51.8, 54.0, 55.2, 59.2, 123.3, 123.6, 123.9, 124.1, 124.3, 124.6, 124.8, 125.6, 126.3, 127.1, 128.3, 130.0, 130.3, 130.5, 130.8, 130.9, 131.5, 131.9, 132.1, 132.5, 133.5, 133.7, 138.3, 147.7, 148.1, 155.3, 155.6, 170.4, 171.7. HRMS (FAB) m/z 919.2536 (M+1)$^+$ ($C_{45}H_{43}N_8O_{10}S_2$ requires 919.2534). Anal Calcd for $C_{45}H_{42}N_8O_{10}S_2$: C, 58.81; H, 4.61; N, 12.20. Found: 58.88; H, 4.92; N, 11.82.

EXAMPLE 92

6-(1-Anthraquinonecarboxyl)amino-3-aza-2-carbonylpentanyl]-3,6,10,16-tetraazabicyclo[10.3.1] hexadeca-1(16),12,14-triene A mixture of compound 6-[5-(1-anthraquinone-carbonyl) amino-3-aza-2-carboxylpentanyl]-3,10-bis(2-nitrobenzenesulfonyl)-3,6,10,16-tetraazabicyclo[10.3.1]-hexadeca-1(16),12,14-triene (0.37 g, 0.4 mmol), PhSH (0.13 g, 1.2 mmol) and $K_2CO_3$ (1.0 g, 7.0 mmol) in 10 mL of anhydrous DMF was stirred at rt overnight. The solvent was evaporated and the residue was dissolved in $H_2O$ and extracted with $CHCl_3$. The combined organic phase was dried ($Na_2SO_4$) and concentrated. The residue was purified by flash chromatography on a silica gel column using 10:1 $CH_2Cl_2$—MeOH, MeOH and then 5:1 MeOH—$NH_4OH$ (30%) as eluents to give 0.15 g, (68%) of the title compound as a yellow foam.

$^1$H NMR (CDCl$_3$) δ 1.690–1.75 (m, 2H), 2.37–2.52 (m, 4H), 2.61–2.80 (m, 4H), 2.65–3.05 (br, 2H, ex $D_2O$), 3.11 (s, 2H), 3.53–3.69 (m, 4H), 3.78 (s, 2H), 3.93 (s, 2H), 6.95 (d, 2H, J=7.6 Hz), 7.49 (t, 1H, 7.6 Hz), 7.78–7.83 (m, 2H), 8.27–8.34 (m, 4H), 8.34–8.45 (br, 1H, ex $D_2O$), 8.64 (s, 1H), 9.00–9.18 (br, 1H, ex $D_2O$). $^{13}$C NMR (CDCl$_3$) δ 27.1, 29.7, 38.9, 40.7, 46.8, 48.4, 52.4, 53.4, 53.7, 58.2, 120.7, 125.6, 127.4, 127.7, 133.2, 133.5, 134.3, 134.9, 135.0, 136.9, 139.9, 158.5, 159.1, 166.0, 172.6, 182.5. HRMS (FAB) m/z 555.2734 ($C_{31}H_{35}N_6O_4$ requires 555.2720). Anal. Calcd for $C_{31}H_{34}N_6O_4 \cdot H_2O \cdot CH_2Cl_2$: C, 59.53; H, 5.89; N, 13.02. Found: C, 59.98; H, 5.47; N, 13.26.

EXAMPLE 93

6-[5-(1-Pyrenecarbonyl)amino-3-aza-2-carboxylpentanyl]-3,6,10,16-tetraazabicyclo[10.3.1] hexadeca-1(16),12,14-triene The title compound was prepared following the procedures illustrated above in Example 92 using 6-[5-(1-pyrenecarbonyl)amino-3-aza-2-carboxylpentanyl]-3,10-bis (2-nitrobenzenesulfonyl)-3,6,10,16-tetraazabicyclo-[10.3.1] hexadeca-1(16),12,14-triene (0.41 g, 0.43 mmol), PhSH (0.15 g, 1.29 mmol) and $K_2CO_3$ (0.5 g, 3.5 mmol) in 20 mL of anhydrous DMF. The compound was purified by flash chromatography on a silica gel column using MeOH and then 2:1 MeOH—$NH_4OH$ (30%) as eluents to give 0.2 g (85%) of the title compound as a yellow foam.

$^1$H NMR (CDCl$_3$) δ 1.42–1.61 (m, 2H), 1.70 (br, 2H, ex $D_2O$), 2.21–2.41 (m, 6H), 2.46–2.65 (m, 2H), 3.10 (s, 4H), 3.48 (s, 2H), 3.62–3.85 (m, 4H), 6.24 (d, 1H, J=8.0 Hz), 6.45 (d, 1H, J=7.4 Hz), 7.00 (t, 1H, J=7.6 Hz), 7.96–8.25 (m, 8H), 8.40 (d, 1H, J=9.2 Hz), 8.45 (br, 1H, ex $D_2O$), 8.59 (br, 1H, ex $D_2O$). $^{13}$C NMR (CDCl$_3$) δ 27.2, 38.3, 40.4, 46.4, 48.2, 52.0, 53.0, 53.2, 57.8, 58.3, 119.8, 120.0, 124.3, 124.4, 125.6, 126.2, 127.1, 128.2, 128.3, 128.4, 130.7, 131.1, 132.0, 136.0, 157.9, 159.4, 171.9. HRMS (FAB) m/z 549.2956 ($C_{33}H_{37}N_6O_2$ requires 549.2970). Anal. Calcd for $C_{33}H_{36}N_6O_2 \cdot H_2O$. C, 69.93; H, 6.71; N, 14.83. Found: C, 69.38; H, 6.72; N, 14.57.

EXAMPLE 94

4-Bromo-2,6-pyridinedimethyl ditosylate

A solution of tosyl chloride (19.6 g, 0.1 mol) in 150 mL of THF was added dropwise to a solution of 4-bromo-2,6-pyridinedimethanol (5.5 g, 25 mmol) and NaOH (6.0 g, 0.15 mol) in 300 mL of mixed solvent (1:1 THF—$H_2O$) at 0° C. The resulting solution was stirred at rt for 4 h. The reaction solution was poured onto 300 g of ice and 20 mL of HCl (37%) and extracted with $CHCl_3$. The combined organic phase was washed with 5% $NaHCO_3$ solution and $H_2O$, dried ($Na_2SO_4$), concentrated. The residue was recrystallized from ethanol to give 12.7 g (96%) of the title compound as a white crystal.

M.P. 102–103.5° C. $^1$H NMR (CDCl$_3$) δ 2.41 (s, 6H), 5.00 (s, 4H), 7.25 (s, 2H), 7.31 (d, 2H, J=8.2 Hz), 7.76 (d, 2H, J 8.2 Hz). $^{13}$C NMR (CDCl$_3$) δ 21.67, 70.5, 121.5, 128.0, 129.0, 132.9, 145.3, 146.0, 155.3. HRMS (FAB) m/z 526.0333 (C$_{21}$H$_{20}$NO$_6$S$_2$Br requires 526.0349). Anal. Calcd for C$_{21}$H$_{20}$NO$_6$S$_2$Br: C, 48.00; H, 3.84; N, 2.67. Found: C, 48.01; H, 3.94; N, 2.85.

EXAMPLE 95

3,6,10-Tris(2-nitrobenzenesulfonyl)-14-bromo-3,6,10,16-tetraazabicyclo[10.3.1]hexadeca-1(16),12,14-triene A mixture of compound 4-bromo-2,6-pyridinedimethyl ditosylate (1.18 g, 2.24 mmol), N$^1$, N$^3$, N$^6$-tris(2-nitrobenzenesulfonyl)-1,6-diamino-3-azahexane (prepared previously in Example 40 (b)) (1.57 g, 2.24 mmol) and Cs$_2$CO$_3$ (2.92 g, 8.96 mmol) was stirred at rt overnight. The solvent was evaporated and the residue was dissolved in CHCl$_3$—H$_2$O. The organic phase was separated and the aqueous phase was extracted with CHCl$_3$. The combined organic phase was dried (Na$_2$SO$_4$) and concentrated. The residue was purified by flash chromatography on a silica gel column using CH$_2$Cl$_2$ as an eluent to give 1.53 g (77%) of the title compound as a white foam.

$^1$H NMR (CDCl$_3$) δ 1.72 (m, 2H), 2.95–3.50 (m, 8H), 4.39 (s, 2H), 4.50 (s, 2H), 7.34–7.37 (m, 2H), 7.42–7.82 (m, 10H), 7.92 (m, 2H). $^{13}$C NMR (CDCl$_3$) δ 25.8, 26.2, 28.8, 47.2, 47.6, 48.9, 50.1, 123.2, 124.2, 124.3, 128.0, 130.1, 130.5, 131.6, 131.9, 132.2, 132.4, 133.9, 134.1, 145.8, 148.2, 148.4, 157.7, 157.8. HRMS (FAB) m/z 882.0531 (M+1)$^+$ (C$_{32}$H$_{33}$N$_7$O$_{12}$S$_3$Br requires 882.0533.

EXAMPLE 96

4-[5-(t-Boc)amino-pentanoxyl]-2,6-pyridinedicarboxyl dimethylate

To a solution of N-(t-Boc)aminopentanol (4.06 g, 20 mmol) and PPh$_3$ (5.76 g, 20 mmol) in 50 mL of anhydrous THF was added the solution of diethy azodicarboxylate (3.85 g, 20 mmol) at 0° C. A solution of 4-hydroxyl-2,6-pyridinedicarboxyl dimethylate (4.22 g, 20 mmol) (prepared as per the procedure of: Bradshaw et al., *Supramolecular Chemistry*, 1993, 1, 267–275) was added dropwise to the above solution at 0° C. and the resulting solution was stirred at rt for 24 h. The solvent was evaporated and the residue was partially dissolved in ethanol. After filtration, the solid was recrystallized from 1:2 EtOH-Hexanes to give 6.15 g (78%) of the title compound as a white crystal.

M.P. 98–99° C. $^1$H NMR (CDCl$_3$) δ 1.43 (s, 9H), 1.48–1.62 (m, 4H), 1.80–1.95 (m, 2H), 3.09–3.11 (m, 2H), 4.00 (s, 6H), 4.12 (t, 2H, J=6.0 Hz), 7.78 (s, 2H). $^{13}$C NMR (CDCl$_3$) δ 23.0, 28.3, 29.6, 40.2, 53.0, 66.9, 68.8, 78.8, 114.3, 149.6, 156.0, 165.0, 166.9. HRMS (FAB) m/z 397.1989 (M+1)$^+$ (C$_{19}$H$_{29}$N$_2$O$_7$ requires 397.1975). Anal. Calcd for C$_{19}$H$_{28}$N$_2$O$_7$: C, 57.55; H, 7.12; N, 7.07. Found: C, 57.56; H, 7.32; N, 7.33.

EXAMPLE 97

4-[5-(t-Boc)amino-pentanoxyl]-2,6-pyridinedimethanol

NaBH$_4$ is slowly added in portions to a mixture of 4-[5-(t-Boc)amino-pentanoxyl]-2,6-pyridinedicarboxyl dimethylate (4.0 g, 10 mmol) in 200 mL of ethanol. The resulting solution was stirred at rt for 2 h. and refluxed for 2 h. The solvent was evaporated and the residue was dissolved in CHCl$_3$—H$_2$O. The organic phase was separated and the aqueous phase was extracted with CHCl$_3$ and the combined organic phase was dried (Na$_2$SO$_4$) and concentrated. The residue was purified by flash chromatography on a silica gel column using 50:1 CH$_2$Cl$_2$—MeOH as an eluent to give 2.59 g (76%) of the title compound as a white solid.

M.P. 83.5–84.0° C. $^1$H NMR (CDCl$_3$) δ 1.36–1.62 (m, 13H), 1.75–1.90 (m, 2H), 3.06–3.21 (m, 2H), 4.02 (t, 2H, J=6.4 Hz), 4.55–4.70 (br, 2H, ex D$_2$O), 4.67 (s, 4H), 6.70 (s, 2H). $^{13}$C NMR (CDCl$_3$) δ 22.8, 28.4, 29.7, 40.3, 64.2, 67.8, 77.0, 105.5, 156.3, 161.4, 166.7, 227.8. HRMS (FAB) m/z 341.2076 (M+1)$^+$ (C$_{17}$H$_{29}$N$_2$O$_5$ requires 341.2076). Anal. Calcd for C$_{17}$H$_{28}$N$_2$O$_5$: C, 59.96; H, 8.29; N, 8.23. Found: C, 59.84; H, 8.38; N, 8.08.

EXAMPLE 98

4-[5-(t-Boc-amino)pentanoxyl]-2,6-pyridinedimethyl ditosylate

A solution of tosyl chloride (5.26 g, (27.6 mmol) in 100 mL of THF was added dropwise into the solution of 4-[5-(t-Boc)amino-pentanoxyl]-2,6-pyridinedimethanol (2.35 g, 6.90 mmol) and NaOH (1.66 g, 41.4 mmol) in 50 mL of THF and 50 mL of H$_2$O at 0° C. The resulting solution was stirred at rt for 4 h. The solution was poured into 30 g of ice and extracted with CHCl$_3$. The combined organic phase was washed with 5% NaHCO$_3$ solution and brine, dried (Na$_2$SO$_4$) and concentrated. The residue was purified by flash chromatography on a silica gel column using CH$_2$Cl$_2$ as the eluent to give 4.29 g (96%) of the title compound as a white solid.

$^1$H NMR (CDCl$_3$) δ 1.35–1.65 (m, 13H), 1.69–1.85 (m, 2H), 2.43 (s, 6H), 3.14 (q, 2H, J=6.0 Hz), 3.98 (t, 2H, J=6.2 Hz), 4.98 (s, 4H), 4.70–4.95 (br, 1H), 6.82 (s, 2H), 7.33 (d, 2H, J=7.8 Hz), 7.80 (d, 2H, J=8.2 Hz). $^{13}$C NMR (CDCl$_3$) δ 21.5, 13.1, 28.4, 29.7, 40.3, 68.2, 71.3, 78.8, 107.8, 127.9, 129.9, 132.6, 145.2, 155.0, 156.1, 166.6. HRMS (FAB) m/z 649.2261 (M+1)$^+$ (C$_{31}$H$_{40}$N$_2$O$_9$S$_2$ requires 649.2254). Anal. Calcd for C$_{31}$H$_{40}$N$_2$O$_9$S$_2$: C, 57.38; H, 6.22; N, 4.32. Found: C, 57.34; H, 6.23; N, 4.44.

EXAMPLE 99

3,6,10-Tris(2-nitrobenzenesulfonyl)-14-[5-(t-Boc)-amino-pentanoxy]-3,6,10,16-tetraazabicyclo[10.3.1]hexadeca-1(16),12,14-triene A mixture of 4-[5-(t-Boc-amino)pentanoxyl]-2,6-pyridinedimethyl ditosylate (4.2 g, 6.2 mmol), N$^1$, N$^3$, N$^6$-tris(2-nitrobenzenesulfonyl)-1,6-diamino-3-azahexane (prepared previously in Example 40 (b)), and Cs$_2$CO$_3$ (8.1 g, 24.8 mmol) in 450 mL of anhydrous DMF was stirred at rt overnight. The solvent was evaporated and the residue was dissolved in CHCl$_3$—H$_2$O. The organic phase was separated and the aqueous phase was extracted with CHCl$_3$. The combined organic phase was washed with brine, dried (Na$_2$SO$_4$) and concentrated. The residue was purified by flash chromatography on a silica gel column using 200:1 and then 100:1 CH$_2$Cl$_2$-MeOH as eluents to give 5.4 g (89%) of the title compound as a white foam.

$^1$H NMR (CDCl$_3$) δ 1.44 (s, 9H), 1.47–1.58 (m, 4H), 1.72–2.02 (m, 4H), 2.82–2.93 (m, 2H), 3.10–3.60 (m, 8H), 4.44 (t, 2H, J=6.2 Hz), 4.46 (s, 2H), 4.50 (s, 2H), 4.50–4.62 (br, 1H), 7.00 (d, 1H, J=2.2 Hz), 7.08 (d, 1 H, J=2.2 Hz), 7.86–8.15 (m, 12 H). $^{13}$C NMR (CDCl$_3$) δ 23.2, 27.2, 28.5, 29.8, 40.4, 46.1, 46.3, 46.7, 49.0, 55.6, 68.3, 79.0, 110.0, 110.6, 124.3, 130.5, 130.7, 130.9, 131.7, 131.9, 132.1, 132.3, 133.0, 133.9, 134.1, 147.9, 148.3, 156.1, 157.2, 158.1, 167.1. HRMS (FAB) m/z 977.2480 (M+1)$^+$ ($C_{40}H_{49}N_8O_{15}S_3$ requires 977.2480). Anal Calcd for $C_{40}H_{48}N_8O_{15}S_3$: C, 49.17; H, 4.96; N, 11.48. Found: C, 48.96; H, 5.09; N, 11.68.

EXAMPLE 100

3,6,10-tris(2-nitrobenzenesulfonyl)-14-(5-aminopentanoxyl)-3,6,10,16-tetraazabicyclo[10.3.1]hexadeca-1(16),12,14-triene A solution of 3,6,10-tris(2-nitrobenzenesulfonyl)-14-[5-(t-Boc)-amino-pentanoxy]-3,6,10,16-tetraazabicyclo[10.3.1]hexadeca-1(16),12,14-triene (5.23 g, 5.4 mmol) in 25 mL of TFA and 25 mL of $CH_2Cl_2$ was stirred at rt overnight. The solvent and the excess of TFA were evaporated and the residue was dissolved in $H_2O$. After adjusting the pH to about 10, the aqueous phase was extracted with ethyl acetate. The combined organic phase was dried ($Na_2SO_4$) and concentrated. The residue was purified by flash chromatography on a silica gel column using 200:1 $CH_2Cl_2$—MeOH as the eluent to give 1.3 g (28%) of the title compound as a white foam.

$^1$H NMR (CDCl$_3$) δ 1.41–1.70 (m, 6H, 2H ex D$_2$O), 1.70–2.00 (m, 4H), 2.78–2.95 (m, 4H), 3.2.0–3.38 (m, 4H), 3.49–3.54 (m, 2H), 4.06 (t, 2H, J=5.8 Hz), 4.37 (s, 2H), 4.40 (s, 2H), 7.01 (d, 1H, J=2.0 Hz), 7.09 (d, 1H, J=2.2 Hz), 7.60–7.78 (m, 12 H), 7.91–8.11 (m, 2H). $^{13}$C NMR (CDCl$_3$) δ 22.9, 27.1, 27.7, 28.3, 29.7, 40.0, 46.3, 46.7, 46.9, 55.5, 68.0, 110.1, 110.6, 124.4, 130.2, 130.6, 130.9, 131.9, 132.2, 132.3, 133.9, 134.1, 147.7, 147.9, 148.3, 157.2, 158.1, 167.1. HRMS (FAB) m/z 877.1970 (M+1)$^+$ ($C_{35}H_{41}N_8O_{13}S_3$ requires 877.1955). Anal. Calcd for $C_{35}H_{40}N_8O_{13}S_3 \cdot 2H_2O$: C, 46.04; H, 4.82. Found: C, 45.77; H, 4.91.

EXAMPLE 101

3,6,10-Tris(2-nitrobenzenesulfonyl)-14-[5-(1-pyrenecarbonyl)-amino-pentanoxy]-3,6,10,16-tetraazabicyclo-[10.3.1]hexadeca-1(16),12,14-triene A solution of 1-pyrenecarboxylic acid (0.1 g, 0.4 mmol) and 4-methymorpholine (50 mg, 0.4 mmol) in 10 mL of anhydrous DMF was stirred for 30 min. After addition of DCC (83 mg, 0.4 mmol) and HOBT (50 mg, 0.4 mmol), the solution was stirred at rt for another 30 min. A solution of 3,6,10-tris(2-nitrobenzenesulfonyl)-14-(5-aminopentanoxyl)-3,6,10,16-tetraazabicyclo[10.3.1]hexadeca-1(16),12,14-triene (0.35 g, 0.4 mmol) in 5 mL of DMF was added and the resulting solution was stirred at rt for 24 h. The solvent was evaporated and the residue was dissolved in CHCl$_3$—H$_2$O. The organic phase was separated and the aqueous phase was extracted with CHCl$_3$. The combined organic phase was dried (Na$_2$SO$_4$) and concentrated. The residue was purified by flash chromatography on a silica gel column using CH$_2$Cl$_2$ and then 100:1 CH$_2$Cl$_2$—MeOH as eluents to give 0.31 g (71%) of the title compound as an yellow foam.

$^1$H NMR (CDCl$_3$) δ 1.30–1.48 (m, 2H), 1.50–1.75 (m, 6H), 2.81–3.09 (m, 4H), 3.25–3.55 (m, 6H), 3.81–3.95 (m, 2H), 4.42 (s, 2H), 4.44 (s, 2H), 6.81 (s, 1H), 6.88 (s, 1H), 7.20–8.05 (m, 21H). $^{13}$C NMR (CDCl$_3$) δ 22.0, 26.0, 26.3, 27.4, 39.3, 45.5, 46.8, 48.3, 54.8, 67.5, 109.2, 109.6, 116.6, 117.9, 123.9, 124.2, 129.5, 129.6, 132.0, 132.2, 134.0, 134.2, 157.1, 158.0. HRMS (FAB) m/z 1105.2511 (M+1)$^+$ ($C_{52}H_{49}N_8O_{14}S_3$ requires 1105.2530).

EXAMPLE 102

14-[5-(1-Pyrenecarbonyl)amino-1-pentanoxyl]-3,6,10,16-tetraazabicyclo[10.3.1]hexadeca-1(16),12,14-triene A mixture of compound 3,6,10-tris(2-nitrobenzenesulfonyl)-14-[5-(1-pyrenecarbonyl)-amino-pentanoxy]-3,6,10,16-tetraazabicyclo[10.3.1]hexadeca-1(16),12,14-triene (0.30 g, 0.27 mmol), PhOH (0.14 g, 1.22 mmol) and K$_2$CO$_3$ (1.0 g, 0.72 mmol) in 10 mL of anhydrous DMF was stirred at rt overnight. The solvent was evaporated and the residue was dissolved in CHCl$_3$—H$_2$O. The organic phase was separated and the aqueous phase was extracted with CHCl$_3$. The combined organic phase was dried (Na$_2$SO$_4$) and concentrated. The residue was purified by flash chromatography using 5:1 CH$_2$Cl$_2$—MeOH and then 2:1 MeOH—NH$_4$OH (30%) as eluents to give 60 mg (41%) of the title compound as a yellow oil.

$^1$H NMR (CDCl$_3$) δ 1.52–2.01 (m, 8H), 1.80–2.40 (br, 3H, ex D$_2$O), 2.43–2.71 (m, 8H), 3.60–3.75 (m, 2H), 3.73 (s, 2H), 3.75 (s, 2H), 4.04 (t, 2H, J=6.2 Hz), 6.50 (s, 2H), 8.01–8.25 (m, 8H), 8.65 (d, 1H, J=9.4 Hz). $^{13}$C NMR (CDCl$_3$) δ 23.5, 28.6, 29.1, 29.5, 40.0, 47.9, 48.3, 48.7, 49.2, 52.9, 53.8, 67.6, 106.7, 107.2, 124.5, 124.8, 125.7, 126.4, 127.1, 128.6, 130.7, 131.2, 142.3, 161.4, 165.8, 170.1. HRMS (FAB) m/z 550.3167 (M+1)$^+$ ($C_{34}H_{40}N_5O_2$ requires 550.3182). CHCl$_3$: C, 62.80; H, 5.98; N, 10.46. Found: C, 62.79; H, 6.51; N, 10.19.

EXAMPLE 103

General Procedures for library preparation, preparation of Libraries 114–122

The scaffolds that were previously prepared in Examples 74, 78, 79, 80, 86, 87, 92, 93 and 102 are further used to prepare libraries. Each scaffold (1.0 equiv) and anhydrous K$_2$CO$_3$ (15 equiv) in acetonitrile was treated with a solution containing equimolar amounts of five selected reactive functionalities in acetonitrile (F$_{1-5}$) (3-[N-(N,N-(bis-t-Boc)-guanidinyl]-benzylbromide (L$_1$); N-methylene-carbonyl-N-guanidinyl piperazine (L$_{45}$); 2-bromo-N-[2'-(N'-t-Boc) ethylamino]-acetamide (L$_{49}$); 4-trifluoromethylbenzylbromide (Aldrich); and 2-bromomethyl pyridine-6-methanol (L$_{11}$) (2.1 equiv for libraries 114–121, and 3.15 equiv for library 122)). For each scaffold the resulting solution was stirred at rt for 4 h. The solvent was evaporated and the residue was dissolved in CHCl$_3$—H$_2$O. The organic phase was separated and the aqueous phase was extracted with CHCl$_3$. The combined organic phase was washed with brine, dried (Na$_2$SO$_4$), and evaporated under high vacuum to give the libraries as pale yellow foams having t-Boc protecting groups on some of the substituent groups. The protected libraries were dissolved in TFA and CH$_2$Cl$_2$ and stirred overnight. The solvent and the excess of TFA were evaporated and the residue was dissolved in 5N MeOH—HCl solution. The resulting solution was evaporated again under high vacuum to give the desired deprotected libraries 114–121 (as HCl salts) as pale yellow foams. The libraries were used for biological evaluation without further purification.

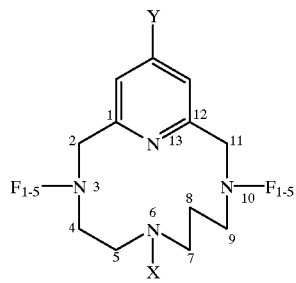

| Library # | Y | X |
|---|---|---|
| 114 | H | R₁ |
| 115 | H | R₂ |
| 116 | H | R₃ |
| 117 | H | R₄ |
| 118 | H | —(CH₂)₅—N(H)R₃ |
| 119 | H | —(CH₂)₅—N(H)R₄ |
| 120 | H | —(CH₂)₂—C(=O)N(H)—(CH₂)₂—N(H)R₃ |
| 121 | H | —(CH₂)₂—C(=O)N(H)—(CH₂)₂—N(H)R₄ |
| 122 | F₁₋₅ | —O—(CH₂)₅—N(H)R₄ |

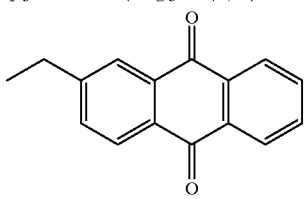

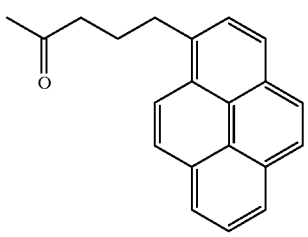

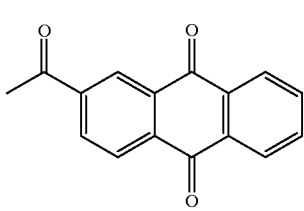

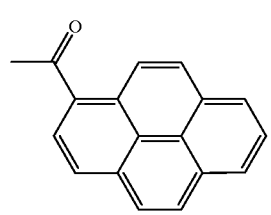

Libraries 114–122 were assayed as illustrated in the procedures below for activity against *S. pyogenes* and *E. Coli* imp. In another assay also illustrated below the libraries were assayed for their ability to effect transcription/translation.

| Library # | S. pyogenes | E. coli imp | Transcription/Translation |
|---|---|---|---|
| 114 | <12.5 | <50 | — |
| 115 | <12.5 | <12.5 | — |
| 116 | <12.5 | <50 | — |
| 117 | <12.5 | <12.5 | — |
| 118 | <12.5 | <12.5 | <100 |
| 119 | <12.5 | <12.5 | — |
| 120 | <12.5 | <25–100 | <100 |
| 121 | <12.5 | <12.5 | <50 |
| 122 | 12.5–25 | 12.5–25 | <100 |

EXAMPLE 104

14-Piperazinyl-3,6,10-tris (2-nitrobezenesulfonyl)-3,6,10,16-tetraazabicyclo[10.3.1]hexadeca-1(16),12,14-triene 80 mL of TFA was added to a stirred solution of tetra-protected 2,5,9-(tris-o-nitrobenzenesulfonyl)-triazadecane [2.6]-[4-(N4-t-Boc-piperazine-1-yl)]pyridinophane (19.2 g, 20.0 mmol) in 80 mL of CHCl₃ at 0° C. The reaction mixture was stirred at rt overnight and concentrated under vacuum. The solid residue was recrystallized from MeOH containing 2% CH₃CN to give 14.0 g (81%) of the triprotected title compound as yellow microcrystals (mp 195–197° C.).

Silica gel TLC R$_f$ 0.35 (50:1 MeOH-30% NH₄OH). $^1$H NMR (DMSO-d₆) δ 1.42–1.64 (m, 2H), 3.00–3.68 (m, 16H), 4.48 (s, 4H), 6.82 (s, 1H), 7.01 (s, 1H), 7.80–8.15 (m, 12H), 9.60 (br, 1H, ex D₂O). HRMS (FAB) m/z 860.178 (M+H)⁺ (C₃₄H₃₈N₉O₁₂S₃ requires 860.180). Anal. Calcd for C₃₄H₃₇N₉O₁₂S₃·3H₂O: C, 44.68; H, 4.73; N, 13.97. Found: C, 44.30; H, 4.60; N, 13.35.

EXAMPLE 105

16-Piperazinyl-3,7,12-tris(2-nitrobezenesulfonyl)-3,7,12,18-tetraazabicyclo[12.3.1]octadeca-1(18),14,16-triene The title compound was prepared following the procedures illustrated above in Example 104 using 2,6,11-(tris-o-nitrobenzenesulfonyl)-triazadodecane[2.6]-[4-(N4-t-Boc-piperazine-1-yl)]pyridinophane (11.9 g, 12.0 mmol) and 30 mL of TFA in 50 mL of CH₂Cl₂ at 0° C. The reaction mixture was stirred at rt for 3 h and concentrated under vacuum. Flash chromatographic purification using 9:1, 8:5, and then 1:5 EtOAc—MeOH as eluents gave 9.8 g (92%) of the title compound as a yellow foam.

Silica gel TLC R$_f$ 0.53 (9:1 CH₂Cl₂—MeOH). $^1$H NMR (CD₃CN) δ 1.22–1.40 (m, 4H), 1.65–1.79 (m, 2H), 3.00–3.15 (m, 4H), 3.20–3.30 (m, 6H), 3.32–3.40 (m, 2H), 3.54–3.60 (m, 4H), 4.30 (s, 2H), 4.49 (s, 2H), 6.77 (s, 2H), 7.64–7.82 (m, 10H), 7.96–8.02 (m, 2H), 9.20 (br, 1H, ex D₂O) $^{13}$C NMR (CD₃CN) δ 14.5, 19.2, 21.1, 26.7, 27.2, 29.5, 43.5, 44.0, 47.4, 48.3, 50.0, 51.0, 54.0, 55.1, 60.9, 108.5, 108.7, 118.3, 125.1, 125.2, 130.6, 131.0, 131.2, 132.1, 132.7, 133.1, 133.2, 135.1, 135.2, 135.3, 149.1, 149.2, 156.8, 157.0. HRMS (FAB) m/z 888.211 (M+H)⁺ (C₃₆H₄₂N₉O₁₂S₃ requires 888.211). Anal. Calcd for C₃₆H₄₁N₉O₁₂S₃·H₂O: C, 44.72; H, 4.79. Found: C, 44.31; H, 4.72.

EXAMPLE 106

14-[$N^4$-(Anthraquinone-2-methylene)piperazin-$N^1$-yl]-3,6,10-tris(2-nitrobezenesulfonyl)-3,6,10,16-tetraazabicyclo-[10.3.1]hexadeca-1(16),12,14-triene A mixture of 14-piperazinyl-3,6,10-tris(2-nitrobezenesulfonyl)-3,6,10,16-tetraazabicyclo[10.3.1]hexadeca-1(16),12,14-triene (1.72 g, 2.0 mmol), 2-(bromomethyl)anthraquinone (0.78 g, 2.6 mmol), and anhydrous $K_2CO_3$ (5.0 g, 36.0 mmol) in 40 mL of 1:1 DMF—$CH_3CN$ was stirred at rt overnight. The solvent was evaporated under vacuum and the residue was dissolved in $H_2O$—$CHCl_3$. The layers were separated and the aqueous phase was extracted with $CHCl_3$. The combined organic phase was washed with brine, dried ($Na_2SO_4$), and concentrated. The residue was purified by flash chromatography on a silica gel column using 2:1, 1:1, and then 0:1 hexanes-EtOAc as eluents to give 1.93 g (89%) of the title compound as a yellow foam.

Silica gel TLC $R_f$ 0.60 (100% EtOAc). $^1$H NMR ($CD_3CN$) δ 1.53–1.68 (m, 2H), 2.48–2.59 (m, 4H), 2.93–3.05 (m, 2H), 3.22–3.50 (m, 10H), 3.69 (s, 2H), 4.33 (s, 2H), 4.35 (s, 2H), 6.67 (d, 1H, J=1.8 Hz), 6.76 (d, 1H, J=1.8 Hz), 7.68–7.98 (m, 15H), 8.15–8.26 (m, 4H). HRMS (FAB) m/z 1080.229 (M+H)$^+$ ($C_{49}H_{46}N_9O_{14}S_3$ requires 1080.232). Anal. Calcd for $C_{49}H_{45}N_9O_{14}S_3$: C, 54.48; H, 4.19; N, 11.67. Found: C, 54.31; H, 4.15; N, 11.86.

EXAMPLE 107

16-[$N^4$-(Anthraquinone-2-methylene)piperazin-$N^1$-yl]-3,7,12-tris(2-nitrobezenesulfonyl)-3,7,12,18-tetraazabicyclo-[12.3.1]octadeca-1(18),14,16-triene The title compound was prepared following the procedures illustrated above in Example 106 using 16-piperazinyl-3,7,12-tris(2-nitrobezenesulfonyl)-3,7,12,18-tetraazabicyclo[12.3.1]octadeca-1(18),14,16-triene (4.48 g, 5.05 mmol), 2-(bromomethyl)anthraquinone (1.98 g, 6.57 mmol), and anhydrous $K_2CO_3$ (12.5 g, 91 mmol) in 100 mL of DMF. Chromatographic purification of the crude product using 100% EtOAc and then 9:1 EtOAc—MeOH as eluents to give 4.84 g (87%) of the title compound as a yellow foam.

Silica gel TLC $R_f$ 0.64 (95:5 $CH_2Cl_2$—MeOH). $^1$H NMR ($CD_3CN$) δ 1.20–1.42 (m, 6H), 1.69–1.78 (m, 2H), 2.48–2.55 (m, 4H), 2.98–3.15 (m, 4H), 3.20–3.40 (m, 8H), 3.71 (s, 2H), 4.26 (s, 2H), 4.44 (s, 2H), 6.64–6.68 (m, 2H), 7.68–8.02 (m, 15H), 8.20–8.40 (m, 4H). HRMS (FAB) m/z 1108.260 (M+H)$^+$ ($C_{51}H_{50}N_9O_{14}S_3$ requires 1108.263).

EXAMPLE 108

14-[$N^4$-(Pyrene-1-butyryl)piperazin-$N^1$-yl]-3,6,10-tris(2-nitrobezenesulfonyl)-3,6,10,16-tetraazabicyclo[10.3.1]-hexadeca-1(16),12,14-triene A mixture of 1-pyrenebutyric acid (1.50 g, 5.2 mmol, 1.3 equiv), N-methylmorpholine (0.75 mL), 1-hydroxybenzotriazole (HOBT) (0.71 g, 5.2 mmol) and 1,3-dicyclohexylcarbodiimide (DCC) (1.08 g, 5.2 mmol) in 20 mL of 1:1 $CH_2Cl_2$—$CH_3CN$ was stirred at rt for 15 min. A solution of 14-piperazinyl-3,6,10-tris(2-nitrobezenesulfonyl)-3,6,10,-16-tetraazabicyclo[10.3.1]hexadeca-1(16),12,14-triene (3.84 g, 4.0 mmol) in a 20 mL of $CH_3CN$ and 30 mL of DMF was added the above stirred solution. The resulting reaction mixture was stirred at rt for 24 h, and concentrated under vacuum. The residue was dissolved in $H_2O$—$CHCl_3$, and the solid was filtered off. The two layers of the filtrate were separated and the aqueous phase was extracted with $CHCl_3$. The combined organic phase was washed with brine, dried ($Na_2SO_4$), and concentrated. The residue was purified by flash chromatography on a silica gel column using 1:1 hexanes-EtOAc, 100% EtOAc, then 20:1, 10:1 and 5:1 EtOAc—MeOH as eluents to give 4.40 g (97%) of the title compound as a pale yellow foam.

Silica gel TLC $R_f$ 0.44 (100% EtOAc). $^1$H NMR ($CDCl_3$) δ 1.86–2.02 (m, 2H), 2.15–2.33 (m, 2H), 2.36–2.49 (m, 2H), 2.82–2.98 (m, 2H), 3.18–3.60 (m, 14H), 3.68–3.80 (m, 2H), 4.39 (s, 2H), 4.42 (s, 2H), 6.76 (d, 1H, J=1.8 Hz), 6.87 (d, 1H, J=1.8 Hz), 7.52–7.78 (m, 9H), 7.85–8.20 (m, 11H), 8.34 (d, 1H, J=9.2 Hz). HRMS (FAB) m/z 1130.288 (M+H)$^+$ ($C_{54}H_{52}N_9O_{13}S_3$ requires 1130.289). Anal. Calcd for $C_{54}H_{51}N_9O_{13}S_3$·$5H_2O$: C, 53.15; H, 5.03; N, 10.33. Found: C, 52.87; H, 4.83; N, 10.02.

EXAMPLE 109

16-[$N^4$-(Pyrene-1-butyryl)piperazin-$N^1$-yl]-3,7,12-tris(2-nitrobezenesulfonyl)-3,7,12,18-tetraazabicyclo[12.3.1]-octadeca-1(18),14,16-triene The title compound was prepared following the procedures illustrated above in Example 108 using 16-piperazinyl-3,7,12-tris(2-nitrobezenesulfonyl)-3,7,12,18-tetraazabicyclo[12.3.1]octadeca-1(18),14,16-triene (4.79 g, 5.39 mmol), 1-pyrenebutyric acid (1.65 g, 5.72 mmol), N-methylmorpholine (1.0 mL, 9.1 mmol), HOBT (0.95 g, 7.3 mmol) and DCC (1.45 g, 7.03 mmol) in 100 mL of DMF. Chromatographic purification of the crude product using 100% EtOAc and then 9:1 EtOAc—MeOH as eluents afforded 4.48 g (72%) of the title compound as a pale yellow foam.

Silica gel TLC $R_f$ 0.31 (5:1 EtOAc—MeOH). $^1$H NMR ($CD_3CN$) δ 1.20–1.27 (m, 2H), 1.30–1.38 (m, 2H), 1.65–1.78 (m, 2H), 2.09–2.18 (m, 2H), 2.46 (t, 2H, J=7.0 Hz), 2.96 (t, 2H, J=6.2 Hz), 3.07 (t, 2H, J=6.4 Hz), 3.15–3.28 (m, 6H), 3.30–3.40 (m, 4H), 3.45–3.51 (m, 2H), 3.58–3.64 (m, 2H), 4.24 (s, 2H), 4.44 (s, 2H), 6.61–6.65 (m, 2H), 7.58–7.81 (m, 10H), 7.90–7.97 (m, 1H), 7.98–8.08 (m, 5H), 8.10–8.21 (m, 4H), 8.42 (d, 1H, J=9.4 Hz). HRMS (FAB) m/z 1158.320 (M+H)$^+$ ($C_{56}H_{56}N_9O_{13}S_3$ requires 1158.316). Anal. Calcd for $C_{56}H_{55}N_9O_{13}S_3$: C, 58.07; H, 4,78; N, 10.88. Found: C, 57.89; H, 5.00; N, 10.80.

EXAMPLE 110

14-[$N^4$-(Anthraquinone-2-methylene)piperazin-$N^1$-yl]-3,6,10,16-tetraazabicyclo[10.3.1]hexadeca-1(16), 12,14-triene Thiophenol (0.66 mL, 0.71 g, 6.4 mmol, 3.9 equiv) was added to a stirred mixture of 14-[$N^4$-(anthraquinone-2-methylene) piperazin-$N^1$-yl]-3,6,10-tris(2-nitrobezenesulfonyl)-3,6,10,16-tetraazabicyclo[10.3.1] hexadeca-1(16),12,14-triene (1.75 g, 1.62 mmol) and anhydrous $K_2CO_3$ (5.0 g, 36 mmol) in 40 mL of anhydrous DMF. The resulting reaction mixture was stirred at rt overnight, concentrated, and treated with chloroform-water. The layers were separated and the aqueous phase was extracted with chloroform. The combined organic phase was washed with brine, dried ($Na_2SO_4$), and concentrated. The residue was purified by flash chromatography on a silica gel column using 100% MeOH, 10:1 and then 5:1 MeOH-30% $NH_4OH$ as eluents to afford 0.67 g (79%) of the title compound as a pale yellow foam.

Silica gel TLC $R_f$ 0.10 (5:1 MeOH-30% $NH_4OH$). $^1$H NMR ($CDCl_3$) δ 1.60–1.75 (m, 2H), 2.48–2.76 (m, 12H), 3.25–3.40 (m, 4H), 3.41–3.65 (br, 3H, ex D$_2$O), 3.69 (s, 2H), 3.73 (s, 2H), 6.38 (s, 2H), 7.71–7.84 (m, 3H), 8.18–8.32 (m, 4H). HRMS (FAB) m/z 525.300 (M+H)$^+$ (C$_{31}$H$_{37}$N$_6$O$_2$ requires 525.298). Anal. Calcd for C$_{31}$H$_{36}$N$_6$O$_2$.2.5H$_2$O: C, 65.36; H, 7.24; N, 14.75. Found: C, 65.49; H, 7.07; N, 14.88.

EXAMPLE 111

16-[N$^4$-(Anthraquinone-2-methylene) piperazin-N$^1$-yl]-3,7,12,18-tetraazabicyclo[12.3.1]octadeca-1(18), 14,16-triene The title compound was prepared following the procedures illustrated above in Example 110 using 16-[N$^4$-(anthraquinone-2-methylene)piperazin-N$^1$-yl]-3,7,12-tris (2-nitrobezenesulfonyl)-3,7,12,18-tetraazabicyclo[12.3.1]-octadeca-1(18),14,16-triene (4.64 g, 4.19 mmol), thiophenol (1.50 mL, 14.6 mmol), and anhydrous K$_2$CO$_3$ (5.8 g, 42.0 mmol) in 40 mL of DMF. The resulting reaction mixture was stirred at rt for 3.5 h and worked up as illustrated in Example 110. The residue was purified by flash chromatography on a silica gel column using 100% MeOH, and then 95:5 MeOH-30% NH$_4$OH as eluents to afford 1.62 g (70%) of the title compound as a pale yellow foam.

Silica gel TLC R$_f$ 0.19 (4:1 MeOH-30% NH$_4$OH). $^1$H NMR (CDCl$_3$) δ 1.20–1.50 (m, 6H), 2.50–2.78 (m, 16H), 3.30–3.42 (m, 4H), 3.72 (s, 2H), 3.74 (s, 2H), 3.80 (s, 2H), 6.46 (d, 2H, J=6.8 Hz), 7.76–7.88 (m, 3H), 8.24–8.38 (m, 4H). HRMS (FAB) m/z 553.331 (M+H)$^+$ (C$_{33}$H$_{41}$N$_6$O$_2$ requires 553.329). Anal. Calcd for C$_{33}$H$_{40}$N$_6$O$_2$.H$_2$O: C, 69.45; H, 7.35; N, 14.71. Found: C, 69.70; H, 6.87; N, 13.94.

EXAMPLE 112

14-[N$^4$-(Pyrene-1-butyryl)piperazin-N$^1$-yl]-3,6,10,16-tetraazabicyclo[10.3.1]hexadeca-1(16),12,14-triene The title compound was prepared following the procedures illustrated above in Example 110 using 14-[N$^4$-(pyrene-1-butyryl)piperazin-N$^1$-yl]-3,6,10-tris(2-nitrobezenesulfonyl)-3,6,10,16-tetraazabicyclo[10.3.1] hexadeca-1(16),12,14-triene (4.3 g, 3.8 mmol), anhydrous K$_2$CO$_3$ (10.0 g, 72 mmol), and thiophenbl (1.6 mL, 1.71 g, 15.5 mmol, 4.1 equiv) in 140 mL of anhydrous DMF. Flash chromatographic purification of the crude product on a silica gel column using 100% MeOH, 20:1, 5:1, and then 2:1 MeOH-30% NH$_4$OH as eluents afforded 2.04 g (93%) of the title compound as a white foam.

$^1$H NMR (CDCl$_3$) δ 1.53–1.67 (m, 2H), 2.12–2.25 (m, 2H), 2.25–2.37 (m, 2H), 2.46–2.80 (m, 10H), 2.97–3.08 (m, 2H), 3.16–3.30 (m, 4H), 3.39 (t, 2H, J=6.8 Hz), 3.69 (s, 2H), 3.70 (s, 2H), 6.25 (s, 2H), 7.28 (d, 1H, J=8.9 Hz), 7.90–8.16 (m, 7H), 8.29 (d, 1H, J=7.8 Hz). $^{13}$C NMR (CDCl$_3$) δ 26.7, 29.2, 32.1, 32.6, 40.7, 44.4, 45.7, 47.7, 48.3, 48.5, 49.3, 53.3, 54.2, 105.3, 123.4, 124.5, 124.8, 125.9, 126.3, 126.7, 127.1, 127.4, 128.8, 129.8, 130.8, 131.3, 136.0, 155.3, 160.5, 160.6, 171.1. HRMS (FAB) m/z 575.352 (M+H)$^+$ (C$_{36}$H$_{43}$N$_6$O requires 575.349). Anal. Calcd for C$_{36}$H$_{42}$N$_6$O.HCl: C, 70.74; H, 7.08; N, 13.75. Found: C, 70.70; H, 6.82; N, 13.46.

EXAMPLE 113

16-[N$^4$-(Pyrene-1-butyryl)piperazin-N$^1$-yl]-3,7,12, 18-tetraazabicyclo[12.3.1]octadeca-1(18),14,16-triene The title compound was prepared following the procedures illustrated above in Example 110 using 16-[N$^4$-(pyrene-1-butyryl)piperazin-N$^1$-yl]-3,7,12-tris(2-nitrobezenesulfonyl)-3,7,12,18-tetraazabicyclo[12.3.1]-octadeca-1(18),14,16-triene (4.26 g, 3.68 mmol), anhydrous K$_2$CO$_3$ (5.1 g, 36.8 mmol), and thiophenol (1.36 mL, 13.25 mmol) in 44 mL of anhydrous DMF. Flash chromatographic purification of the crude product on a silica gel column using 95:5, 20:1, and then 5:1 MeOH-30% NH$_4$OH as eluents afforded 1.50 g (68%) of the title compound as a white foam. Silica gel TLC R$_f$ 0.10 (4:1 MeOH-30% NH$_4$OH). $^1$H NMR (CDCl$_3$) δ 1.60–1.80 (m, 4H), 2.22–2.50 (m, 4H), 2.65–3.00 (m, 8H), 3.12–3.50 (m, 10H), 3.70–3.80 (m, 2H), 3.82 (s, 2H), 3.90 (s, 2H), 6.35–6.41 (m, 2H), 7.86 (d, 1H, J=8.0 Hz), 7.95–8.20 (m, 7H), 8.35 (d, 1H, J=8.0 Hz). HRMS (FAB) m/z 603.382 (M+H)$^+$ (C$_{38}$H$_{47}$N$_6$O requires 603.380). Anal. Calcd for C$_{38}$H$_{46}$N$_6$O.HCl.H$_2$O: C, 69.52; H,7.51; N, 12.80. Found: C, 69.97; H, 7.32; N, 12.70.

EXAMPLE 114

General Procedure for the Preparation of Libraries 123–132

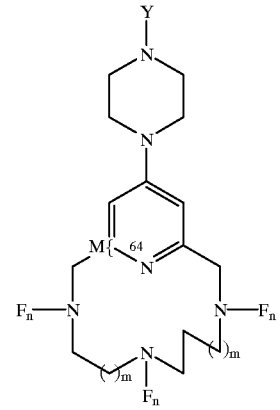

Formula VIII

| Library # | m | Y | Fn |
|---|---|---|---|
| 123 | 1 | H | L$_{(18, 29, 41, 42, 44 \text{ and } 45)}$ |
| 124 | 1 | H | L$_{(29, 41, 42, 47, 48 \text{ and } 49)}$ |
| 125 | 1 | H | L$_{(28, 30, 31, 32, 33 \text{ and } 34)}$ |
| 126 | 1 | H | L$_{(18, 44, 45, 47, 48 \text{ and } 49)}$ |
| 127 | 1 | H | L$_{(33, 37, 50, 51, 52 \text{ and } 54)}$ |
| 128 | 1 | H | L$_{(18, 25, 29, 36, 38 \text{ and } 40)}$ |
| 129 | 2 | H | L$_{(18, 40, 41, 42, 44 \text{ and } 45)}$ |
| 130 | 2 | H | L$_{(11, 47, 48, 49, 92 \text{ and } 93)}$ |
| 131 | 2 | H | L$_{(18, 44, 45, 47, 48 \text{ and } 49)}$ |
| 132 | 2 | H | L$_{(45, 49, 50, 51, 52 \text{ and } 89)}$ |

Each of the libraries was prepared by addition of a solution containing equimolar amounts of selected functionalities (L$_{n,s}$) (total 3.72 mmol, 3.1 equiv, 1.03 equiv per combinatorial site) in 10 mL of anhydrous CH$_3$CN to a stirred mixture of mono-t-Boc-protected scaffolds (2,5,9-trizadecane[2.6]-[4-(N4-t-Boc-piperazine-1-yl] pyridinophane Example 56 and 2,6,11-triazadodecane-[2.6]-[4-(N4-t-Boc-piperazine-1-yl)]pyridinophane. Example 55) (1.3 mmol) and anhydrous K$_2$CO$_3$ (3.0 g, 21 mmol, 16 equiv) in 20 mL of anhydrous CH$_3$CN. The respective reaction mixture was stirred at rt for 2 h (stirred at 60–70° C. for 24 h for libraries 127 and 132). Aminomethylated polystyrene resin (0.98 mmol/g, 0.5 g) was added and stirring was continued for for 1 h (stirred at 60–70° C. for 5 h for libraries 127 and 132) to remove the unreacted halides. The solvent was evaporated, and the residue was treated with CHCl$_3$—H$_2$O. The resin was filtered off, the layers were separated, and the aqueous phase was extracted with CHCl$_3$. The combined organic phase was washed with brine, dried (Na$_2$SO$_4$), and concentrated. The residue was purified by flash chromatography on a silica gel column using 1:1 hexanes-EtOAc to 100% EtOAc as eluents to give the t-Boc-protected libraries as pale yellow foams in 45–64% yields. The libraries were treated with TFA as per the procedures illustrated in Example 57A above to give the deprotected libraries. The deprotected libraries were subsequently converted to hydrochloride salts following the procedures illustrated in Example 103 above for Library 122. The overall yields ranged from 50 to 80%.

EXAMPLE 115

General Procedure for the Preparation of Libraries 133–138

Libraries 133–138 were prepared following the procedures illustrated above for libraries 123–132. The mono-t-Boc-protected scaffolds (2,5,9-triazadecane[2.6]-[4-(N4-t-Boc-piperazine-1-yl)]pyridinophane Example 56 and 2,6,11-triazadodecane[2.6]-[4-(N4-t-Boc-piperazine-1-yl)]-pyridinophane Example 55) were deprotected to give the corresponding scaffolds having Formula VIII with Y equal to H prior to treating the scaffolds with the selected functionalities ($L_{n,s}$). Each scaffold (1.3 mmol) and the selected set of functionalities (5.33 mmol, 4.1 equiv, 1.025 equiv per combinatorial site) and anhydrous K$_2$CO$_3$ in anhydrous DMF. For libraries 135 and 138, 4.4 equiv of the selected functionalities were used. The respective reaction mixtures were stirred at 60–70° C. for 24 h. The libraries were purified by silica gel flash column chromatography using 100% EtOAc and then 1:1 EtOAc—MeOH as eluents. The purified libraries were further treated with TFA to remove t-Boc-protecting groups present on functionality groups. The deprotected libraries were subsquently converted to hydrochloride salts following the procedures illustrated in Example 103 above for Library 122. The overall yields ranged from 59 to 73%.

| | Formula VIII | | |
|---|---|---|---|
| Library # | m | Y | Fn |
| 133 | 1 | F$_n$ | L$_{(18, 40, 41, 44 \text{ and } 45)}$ |
| 134 | 1 | F$_n$ | L$_{(26, 36, 47, 48 \text{ and } 49)}$ |
| 135 | 1 | F$_n$ | L$_{(37, 45, 50, 51 \text{ and } 52)}$ |
| 136 | 2 | F$_n$ | L$_{(18, 40, 41, 44 \text{ and } 45)}$ |
| 137 | 2 | F$_n$ | L$_{(26, 36, 47, 48 \text{ and } 49)}$ |
| 138 | 2 | F$_n$ | L$_{(45, 49, 51, 53 \text{ and } 54)}$ |

EXAMPLE 116

General Procedure for the Preparation of Libraries 139–150

Libraries 139–150 were prepared following the procedures illustrated above for libraries 123–132. The intercalator substituted scaffolds (14-[N$^4$-(anthraquinone-2-methylene) piperazin-N$^1$-yl]-3,6,10,16-tetraazabicyclo-[10.3.1]hexadeca-1(16),12,14-triene (Example 110); 16-[N$^4$-(anthraquinone-2-methylene)piperazin-N$^1$-yl]-3,7,12,18-tetraazabicyclo[12.3.1]octadeca-1(18),14,16-triene (Example 111); 14-[N$^4$-(pyrene-1-butyryl)piperazin-N$^1$-yl]-3,6,10,16-tetraazabicyclo[10.3.1]hexadeca-1(16),12,14-triene (Example 112); and 16-[N$^4$-(pyrene-1-butyryl) piperazin-N$^1$-yl]-3,7,12,18-tetraazabicyclo[12.3.1] octadeca-1(18),14,16-triene (Example 113)) (0.6 mmol), the selected set of functionalities (2.0 mmol, 3.3 equiv), and anhydrous K$_2$CO$_3$ in anhydrous DMF were used. For libraries 141, 144, 147 and 150 3.6 equiv of the corresponding functionality sets were used and the reaction mixtures were stirred at 60–70° C. for 24 h. The t-Boc-protected libraries were purified by flash chromatography using 1:4 hexanes-EtOAc, and then 10:1 to 2:1 EtOAc—MeOH as eluents, and obtained as pale yellow foams to white foams. The final libraries 139–150 were obtained in 60–85% yields as their hydrochloride salts without chromatographic purification.

| | Formula VIII | | |
|---|---|---|---|
| Library # | m | Fn | Y |
| 139 | 1 | L$_{(18, 40, 41, 44 \text{ and } 45)}$ | 2-methyleneanthraquinone |
| 140 | 1 | L$_{(26, 36, 47, 48 \text{ and } 49)}$ | 2-methyleneanthraquinone |
| 141 | 1 | L$_{(45, 49, 51, 53 \text{ and } 54)}$ | 2-methyleneanthraquinone |
| 142 | 2 | L$_{(18, 40, 41, 44 \text{ and } 45)}$ | 2-methyleneanthraquinone |
| 143 | 2 | L$_{(26, 36, 47, 48 \text{ and } 49)}$ | 2-methyleneanthraquinone |
| 144 | 2 | L$_{(45, 49, 50, 51 \text{ and } 54)}$ | 2-methyleneanthraquinone |
| 145 | 1 | L$_{(18, 40, 41, 44 \text{ and } 45)}$ | 1-butyryl pyrene |
| 146 | 1 | L$_{(26, 36, 47, 48 \text{ and } 49)}$ | 1-butyryl pyrene |
| 147 | 1 | L$_{(45, 49, 51, 53 \text{ and } 54)}$ | 1-butyryl pyrene |
| 148 | 2 | L$_{(18, 40, 41, 44 \text{ and } 45)}$ | 1-butyryl pyrene |
| 149 | 2 | L$_{(26, 36, 47, 48 \text{ and } 49)}$ | 1-butyryl pyrene |
| 150 | 2 | L$_{(45, 49, 50, 51 \text{ and } 54)}$ | 1-butyryl pyrene |

Libraries 123–150 were assayed as illustrated in the procedures below for activity against S. pyogenes and E. coli imp. In another assay, also illustrated below, the libraries were assayed for their ability to effect transcription/translation.

Biological Activities[a] of Libraries 123–150 in Growth Inhibition and RNA Binding Assays.

| Lib # | S. pyogenes | E. coli imp | tat/TAR | Transcription/Translation |
|---|---|---|---|---|
| 123 | 2–20 | 20–100 | 2.5 | <12.5 |
| 124 | 2–20 | 20–100 | 7 | 20–100 |
| 125 | — | — | — | — |
| 126 | — | — | 1.5 | 20–100 |
| 127 | 10–20 | 20–100 | 2.2 | <12.5 |
| 128 | 2–10 | <20 | — | — |
| 129 | 5–20 | 5–20 | — | 20–100 |
| 130 | 5–20 | 5–20 | — | — |
| 131 | 20–100 | 20–100 | — | 12.5–50 |
| 132 | <100 | <100 | — | 12.5–50 |
| 133 | 2–10 | 10–50 | 0.08 | 20–100 |
| 134 | 2–10 | 2–10 | — | — |
| 135 | 2–50 | 10–50 | 0.09 | 5–20 (13) |
| 136 | <100 | <100 | — | — |
| 137 | <100 | <100 | — | — |
| 138 | — | — | — | — |
| 139 | 2.5–12.5 | 5–12.5 | <20 | — |
| 140 | 2.5–12.5 | 5–12.5 | 20–100 | — |
| 141 | 5–50 | 5–12.5 | <20 | 12.5–25 |
| 142 | <25 | <25 | — | <100 |
| 143 | <25 | <25 | — | — |
| 144 | <25 | <25 | — | <100 |
| 145 | <12.5 | <12.5 | <20 | — |
| 146 | 12.5–50 | <12.5 | 20–100 | — |
| 147 | <12.5 | <12.5 | <20 | 12.5–50 |

-continued

Biological Activities[a] of Libraries 123–150 in Growth Inhibition and RNA Binding Assays.

| Lib # | S. pyogenes | E. coli imp | tat/TAR | Transcription /Translation |
|---|---|---|---|---|
| 148 | <25 | <25 | — | — |
| 149 | <25 | <25 | — | — |
| 150 | <25 | <25 | — | <100 |

[a]The MIC (minimum inhibitory concentration, $\mu$M) value is given as a range of library concentration (total concentration of compounds in library). After 24 h, the complete inhibition of growth was observed at the higher concentration of the given MIC, and the growth was observed at the lower concentration. Ampicillin and tetracycline were used as antibacterial references. IC$_{50}$ values ($\mu$M) were given for tat/TAR activity.
[b]CH$_2$CH=CHPh. [c]CH$_2$COOC(CH$_3$)$_3$. [d]C(=Nt-Boc)NHt-Boc. [e]C(=NH)NH$_2$. [f]anthroquinone-2-methyl. [g]pyrene-1-butyryl.

PROCEDURE 1

Antimicrobial Assays

Tier I

A. Streptococcus Pyogenes Gram Positive Specie

S. pyogenes [American Type Culture Collection (ATCC) # 14289] is used in this bacterial growth assay. To initiate the exponential phase of bacterial growth prior to the assay, a sample of bacteria is grown for 6 hours in Todd Hewitt Broth (Difco 0492-17-6) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2x Todd-Hewitt Broth (75 $\mu$L) are added to the compound mixtures (75 $\mu$L) for a total volume of 150 $\mu$L. The assays are performed in 96-well microplates with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no test compound or library is determined. Ampicillin and tetracycline antibiotic controls are concurrently tested in each screening assay.

Compounds are assayed in duplicate at a single dose. Compounds which show inhibitory activity are re-tested in duplicate at multiple doses to determine minimum inhibitory concentration (MIC).

B. E. coli imp- Gram Negative Specie

The strain E. coli imp- obtained from Spencer Benson (Sampson, B. A., Misra, R. & Benson, S. A., Genetics, 1989, 122, 491–501, Identification and characterization of a new gene of Escherichia coli K-12 involved in outer membrane permeability) is used in this bacterial growth assay. To initiate the exponential phase of bacterial growth prior to the assay, a sample of bacteria is grown for 6 hours in Mueller Hinton II Broth (BBL 12322) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2x Mueller Hinton II Broth (75 $\mu$L) are added to the compound mixtures (75$\mu$L) for a total volume of 150 $\mu$L. The assays are performed in 96-well microplates with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic controls are concurrently tested in each screening assay.

Compounds are assayed in duplicate at a single dose. Compounds which show inhibitory activity are re-tested in duplicate at multiple doses to determine minimum inhibitory concentration (MIC). Such compounds may be further tested with one or more gram positive bacteria such as but not limited to the Tier II et seq. organisms described in the following sections.

Tier II

A. Gram Positive

The following gram positive strains are used to test compounds which showed activity in at least one of the Tier I organisms: Staphylococcus aureus (ATCC #13709), Enterococcus hirae (ATCC #10541), Streptococcus pyogenes (ATCC #49399). To initiate the exponential phase of bacterial growth prior to the assay, a sample of bacteria is grown for 6 hours in Todd Hewitt Broth (Difco 0492-17-6) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2x Todd Hewitt Broth (75 $\mu$L) are added to the compound mixtures (75 $\mu$L) for a total volume of 150 $\mu$L. The assays are performed in 96-well microplates with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic controls are concurrently tested in each screening assay. Compounds are assayed in duplicate at multiple doses to determine minimum inhibitory concentration (MIC).

B. Gram Negative

The following gram negative strains are used to test compounds which showed activity in at least one of the Tier I organisms: Escherichia coli (ATCC #25922), Klebsiella pneumoniae (ATCC #10031), Proteus vulgaris (ATCC #13315), and Pseudomonas aeruginosa (ATCC #9027). To initiate the exponential phase of bacterial growth prior to the assay, a sample of bacteria is grown for 6 hours in Mueller Hinton II Broth (BBL 12322) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2x Mueller Hinton II Broth (75 $\mu$L) are added to the compound mixtures (75 $\mu$L) for a total volume of 150 $\mu$L. The assays are performed in 96-well microplates with approximately 1×10$^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin, tetracycline and ciprofloxacin antibiotic controls are concurrently tested in each screening assay.

Compounds are assayed in duplicate at multiple doses to determine minimum inhibitory concentration (MIC).

Tier III

A. Antifungal Assay Candida albicans

The strain *Candida albicans* (ATCC #10231) is used. To initiate the exponential phase of yeast growth prior to the assay, a sample of yeast is grown overnight at 25° C. in YM Broth (Difco 0711-17-1). The yeast cells are collected by centrifugation for 10 minutes at 3200 rpm, diluted and absorbance read at 595 nm. Yeast diluted in 2x YM Broth (75 µL) are added to the compound mixtures (75 µL) for a total volume of 150 µL. The assays are performed in 96-well microplates with approximately $1 \times 10^4$ cells per well. The plates are incubated at 25° C. and growth monitored at 48 hours by visual inspection of yeast growth. Amphotericin B anti-fungal control is concurrently tested in each screening assay.

Compounds are assayed in duplicate at multiple doses to determine minimum inhibitory concentration (MIC).

B. Red Blood Cell Lysis Assay

Compounds are tested for hemolysis of mammalian red blood cells. Horse red blood cells (Colorado Serum Co. #CS0004) are diluted 1:5 in 1x phosphate buffered saline (PBS). 50 µL diluted RBC's are added to 50 µL of test compound in 1x PBS (total volume=100 µL) in a round bottom 96-well microplate, mixed gently, and incubated 1 hour at 37° C. The microplate is then centrifuged for 5 minutes at 1000 rpm. The supernatant is diluted 1:5 (20 µL supernatant +80 µL 1x PBS) into a clean flat bottom 96-well microplate. Absorbance at 540 nm is read using a BioRad model 3550 UV microplate reader.

Compounds are tested in duplicate at multiple doses to determine the minimum hemolytic concentration (MHC).

Tier IV

RNA Binding Assay (In Vitro)

A. The Effect of Libraries on Tat/TAR Interactions

SPA Method (scintillation proximity assay)

A fast assay targeting tat/TAR interactions was developed for high through-put screening. The assay is used to rapidly identify compounds which are capable of disrupting the interaction of HIV-1 tat protein with the TAR RNA stem/loop structure.

1. Materials

The C terminal basic binding domain of the tat protein (a 39 residue tat peptide, aa 48–86 of HIV-1 tat protein) was synthesized by a contract lab and further labeled with $^{125}$I (specific activity 100 µCi/mL) at Amersham Life Sciences.

A 30 base RNA oligonucleotide (TAR oligonucleotide) consisting of the bulge and stem/loop structure of HIV TAR was synthesized at ISIS Pharmaceuticals and further labeled via conjugation with Biotin at the 3' end.

A PRB buffer was prepared consisting of: 50 mM Tris-HCl (pH 8.0), 0.01% NP-40, 10% glycerol, 1.5 mM $MgCl_2$, and 50 mM KCl.

Streptavidin coated SPA beads were purchased from Amersham Life Sciences.

Opaque 96 well plates were used purchased.

2. Methods

Streptavidin coated SPA beads are incubated for 20 minutes at room temperature in a PRB buffer with 0.1 µCi of the labeled peptide and 100 nM of the biotin conjugated RNA oligonucleotide. Incubations are performed in the presence or absence of test samples in a volume of 50 µL in an opaque 96 well plate. Following the incubation the plates are spun at 1000 rpm for 5 minutes to settle the SPA beads. The biotintylated TAR oligonucleotide binds the steptavidin coated SPA bead. The labeled tat peptide associated with the biotintylated TAR oligonucleotide excites the scintillant in the SPA bead, resulting in a quantifiable signal which can be read in the TopCount 96 well scintillation counter. Compounds that interfere with the tat/TAR interaction result in $^{125}$I tat floating free in buffer where excited electrons are quenched before transferring energy to scintillant in the SPA bead. This is observed as a decrease in signal.

PROCEDURE 2

Antimicrobial Mechanistic Assay

Bacterial DNA Gyrase

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all library pools are screened for inhibitory activity at 30 µM and then a dose response analysis is effected with active subsets. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 µM concentration.

PROCEDURE 3

Using Libraries for Identifying Metal Chelators and Imaging Agents

This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the pool under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library pool being assayed.

PROCEDURE 4

Assay of Combinatorial Library for $PLA_2$ Inhibitors

A preferred target for assay of combinatorially generated pools of compounds is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (Dennis, ibid.; Glaser et al., TiPs Reviews 1992, 14, 92; and Pruzanski et al., Inflammation 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., Inflammation 1988, 12, 549) or into the particular space of rabbits (Bomalaski et al., J. Immunol. 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., Science 1990, 250, 1541). Recently, the crystal structure of $PLA_2$ from human synovial fluid has been determined (Wery et al., Nature 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., Cold Spring Harbor Symp. Quant. Biol. 1987, 52, 441; Cho et al., J. Biol. Chem. 1988, 263, 11237; Yang et al., Biochem. J. 1989, 262, 855; and Noel et al., J. Am. Chem. Soc. 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., Biochemistry 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., FEBS Lett. 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., J. Am. Chem. Soc. 1987, 109, 8071; Lombardo et al., J. Biol. Chem. 1985, 260, 7234; Washburn et al., J. Biol. Chem. 1991, 266, 5042; Campbell et al., J. Chem. Soc., Chem. Commun. 1988, 1560; and Davidson et al., Biochem. Biophys. Res. Commun. 1986, 137, 587), reports describing in vivo activity are limited (Miyake et al., J. Pharmacol. Exp. Ther. 1992, 263, 1302).

In one preferred embodiment, compounds of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., J. Med. Chem. 1991, 34, 2260; Marki et al., Agents Actions 1993, 38, 202; and Tanaka et al., J. Antibiotics 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

After each round of synthesis as described in the above examples, the resulting libraries or pools of compounds are screened for inhibition of human type II $PLA_2$ enzymatic activity. The assay is effected at the conclusion of each round of synthesis to identify the wining pool from that round of synthesis. Concurrently, the libraries additionally can be screened in other in vitro assays to determine further mechanisms of inhibition.

The pools of the libraries are screened for inhibition of $PLA_2$ in the assay using *E. coli* labeled with $^3$H-oleic acid (Franson et al., *J. Lipid Res.* 1974, 15, 380; and Davidson et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each of the library pools is done in water: 10 µl of each pool is incubated for 5 minutes at room temperature with a mixture of 10 µl $PLA_2$, 20 µl 5× $PLA_2$ Buffer (500 mM Tris 7.0–7.5, 5 mM $CaCl_2$), and 50 µl water. Samples of each pool are run in duplicate. At this point, 10 µl of $^3$H *E. coli* cells is added. This mixture is incubated at 37° C. for 15 minutes. The enzymatic reaction is stopped with the addition of 50 µL 2M HCl and 50 µL fatty-acid-free BSA (20 mg/mL PBS), vortexed for 5 seconds, and centrifuged at high speed for 5 minutes. 165 µL of each supernate is then put into a scintillation vial containing 6 mL of scintillant (ScintiVerse) and cpms are measured in a Beckman Liquid Scintillation Counter. As a control, a reaction without the combinatorial pool is run alongside the other reactions as well as a baseline reaction containing no compounds of the invention as well as no $PLA_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II $PLA_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and a compound of the invention. $^{14}$C-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

PROCEDURE 5

Probes for the Detection of Specific Proteins and mRNA in Biological Samples

For the reliable, rapid, simultaneous quantification of multiple varieties of proteins or mRNA in a biological sample without the need to purify the protein or mRNA from other cellular components, a protein or mRNA of interest from a suitable biological sample, i.e., a blood borne virus, a bacterial pathogen product in stool, urine and other like biological samples, is identified using standard microbiological techniques. A probe comprising a compound of a combinatorial library of the invention is identified by a combinatorial search as noted in the above examples. Preferred for the protein probe are compounds synthesized to include chemical functional groups that act as hydrogen bond donors and acceptors, sulfhydryl groups, hydrophobic lipophilic moieties capable of hydrophobic interactions groups and groups capable of ionic interactions. The probe is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the probe thereon for a time sufficient to hybridize the protein or mRNA to the probe and thus form a linkage via the probe to the solid support. This immobilizes the protein or mRNA present in the sample to the CPG support. Other non-immobilized materials and components are then washed off the CPG with a wash media suitable for use with the biological sample. The mRNA on the support is labeled with ethidium bromide, biotin or a commercial radionucleotide and the amount of label immobilized on the CPG support is measured to indicate the amount of mRNA present in the biological sample. In a similar assay a protein is also labeled and quantified.

PROCEDURE 6

Leukotriene $B_4$ Assay

Leukotriene $B_4$ ($LTB_4$) has been implicated in a variety of human inflammatory diseases, and its pharmacological effects are mediated via its interaction with specific surface cell receptors. Library subsets are screened for competitive inhibition of radiolabeled $LTB_4$ binding to a receptor preparation.

A Nenquestm Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3$H] Leukotriene $B_4$ reagent is prepared by adding 5 mL of ligand diluent (phosphate buffer containing NaCl, $MgCl_{21}$ EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20° C.

Library subsets prepared as per general procedure of examples above are diluted to 5 µM, 50 µM and 500 µM in phosphate buffer (1× PBS, 0.1% azide and 0.1% BSA, pH 7.2), yielding final test concentrations of 0.5 µM, 5 µM and 50 µM, respectively. Samples are assayed in duplicate. [$^3$H] $LTB_4$ (25 µL) is added to 25 µL of either appropriately diluted standard (unlabeled $LTB_4$) or library subset. The receptor suspension (0.2 mL) is added to each tube. Samples are incubated at 4° C. for 2 hours. Controls include [$^3$H] $LTB_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library subset is determined relative to the standard (sample of ligand and receptor without library molecules).

Assay Results

Selected libraries have been tested for activity in the above procedures. The Table of activities below summarizes activity of these selected libraries.

Table of Activities

| Lib. # | S. Pyogenes | E. Coli Imp. | Transcription /Translation | Tat/tar |
|---|---|---|---|---|
| 1 | >100 | >100 | | |
| 2 | 5–10 | 10–20 | | |
| 3 | >100 | >100 | | |
| 4 | >100 | >100 | | |
| 5 | >100 | >100 | | |
| 6 | 5–10 | 5–10 | | |
| 7 | 2.5–5 | <2.5 | | |
| 8 | >100 | >100 | | |
| 9 | >100 | >100 | | |
| 10 | 5–25 | 5–25 | | |
| 11 | 1–5 | 5–25 | | |
| 12 | 5–25 | 1–5 | | |
| 13 | 5–25 | 5–25 | | |
| 14 | 5–25 | 5–25 | | |
| 15 | 1–5 | 1–5 | | |
| 16 | >100 | >100 | | |
| 21 | <20 | | | |
| 23 | <20 | | | |
| 24 | <20 | <20 | <100 | 7 |
| 28 | 1–20 | 20–100 | | |
| 29 | 20–100 | >100 | <100 | |
| 30 | | | 8.5–10 | |
| 31 | 20–100 | >100 | 8–20 | |
| 32 | <100 | <100 | <8 | <100 |
| 34 | <20 | | | <100 |
| 52 | <20 | <20 | | <12.5 |
| 56 | <20 | <20 | | 10 |
| 58 | 20 | 20 | | 10 |
| 60 | <20 | <20 | | <12.5 |
| 67 | 100 | | | |
| 68 | 100 | | | |
| 70 | <2 | <2 | | |
| 81 | <20 | <20 | | |
| 89 | <20 | <20 | | <100 |
| 96 | <20 | 20–100 | <100 | 2.5 |
| 97 | <20 | 20–100 | <100 | 7 |
| 99 | | | <20 | 1.5 |
| 100 | <20 | <20 | <20 | 2.2 |
| 101 | <20 | <20 | | |
| 103 | <2 | <2 | | |
| 104 | <2 | <2 | | |
| 105 | <2 | <2 | | |
| 106 | <2 | <2 | | |
| 108 | <20 | <20 | | |
| 109 | <20 | <20 | | |

The values shown are micromolar.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

PROCEDURE 7

Coupled Transcription/Translation Assay

E. coli S30 coupled transcription/translation extract was prepared as described by Burgess (Lesley, S. A., Brow, M. D., and Burgess, R. R., (1991), *Journal of Biological Chemistry* 266, 2632–2680). A 10× complete amino acid mix was prepared at 1 mM each amino acid. Plasmid DNA template (pBestLuc) containing the reporter gene for luciferase was purified on a Qiagen Ultrapure 100 column. S30 Premix without amino acids was special ordered from Promega (non-catalog item). The assay is performed in a total volume of 35 μL by combining 13 μL premix, 4 μL 10× amino acids, 5 μL S30 extract, 5 μL test compound and 8 μL (1 pg) pBestLuc template DNA in black 96-well microplates. The plates are mixed well and incubated at 37° C. for 35 minutes. The luciferase reporter enzyme is detected with Packard LucLite substrate (Catalog # 6016911) and luminescence is measured with a Packard TopCount.

The percentage of transcription/translation inhibition is determined relative to control wells which do not contain test compound. Compounds are assayed in duplicate at a single dose. Compounds which show inhibitory activity are re-tested in duplicate at multiple doses to determine the $IC_{50}$.

What is claimed is:

1. A compound having the formula:

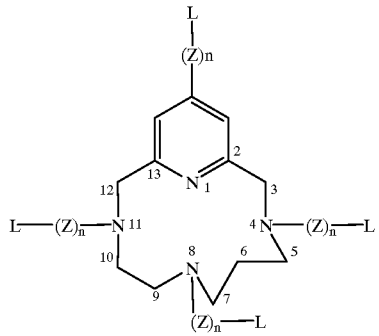

wherein:

Z is NH, O, or S;

n is 0 or 1; and

L is a substituent selected from the group consisting of guanidinylarylalkyl, aminoarylalkyl, amidinylpiperazinylcarbonylalkyl, piperazinylcarbonylalkyl, amidinylpiperazinylcarbonylarylalkyl, piperazinylcarbonylarylalkyl, guanidinylalkylaminocarbonylalkyl, aminoalkylaminocarbonylalkyl, guanidinylalkylaminocarbonylarylalkyl, aminoalkylaminocarbonylarylalkyl, benzoimidazolylalkyl, amidinyl, hydroxyamidinyl, hydroxyalkylpyridinylalkyl, arylalkyl, cinnamyl, amidylalkyl, aroyl, alkyloyl, aminoalkyloyl, hydroxaminoyalkyloyl, methoxyaminothioalkyloyl, indolylaminoalkyloyl, amidylaminoalkyloyl, hydroxylcarbonylaminoalkyloyl, guanidinylaminoalkyloyl, imidazolylaminoalkyloyl, amino substituted acyl, carboxyl-substituted arylalkyl and carboxyalkyl-substituted arylalkyl, hydroxysulfonylalkyl, alkyloxycarbonyl substituted pyrimidinyl, alkyloxycarbonyl substituted pyridinyl, carboxyl substituted pyrmidinyl, carboxyl substituted pyridinyl, guanidinylcarbonylalkyl, guanidinylcarbonylarylalkyl, guanidinylcarbonyl substituted pyrimidinyl, guanidinylcarbonyl substituted pyridinyl, alkyloxyphosphatealkyl, pyridinylalkyl, cyanoalkyl, cyanoaryl, nitroalkyl, nitroaryl, alkyloxyalkyl, phenolylalkyl, hydroxylarylalkyl, hydroxyquinolinylalkyl, alkylaminocarbonyl, arylaminocarbonyl, furanylaminocarbonyl, thiofuranylaminocarbonyl, alkylaminothiocarbonyl;

arylaminothiocarbonyl, furanylaminothiocarbonyl, thiofuranylaminothiocarbonyl, pyridinylaminothiocarbonyl, 1,2,3-oxadiazolylalkyl, anthraquinone-2-methyl, pyrene-1-butyryl, anthraquinone-2-carbonyl, pyrene-1-carbonyl, 5-(anthraquinone-2-carbonyl)amino-1-pentanyl, 5-(pyrene-1-carbonyl)amino-1-pentanyl, [[[2-(anthraquinone-2-carbonyl)amino]ethylamino]carbonyl]methyl, [[[2-pyrene-1-carbonyl)amino]ethylamino]carbonyl]methyl, and [5-pyrene-1-carbonyl)amino]pentanoxy;

or L is a conjugate group.

2. The compound of claim 1 wherein said substituent bears a chemical blocking group.

3. The compound of claim 1 wherein said compound exhibits antibacterial activity.

* * * * *